US009416149B2

(12) United States Patent
Hohl et al.

(10) Patent No.: US 9,416,149 B2
(45) Date of Patent: Aug. 16, 2016

(54) METHODS TO MODULATE RAC1 IMPORT AND TO TREAT PULMONARY FIBROSIS

(71) Applicant: University of Iowa Research Foundation, Iowa City, IA (US)

(72) Inventors: Raymond J. Hohl, Iowa City, IA (US); A. Brent Carter, Iowa City, IA (US)

(73) Assignee: University of Iowa Research Foundation, Iowa City, IA (US)

(*) Notice: Subject to any disclaimer, the term of this patent is extended or adjusted under 35 U.S.C. 154(b) by 15 days.

(21) Appl. No.: 14/262,448

(22) Filed: Apr. 25, 2014

(65) Prior Publication Data

US 2015/0005261 A1  Jan. 1, 2015

Related U.S. Application Data

(60) Provisional application No. 61/816,057, filed on Apr. 25, 2013.

(51) Int. Cl.

| | |
|---|---|
| *A61K 31/66* | (2006.01) |
| *C07F 9/653* | (2006.01) |
| *C07F 9/38* | (2006.01) |
| *A61K 45/00* | (2006.01) |
| *A61K 31/663* | (2006.01) |

(52) U.S. Cl.
CPC ............ *C07F 9/65318* (2013.01); *A61K 31/663* (2013.01); *A61K 45/00* (2013.01); *C07F 9/3839* (2013.01); *C07F 9/3856* (2013.01); *C07F 9/653* (2013.01)

(58) Field of Classification Search
None
See application file for complete search history.

(56) References Cited

U.S. PATENT DOCUMENTS 7,268,124 B2 * 9/2007 Wiemer ................. C07F 9/3847
514/102
2006/0052347 A1  3/2006 Wiemer et al.

FOREIGN PATENT DOCUMENTS

WO  2014008407 A1  1/2014

OTHER PUBLICATIONS

Li et al. Biochemical Pharmacology 79 (2010) 399-406.*
Yeniçerioglu et al. Renal Failure 32 (2010) Abstract.*
Attfield, et al., "Changing Patterns of Pneumoconiosis Mortality—United States, 1968-2000", MMWR, 53, 627-632 (2004). (Reprinted) JAMA vol. 292 (7), 795-796 (2004).
Guidotti, et al., "Diagnosis and Initial Management of Nonmalignant Diseases Related to Asbestos", American Journal of Respiratory and Critical Care Medicine 170, 691-715 (2004).
Hall, et al., "Requirements for Vav guanine nucleotide exchange factors and Rho GTPases in FcgammaR- and complement-mediated phagocytosis", Immunity 24, 305-316 (2006).
He, et al., "Mitochondrial Cu,Zn-superoxide dismutase mediates pulmonary fibrosis by augmenting H2O2 generation", J. Biol. Chem. 286, 15597-15607 (2011).
Mossman, et al., "Evidence supporting a role for active oxygen species in asbestos-induced toxicity and lung disease", Environmental Health Perspectives 81, 91-94 (1989).
Murthy, et al., "Modulation of reactive oxygen species by Rac1 or catalase prevents asbestos-induced pulmonary fibrosis", American Journal of Physiology—Lung Cellular and Molecular Physiology 297, L846-L855 (2009).
Murthy, et al., "Rac1-mediated mitochondrial H2O2 generation regulates MMP-9 gene expression in macrophages via inhibition of SP-1 and AP-1", J. Biol. Chem. 285, 25062-25073 (2010).
Osborn-Heaford, et al., "Inhibition of RAC1 Gerarnylgeranylation Prevents the Development of Pulmonary Fibrosis by Attenuating Mitochondrial Oxidative Stress, H2O2", Combined Annual Meeting of the Central-Society-for-Clinical-and-Translational-Research (CSCTR) and Midwestern-Section-American-Federation-for-Medical-Research (MWAFMR), Chicago, IL, Abstract and Poster, 2 pages, Apr. 26-27, 2012. [Journal of Investigative Medicine vol. 60 (4), 748-749 (Apr. 2012).].
Osborn-Heaford, et al., "Mitochondrial Rac1 GTPase Import and Electron Transfer from Cytochrome c Are Required for Pulmonary Fibrosis", Journal of Biological Chemistry vol. 287 (5), 3301-3312 (2012).
Osborn-Heaford, et al., "RAC1 Mitochondrial Import and Mitochondrial H2O2 Generation is Modulated by Geranylgeranylation of the Cysteine-189 Residue", Joint Annual Meeting of the Central-Society-for-Clinical-Research (CSCR) and Midwestern Section American Federation for Medical Research (MSAFMR), Chicago, IL, 2 pages, Apr. 26-27, 2012.
Osborn-Heaford, et al., "Targeting the isoprenoid pathway to abrogate progression of pulmonary fibrosis", Free Radic Biol Med. 86, 47-56 (2015).
Patent Cooperation Treaty, International Searching Authority, Search Report and Written Opinion for PCT/US2014/35529, 10 pages, Sep. 2, 2014.
Roberts, et al., "Deficiency of the hematopoietic cell-specific Rho family GTPase Rac2 is characterized by abnormalities in neutrophil function and host defense", Immunity 10, 183-196 (1999).
Watts, et al., "Simvastatin Inhibits Growth Factor Expression and Modulates Profibrogenic Markers in Lung Fibroblasts", Am J Respir Cell Mol Biol vol. 32, 290-300 (2005).
Wells, et al., "Rac1-deficient macrophages exhibit defects in cell spreading and membrane ruffling but not migration", J. Cell Sci. 117, 1259-1268 (2004).
Zeng, et al., "Role for RhoB and PRK in the suppression of epithelial cell transformation by farnesyltransferase inhibitors", Oncogene 22, 1124-1134 (2003).

* cited by examiner

*Primary Examiner* — Jeffrey S Lundgren
*Assistant Examiner* — Michael Schmitt
(74) *Attorney, Agent, or Firm* — Viksnins Harris & Padys PLLP

(57) ABSTRACT

The invention provides methods for treating fibrosis, as well as methods for modulating mitochondrial peroxide production in a cell, and methods for modulating the import of Rac1 into the mitochondria of a cell.

12 Claims, 12 Drawing Sheets

METHODS TO MODULATE RAC1 IMPORT AND TO TREAT PULMONARY FIBROSIS

PRIORITY OF INVENTION

This application claims priority to U.S. Provisional Application No. 61/816,057, filed 25 Apr. 2013. The entire content of this provisional application is incorporated herein by reference.

STATEMENT OF GOVERNMENT SUPPORT

This invention was made with government support under 5R01ES015981-08 awarded by The National Institutes of Health. The government has certain rights in the invention.

BACKGROUND

An important and prototypical type of pulmonary fibrosis occurs after exposure to asbestos, which results in an interstitial pneumonitis and subsequent collagen deposition. Although strict regulatory controls are in place to limit exposure, more than 1.3 million workers continue to be exposed to hazardous levels of asbestos annually (Attfield, M. D., et al., (Reprinted from MMWR, vol 53, pg 627-632, 2004), *Jama-Journal of the American Medical Association* 2004, 292, 795-796; and Guidotti, T. L., et al., *American Journal of Respiratory and Critical Care Medicine* 2004, 170, 691-715).

The development of pulmonary fibrosis is a complex process that results in aberrant remodeling of lung tissue. The modulation of lung remodeling during pulmonary fibrosis is poorly understood, and no effective therapeutic options have come about to prevent disease development. Thus, understanding the mechanism(s) by which aberrant remodeling is regulated may provide a potential target for therapy.

The generation of reactive oxygen species (ROS), including $H_2O_2$, plays a critical role in tissue injury and consequent fibrosis by modulating extracellular matrix deposition (Murthy, S., et al., *J. Biol. Chem.* 2010, 285, 25062-25073; and He, C., et al., *J. Biol. Chem.* 2011, 286, 15597-15607). The production of ROS is accentuated by the inefficient phagocytosis of asbestos fibers by alveolar macrophages (Mossman, B. T., et al., *Environmental Health Perspectives* 1989, 81, 91-94). It has been shown that alveolar macrophages obtained from patients with pulmonary fibrosis produce high levels of $H_2O_2$ and that the primary source of $H_2O_2$ generated in alveolar macrophages in the setting of pulmonary fibrosis is the mitochondria (He, C., et al., *J. Biol. Chem.* 2011, 286, 15597-15607). The generation of $H_2O_2$ is critical for the fibrotic response in lung injury because abrogating mitochondrial oxidant stress or administration of catalase attenuates the development of pulmonary fibrosis in mice (He, C., et al., *J. Biol. Chem.* 2011, 286, 15597-15607; and Murthy, S., et al., *American Journal of Physiology-Lung Cellular and Molecular Physiology* 2009, 297, L846-L855. Rac1 is a member of the Rho family of guanosine 5'-triphosphate (GTP)-binding proteins. Rac1 regulates several cellular functions, such as actin polymerization and migration, cell adhesion, and phagocytosis in macrophages, which are all necessary processes to engulf asbestos fibers (Hall, A. B., et al., *Immunity* 2006, 24, 305-316; Roberts, A. W., et al., *Immunity* 1999, 10, 183-196; and Wells, C. M., et al., *J. Cell Sci.* 2004, 117, 1259-1268). The C-terminal cysteine residue in Rho GTP-binding proteins, such as Rac1, can be modified by geranylgeranylation. This post-translational modification is important for Rac1 activation and interaction with other proteins (Zeng, P. Y., et al., *Oncogene* 2003, 22, 1124-1134).

It has recently been demonstrated that Rac1 is active in the alveolar macrophages of obtained from patients with asbestosis (Osborn-Heaford, H. L., et al., *J. Biol. Chem.* 2012, 287, 3301-3312.). This report also demonstrated that the Rac1 activation in the mitochondria of alveolar macrophages increases reactive oxygen species (ROS) such as peroxide in the lung, and that mice null for Rac1 show less ROS and decreased fibrosis relative to wild-type mice. The activity of Rac1 in this regard was shown to be dependent on the C-terminal cysteine residue of Rac1. U.S. Pat. No. 7,268,124 and International Application WO2014/008407 describe compounds that are reported to have activity as GGPP Synthase inhibitors.

There is currently a need for compounds and methods that are useful for treating fibrosis such as pulmonary fibrosis.

SUMMARY OF THE INVENTION

The present invention provides methods that are useful for treating fibrosis (e.g., pulmonary fibrosis), as well as methods for modulating mitochondrial peroxide production in a cell, and methods for modulating the import of Rac1 into the mitochondria of a cell, especially macrophages.

In one embodiment the invention provides a method to treat fibrosis (e.g., pulmonary fibrosis) in an animal (e.g., a mammal such as a human) in need thereof comprising administering to the animal an effective amount of a geranylgeranyl pyrophosphate (GGPP) synthase inhibitor or a pharmaceutically acceptable salt or prodrug thereof (e.g., a compound of formula I, formula II or formula III or a pharmaceutically acceptable salt or prodrug thereof as described herein).

In one embodiment the invention provides a method to treat fibrosis (e.g., pulmonary fibrosis) in an animal (e.g., a mammal such as a human) comprising administering to the animal a compound of formula I, formula II or formula III:

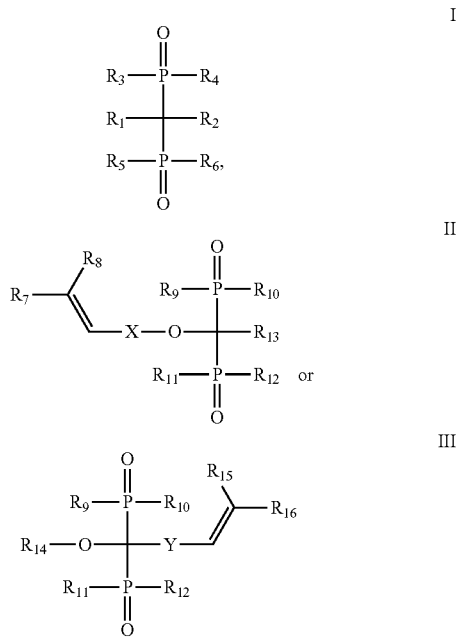

wherein:
$R_1$ is a saturated or unsaturated $(C_5-C_{20})$alkyl chain that optionally comprises one or more aryl rings in the chain and that is optionally substituted with one or more halo, trifluoromethyl, —OR$_a$, —P(=O)(OR$_a$)$_2$, or —NR$_b$R$_c$;

R$_2$ is a saturated or unsaturated (C$_5$-C$_{20}$)alkyl chain that optionally comprises one or more aryl rings in the chain and that is optionally substituted with one or more halo, trifluoromethyl, —OR$_a$, —P(=O)(OR$_a$)$_2$, or —NR$_b$R$_c$;

each R$_3$, R$_4$, R$_5$, and R$_6$ is independently OH or (C$_1$-C$_6$)alkoxy;

each R$_a$ is independently H, (C$_1$-C$_6$)alkyl, or aryl; and each R$_b$ and R$_c$ is independently H, (C$_1$-C$_6$)alkyl, or aryl; or R$_b$ and R$_c$ together with the nitrogen to which they are attached form a pyrrolidino, piperidino, morpholino, or thiomorpholino ring;

wherein any aryl of R$_1$, R$_2$, R$_a$, R$_b$ or R$_c$ is optionally substituted with one or more (C$_1$-C$_6$)alkyl, (C$_1$-C$_6$)alkoxy, (C$_1$-C$_6$)alkanoyl, (C$_1$-C$_6$)alkanoyloxy, (C$_1$-C$_6$)alkoxycarbonyl, halo, cyano, nitro, carboxy, trifluoromethyl, trifluoromethoxy, —NR$_d$R$_e$, or —S(O)$_2$NR$_c$R$_e$, wherein each R$_d$ and R$_e$ is independently H or (C$_1$-C$_6$)alkyl;

X is (C$_1$-C$_6$)alkyl;

Y is (C$_1$-C$_6$)alkyl;

R$_7$ is a saturated or unsaturated (C$_1$-C$_{20}$)alkyl chain that optionally comprises one or more aryl or heteroaryl rings in the chain wherein (C$_1$-C$_{20}$)alkyl is optionally substituted with one or more halo, cyano, nitro, carboxy, trifluoromethyl, trifluoromethoxy, aryl, heteroaryl, —NR$_m$R$_n$, or —S(O)$_2$NR$_p$R$_q$ and wherein any aryl or heteroaryl is optionally substituted with one or more (C$_1$-C$_6$)alkyl, (C$_1$-C$_6$)alkoxy, (C$_1$-C$_6$)alkanoyl, (C$_1$-C$_6$)alkanoyloxy, (C$_1$-C$_6$)alkoxycarbonyl, halo, cyano, nitro, carboxy, trifluoromethyl, trifluoromethoxy, —NR$_{a1}$R$_{b1}$, or —S(O)$_2$NR$_{c1}$R$_{d1}$;

R$_8$ is H or a saturated or unsaturated (C$_1$-C$_{20}$)alkyl chain that optionally comprises one or more aryl or heteroaryl rings in the chain wherein (C$_1$-C$_{20}$)alkyl is optionally substituted with one or more halo, cyano, nitro, carboxy, trifluoromethyl, trifluoromethoxy, aryl, heteroaryl, —NR$_m$R$_n$, or —S(O)$_2$NR$_p$R$_q$ and wherein any aryl or heteroaryl is optionally substituted with one or more (C$_1$-C$_6$)alkyl, (C$_1$-C$_6$)alkoxy, (C$_1$-C$_6$)alkanoyl, (C$_1$-C$_6$)alkanoyloxy, (C$_1$-C$_6$)alkoxycarbonyl, halo, cyano, nitro, carboxy, trifluoromethyl, trifluoromethoxy, —NR$_{a1}$R$_{b1}$, or —S(O)$_2$NR$_{c1}$R$_{d1}$;

each R$_9$, R$_{10}$, R$_{11}$, and R$_{12}$ is independently OH or (C$_1$-C$_6$)alkoxy;

R$_{13}$ is a saturated or unsaturated (C$_1$-C$_{20}$)alkyl chain that optionally comprises one or more aryl or heteroaryl rings in the chain wherein (C$_1$-C$_{20}$)alkyl is optionally substituted with one or more halo, cyano, nitro, carboxy, trifluoromethyl, trifluoromethoxy, aryl, heteroaryl, —NR$_m$R$_n$, or —S(O)$_2$NR$_p$R$_q$ and wherein any aryl or heteroaryl is optionally substituted with one or more (C$_1$-C$_6$)alkyl, (C$_1$-C$_6$)alkoxy, (C$_1$-C$_6$)alkanoyl, (C$_1$-C$_6$)alkanoyloxy, (C$_1$-C$_6$)alkoxycarbonyl, halo, cyano, nitro, carboxy, trifluoromethyl, trifluoromethoxy, aryl, heteroaryl, or —S(O)$_2$NR$_{c1}$R$_{d1}$;

R$_{14}$ is a saturated or unsaturated (C$_1$-C$_{20}$)alkyl chain that optionally comprises one or more aryl or heteroaryl rings in the chain wherein (C$_1$-C$_{20}$)alkyl is optionally substituted with one or more halo, cyano, nitro, carboxy, trifluoromethyl, trifluoromethoxy, aryl, heteroaryl, —NR$_m$R$_n$, or S(O)$_2$NR$_p$R$_q$ and wherein any aryl or heteroaryl is optionally substituted with one or more (C$_1$-C$_6$)alkyl, (C$_1$-C$_6$)alkoxy, (C$_1$-C$_6$)alkanoyl, (C$_1$-C$_6$)alkanoyloxy, (C$_1$-C$_6$)alkoxycarbonyl, halo, cyano, nitro, carboxy, trifluoromethyl, trifluoromethoxy, —NR$_{a1}$R$_{b1}$, aryl, heteroaryl, or —S(O)$_2$NR$_{c1}$R$_{d1}$;

R$_{15}$ is a saturated or unsaturated (C$_1$-C$_{20}$)alkyl chain that optionally comprises one or more aryl or heteroaryl rings in the chain wherein (C$_1$-C$_{20}$)alkyl is optionally substituted with one or more halo, cyano, nitro, carboxy, trifluoromethyl, trifluoromethoxy, aryl, heteroaryl, —NR$_m$R$_n$, or —S(O)$_2$NR$_p$R$_q$ and wherein any aryl or heteroaryl is optionally substituted with one or more (C$_1$-C$_6$)alkyl, (C$_1$-C$_6$)alkoxy, (C$_1$-C$_6$)alkanoyl, (C$_1$-C$_6$)alkanoyloxy, (C$_1$-C$_6$)alkoxycarbonyl, halo, cyano, nitro, carboxy, trifluoromethyl, trifluoromethoxy, —NR$_{a1}$R$_{b1}$, or —S(O)$_2$NR$_{c1}$R$_{d1}$;

R$_{16}$ is H or a saturated or unsaturated (C$_1$-C$_{20}$)alkyl chain that optionally comprises one or more aryl or heteroaryl rings in the chain wherein (C$_1$-C$_{20}$)alkyl is optionally substituted with one or more halo, cyano, nitro, carboxy, trifluoromethyl, trifluoromethoxy, aryl, heteroaryl, —NR$_m$R$_n$, or —S(O)$_2$NR$_p$R$_q$ and wherein any aryl or heteroaryl is optionally substituted with one or more (C$_1$-C$_6$)alkyl, (C$_1$-C$_6$)alkoxy, (C$_1$-C$_6$)alkanoyl, (C$_1$-C$_6$)alkanoyloxy, (C$_1$-C$_6$)alkoxycarbonyl, halo, cyano, nitro, carboxy, trifluoromethyl, trifluoromethoxy, —NR$_{a1}$R$_{b1}$, or —S(O)$_2$NR$_{c1}$R$_{d1}$;

each R$_{a1}$ and R$_{b1}$ is independently H, (C$_1$-C$_6$)alkyl, or aryl; or R$_{a1}$ and R$_{b1}$ together with the nitrogen to which they are attached form a pyrrolidino, piperidino, morpholino, or thiomorpholino ring;

each R$_{c1}$ and R$_{d1}$ is independently H, (C$_1$-C$_6$)alkyl, or aryl; or R$_{c1}$ and R$_{d1}$ together with the nitrogen to which they are attached form a pyrrolidino, piperidino, morpholino, or thiomorpholino ring;

each R$_m$ and R$_n$ is independently H, (C$_1$-C$_6$)alkyl, or aryl; or R$_m$ and R$_n$ together with the nitrogen to which they are attached form a pyrrolidino, piperidino, morpholino, or thiomorpholino ring;

each R$_p$ and R$_q$ is independently H, (C$_1$-C$_6$)alkyl, or aryl; or R$_p$ and R$_q$ together with the nitrogen to which they are attached form a pyrrolidino, piperidino, morpholino, or thiomorpholino ring; and wherein any aryl of R$_{a1}$, R$_{b1}$, R$_{c1}$, R$_{d1}$, R$_m$, R$_n$, R$_p$ or R$_q$ is optionally substituted with one or more (C$_1$-C$_6$)alkyl, (C$_1$-C$_6$)alkoxy, (C$_1$-C$_6$)alkanoyl, (C$_1$-C$_6$)alkanoyloxy, (C$_1$-C$_6$)alkoxycarbonyl, halo, cyano, nitro, carboxy, trifluoromethyl, trifluoromethoxy, —NR$_s$R$_t$, or —S(O)$_2$NR$_s$R$_t$ wherein each R$_s$ and R$_t$ is independently H or (C$_1$-C$_6$)alkyl;

or a pharmaceutically acceptable salt or prodrug thereof.

In one embodiment the invention provides a method to treat fibrosis (e.g., pulmonary fibrosis) in an animal (e.g., a mammal such as a human) comprising administering to the animal a compound of formula I:

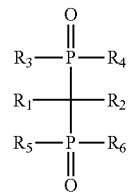

I wherein:

R$_1$ is a saturated or unsaturated (C$_5$-C$_{20}$)alkyl chain that optionally comprises one or more aryl rings in the chain and that is optionally substituted with one or more halo, trifluoromethyl, —OR$_a$, —P(=O)(OR$_a$)$_2$, or —NR$_b$R$_c$;

R$_2$ is a saturated or unsaturated (C$_5$-C$_{20}$)alkyl chain that optionally comprises one or more aryl rings in the chain and that is optionally substituted with one or more halo, trifluoromethyl, —OR$_a$, —P(=O)(OR$_a$)$_2$, or —NR$_b$R$_c$;

each R$_3$, R$_4$, R$_5$, and R$_6$ is independently OH or (C$_1$-C$_6$)alkoxy;

each R$_a$ is independently H, (C$_1$-C$_6$)alkyl, or aryl; and each $R_b$ and $R_c$ is independently H, $(C_1-C_6)$alkyl, or aryl; or $R_b$ and $R_c$ together with the nitrogen to which they are attached form a pyrrolidino, piperidino, morpholino, or thiomorpholino ring;

wherein any aryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $-NR_dR_e$, or $-S(O)_2NR_dR_e$, wherein each $R_d$ and $R_e$ is independently H or $(C_1-C_6)$alkyl;

or a pharmaceutically acceptable salt or prodrug thereof.

The invention also provides a method to modulate mitochondrial peroxide production in a cell comprising contacting the cell with a compound of formula I, formula II or formula III or a pharmaceutically acceptable salt or prodrug thereof.

The invention also provides a method to modulate the import of Rac1 into the mitochondria of a cell comprising contacting the cell with a compound of formula I, formula II or formula III as described herein, or a pharmaceutically acceptable salt or prodrug thereof.

The invention also provides a method to modulate mitochondrial peroxide production in a cell comprising contacting the cell with a compound of formula I as described herein or a pharmaceutically acceptable salt or prodrug thereof.

The invention also provides a method to modulate the import of Rac1 into the mitochondria of a cell comprising contacting the cell with a compound of formula I or a pharmaceutically acceptable salt or prodrug thereof as described herein.

The invention also provides a compound of formula I, formula II or formula III or a pharmaceutically acceptable salt or prodrug thereof as described herein, for the prophylactic or therapeutic treatment of fibrosis.

The invention also provides a compound of formula I, formula II or formula III or a pharmaceutically acceptable salt or prodrug thereof as described herein, for modulating mitochondrial peroxide production.

The invention also provides a compound of formula I, formula II or formula III or a pharmaceutically acceptable salt or prodrug thereof as described herein, for modulating the import of Rac1 into the mitochondria of a cell.

The invention also provides the use of a compound formula I, formula II or formula III or a pharmaceutically acceptable salt or prodrug thereof as described herein, to prepare a medicament useful for treating fibrosis in an animal (e.g., a mammal such as a human).

The invention also provides the use of a compound of formula I, formula II or formula III or a pharmaceutically acceptable salt or prodrug thereof as described herein, to prepare a medicament useful for modulating mitochondrial peroxide production.

The invention also provides the use of a compound of formula I, formula II or formula III or a pharmaceutically acceptable salt or prodrug thereof as described herein, to prepare a medicament useful for modulating the import of Rac1 into the mitochondria of a cell.

The invention also provides a compound of formula I, or a pharmaceutically acceptable salt or prodrug thereof as described herein, for the prophylactic or therapeutic treatment of fibrosis.

The invention also provides a compound of formula I, or a pharmaceutically acceptable salt or prodrug thereof as described herein for modulating mitochondrial peroxide production.

The invention also provides a compound of formula I, or a pharmaceutically acceptable salt or prodrug thereof as described herein for modulating the import of Rac1 into the mitochondria of a cell.

The invention also provides the use of a compound of formula I, or a pharmaceutically acceptable salt or prodrug thereof as described herein to prepare a medicament useful for treating fibrosis in an animal (e.g., a mammal such as a human).

The invention also provides the use of a compound of formula I, or a pharmaceutically acceptable salt or prodrug thereof as described herein to prepare a medicament useful for modulating mitochondrial peroxide production.

The invention also provides the use of a compound of formula I or a pharmaceutically acceptable salt or prodrug thereof as described herein, to prepare a medicament useful for modulating the import of Rac1 into the mitochondria of a cell.

Representative immunoblot is shown. (D) Normal subjects (n=8) and IPF patients (n=6). Rac1 activity was measured by G-LISA. *p<0.05

Figure 8:
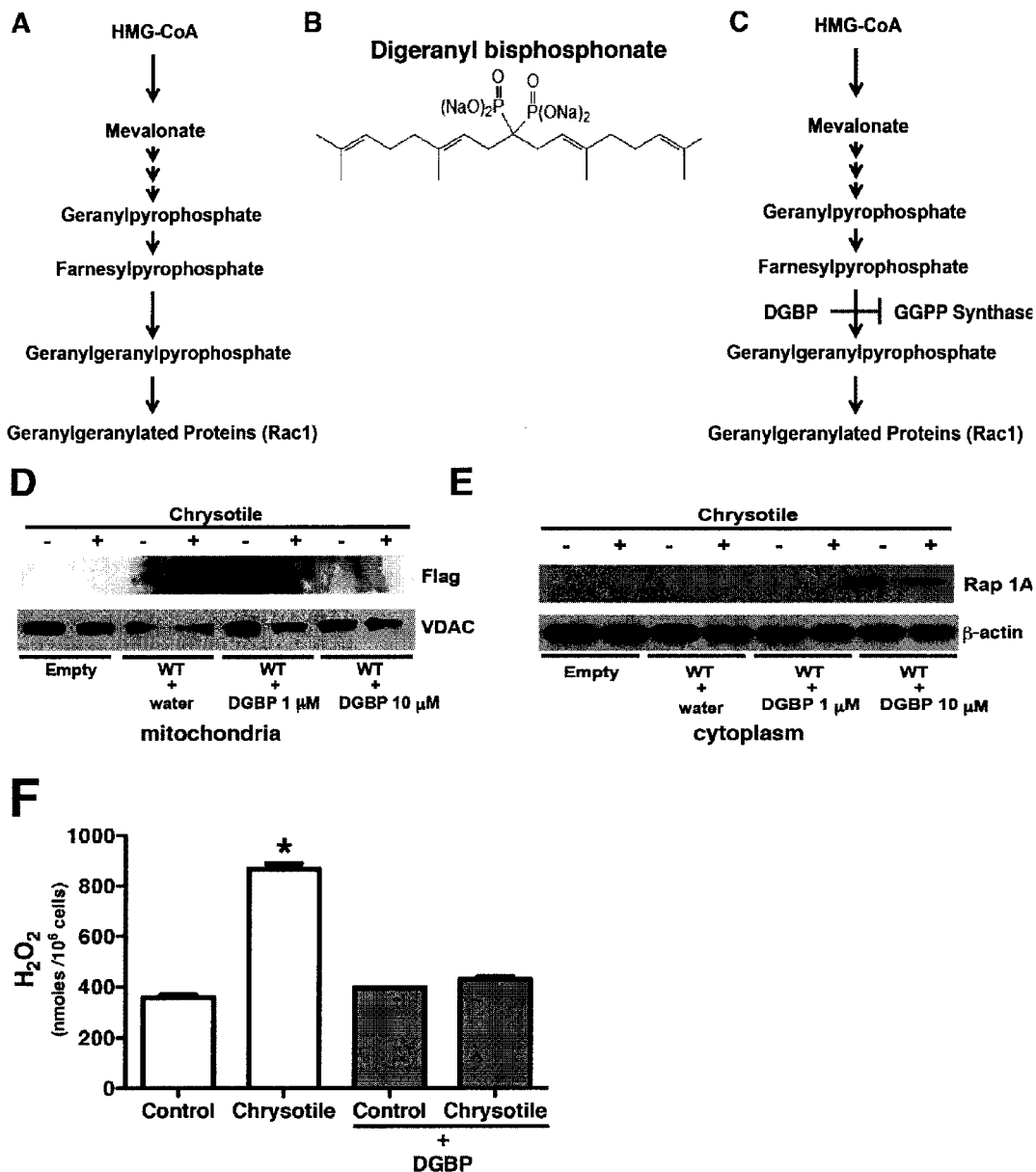

FIG. 8. Digeranyl bisphosphonate attenuates Rac1 mitochondrial import and mitochondrial $H_2O_2$ production. (A) Schematic flow diagram of the isoprenoid pathway. (B) chemical structure of digeranyl bisphosphonate (DGBP). (C) DGBP inhibits GGPP synthase. (D) Macrophages were transfected with empty or Flag-Rac1 (WT). Cells were cultured overnight with water or DGBP and exposed to chrysotile (10 μg/cm$^2$) for 90 min. Immunoblot analysis was performed for Flag or VDAC in isolated mitochondria. (E) Macrophages were transfected as in (A). Immunoblot analysis for Rap1A was performed in isolated cytoplasm. (F) Macrophages (n=5) were cultured in the presence or absence of DGBP overnight and exposed to chrysotile (10 μg/cm$^2$) for 90 mins. $H_2O_2$ was measured and is expressed in nmoles/10$^6$ cells *P<0.0001 vs. all other conditions.

Figure 9:
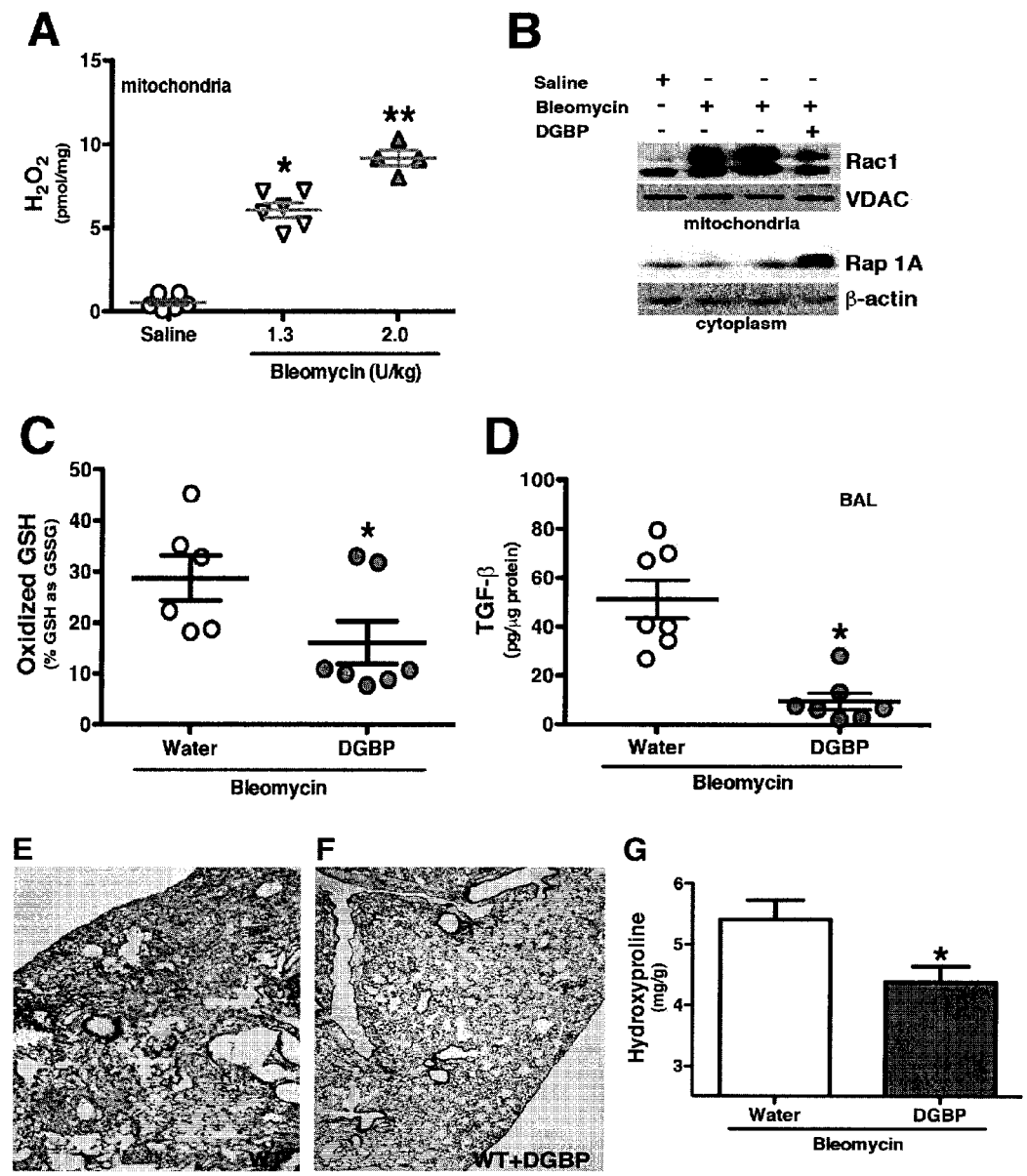

FIG. 9. (A) DGBP abrogates oxidative stress and development of bleomycin-induced pulmonary fibrosis. C57Bl/6 mice were administered saline (n=6) or bleomycin (1.3 (n=6) or 2.0 (n=4) U/kg) intratracheally. Alveolar macrophages were isolated 21 days later. Mitochondria were isolated, and $H_2O_2$ was measured by pHPA assay and is expressed in pmole/mg. *p<0.0001 vs. saline, ** p vs. 1.3 U/kg. (B) Osmotic pumps containing vehicle (water) or DGBP were implanted subcutaneously. DGBP was administered at 0.2 mg/kg/day. Saline or bleomycin (2.0 U/kg) was administered intratracheally. Alveolar macrophages were obtained 21 days later. An immunoblot analysis was performed for Rac1 in isolated mitochondria and for Rap1A in cytoplasm. (C) Lungs were extracted and homogenized for glutathione assay. Total GSH in disulfide form was expressed as % GSSG. * p<0.032 water (n=6) vs. DGBP (n=7). (D) Active TGF-β in BAL fluid was measured by ELISA. p<0.0002 water (n=7 vs. DGBP (n=7). (E) and (F) Lungs were extracted and processed for Masson's trichrome staining. Micrographs are representative of (E) 15 water and (F) 15 DGBP. (G) Lungs were homogenized for hydroxyproline assay and this is expressed in mg/g. *p<0.0125 water (n=7) vs. DGBP (n=8).

Figure 10:
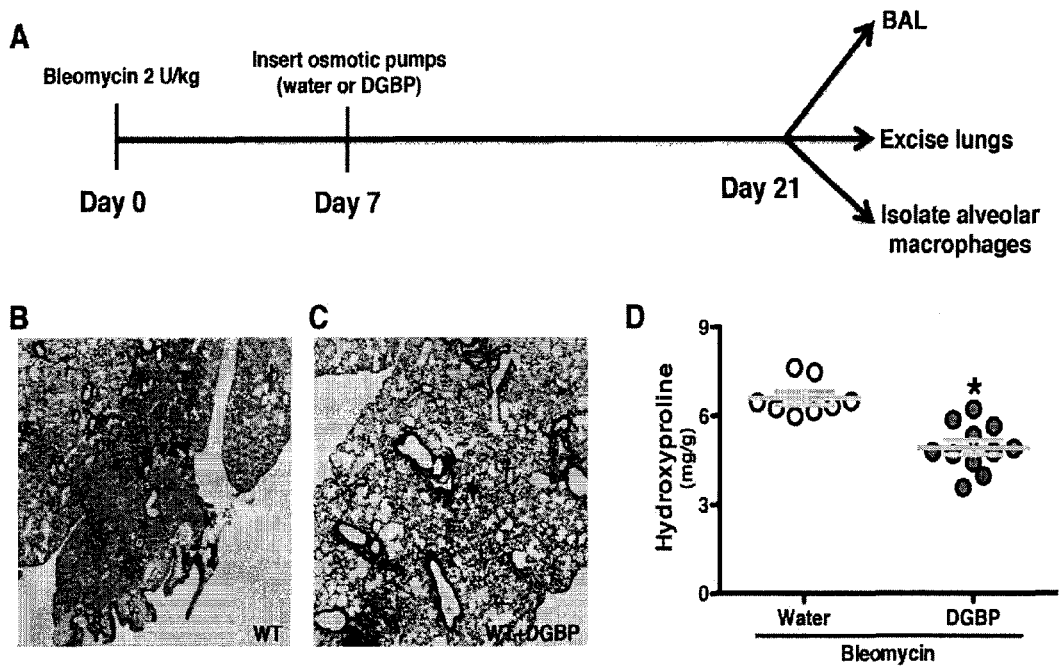

FIG. 10. DGBP attenuates progression of bleomycin-induced pulmonary fibrosis. (A) Schematic diagram of experimental design. C57Bl/6 mice were administered bleomycin (2.0 U/kg) intratracheally. Osmotic pumps containing water or DGBP were implanted subcutaneously seven days later. DGBP was delivered at 0.2 mg/kg/day. Mice euthanized 21 days after bleomycin. Lungs were removed and processed for Masson's trichrome staining. Micrographs are representative of (B) 8 water and (C) 11 DGBP treated animals. (D) Lungs were homogenized for hydroxyproline assay. p<0.05 water (n=8) vs. DGBP (n=11).

FIG. 11. DGBP abrogates oxidative stress and development of chrysotile-induced pulmonary fibrosis. Osmotic pumps containing water or DGBP were implanted subcutaneously in C57Bl/6 WT mice. Mice were exposed to saline or chrysotile (100 μg/50 ml NS) intratracheally. After 21 days, (A) alveolar macrophages were isolated by BAL. An immunoblot analysis for Rac1 was performed in isolated mitochondria. (B) Lungs were extracted and homogenized in 5-sulfosalicylic acid for glutathione assay. Total GSH in disulfide form was expressed as % GSSG. p<0.0210 water (n=5) vs. DGBP (n=4). Lungs were removed and processed for Masson's trichrome staining. Micrographs are representative of (C) water (n=8) and (D) DGBP (n=6). (E) Lungs were extracted and homogenized for hydroxyproline assay. * p<0.0253 water (n=7) vs. DGBP (n=6). (F) THP-1, (G) MLE-12, and (H) HLF-1 cells were cultured in the presence or absence of DGBP (10 μM) overnight. Cells were exposed to chrysotile (10 μg/cm$^2$) for 1 h. $H_2O_2$ production was measured by pHPA assay in isolated mitochondria. (F)* p<0.0001 chrysotile vs. all other conditions; (G)* p<0.0001 chrysotile (160-200 min) vs. chrysotile+DGBP (160-200 min); (H)* p<0.0001 control vs. chrysotile (160-200 min); ** p<0.0001 chrysotile vs. chrysotile+DGBP (120-200 min). n=3 for all conditions.

DETAILED DESCRIPTION

The following definitions are used, unless otherwise described: halo is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic.

Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X) in which at least one ring that comprises at least one heteroatom is aromatic.

As used herein, a saturated or unsaturated $(C_1-C_{20})$alkyl chain that comprises one or more aryl or heteroaryl rings in the chain, and a saturated or unsaturated $(C_5-C_{20})$alkyl chain that comprises one or more aryl or heteroaryl rings in the chain, each include: 1) alkyl chains that have an aryl or heteroaryl within the chain so as to have one portion of the alkyl chain attached to one atom of the aryl or heteroaryl and another portion of the alkyl chain attached to a different atom of the aryl or heteroaryl and 2) alkyl chains that are terminated with an aryl or heteroaryl.

In one embodiment of the invention, the saturated or unsaturated $(C_5-C_{20})$alkyl chain that comprises one or more aryl or heteroaryl rings in the chain of $R_7$, includes the aryl or heteroaryl within the chain so as to have one portion of the alkyl chain attached to one atom of the aryl or heteroaryl and another portion of the alkyl chain attached to a different atom of the aryl or heteroaryl.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). An amino acid can be linked to the remainder of a compound of formula I through the carboxy terminus, the amino terminus, or through any other convenient point of attachment, such as, for example, through the sulfur of a cysteine. In one embodiment of the invention, when an amino acid is linked to a phosphorous in a compound of formula I, the amino acid is linked through the amino terminus or through another nitrogen of the amino acid.

Fibrosis typically involves the formation of excess fibrous connective tissue during a reactive process, such as response to injury that is not part of the normal development of the organ or tissue. The term includes, for example, pulmonary fibrosis and fibrosis of the liver (i.e., liver fibrosis), as well as other tissues.

The term "treat", "treatment" or "treating," to the extent it relates to a disease or condition includes preventing the disease or condition from occurring, inhibiting the disease or condition, eliminating the disease or condition, and/or relieving one or more symptoms of the disease or condition.

The term "prodrug" is well understood in the art and includes compounds that are converted to pharmaceutically active compounds in vivo (e.g. in an animal such as a mammal). For example, see Remington's Pharmaceutical Sciences, 1980, vol. 16, Mack Publishing Company, Easton, Pa., 61 and 424. In particular, a number of groups suitable for preparing prodrug forms of phosphorous containing compounds (e.g., phosphonates) are known. For example, see Galmarini C M, et al., International Journal of Cancer, 2003, 107 (1), 149-154; Wagner, C. R., et al., Medicinal Research Reviews, 2000, 20, 417-51; McGuigan, C., et al., Antiviral Research, 1992, 17, 311-321; and Chapman, H., et al., Nucleosides, Nucleotides & Nucleic Acids, 2001, 20, 1085-1090 and Wiemer, et al., Bioorg. Med. Chem. 2008, 16(7), p. 3652-3660. The invention includes phosphonate prodrug analogs prepared from suitable in vivo hydrolysable groups.

Methods involving contacting a cell include contacting in vitro and in vivo (e.g., a cell in an animal such as a mammal including a human).

It will be appreciated by those skilled in the art that compounds of formula I having a chiral center may exist in and be isolated in optically active and racemic forms. For example, it is possible for one or both phosphorous atoms in a compound of formula I to be chiral centers. Some compounds may exhibit polymorphism. It is to be understood that the compounds of formula I can encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine enzyme inhibitory activity using the standard tests that are well known in the art.

Specific and preferred values listed below for radicals, substituents, and ranges, are for illustration only; they do not exclude other defined values or other values within defined ranges for the radicals and substituents. The specific values are values for formulas I, II and III and all subformulas (e.g., formulas IIa, IIIa) which compounds are useful in the methods of the invention. One or more values may be combined.

Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, iso-propoxy, butoxy, iso-butoxy, sec-butoxy, pentoxy, 3-pentoxy, or hexyloxy; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_2-C_6)$alkanoyloxy can be acetoxy, propanoyloxy, butanoyloxy, isobutanoyloxy, pentanoyloxy, or hexanoyloxy; and aryl can be phenyl, indenyl, or naphthyl. Heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R_1$ is a saturated or unsaturated $(C_5-C_{20})$alkyl chain.

Another specific value for $R_1$ is an unsaturated $(C_5-C_{20})$alkyl chain.

Another specific value for $R_1$ is a saturated or unsaturated $(C_5-C_{20})$alkyl chain that comprises one or more aryl rings in the chain.

Another specific value for $R_1$ is a saturated or unsaturated $(C_5-C_{20})$alkyl chain that is substituted with one or more halo, trifluoromethyl, $OR_a$ or $NR_bR_c$.

Another specific value for $R_1$ is the formula,

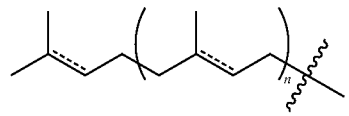

wherein n is 0, 1, 2, or 3; and each bond designated by ----- is independently either present or is absent.

A specific value for n is 0.
Another specific value for n is 1.
Another specific value for n is 2.
Another specific value for n is 3.
Another specific value for $R_1$ is the formula,

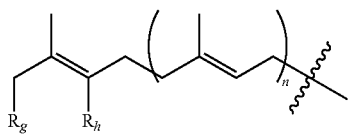

wherein:

n is 0, 1, 2, or 3; and $R_g$ and $R_h$ together with the atoms to which they are attached form an aryl ring that is optionally substituted with one or more (e.g. 1, 2, 3, or 4) $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl.

Another specific value for $R_1$ is the formula,

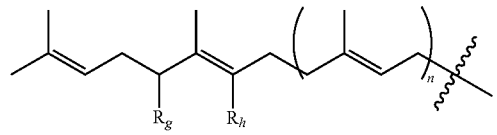

wherein:

n is 0, 1, or 2; and $R_g$ and $R_h$ together with the atoms to which they are attached form an aryl ring that is optionally substituted with one or more (e.g. 1, 2, 3, or 4) $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl.

Another specific value for $R_1$ is of the formula,

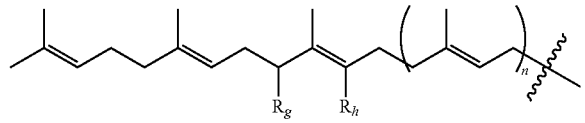

wherein:
n is 0 or 1; and
$R_g$ and $R_h$ together with the atoms to which they are attached form an aryl ring that is optionally substituted with one or more (e.g. 1, 2, 3, or 4) $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl.

Another specific value for $R_1$ is the formula,

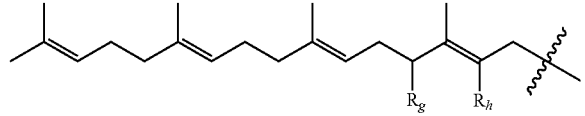

wherein:
$R_g$ and $R_h$ together with the atoms to which they are attached form an aryl ring that is optionally substituted with one or more (e.g. 1, 2, 3, or 4) $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl.

Another specific value for $R_1$ is a saturated or unsaturated $(C_5-C_{20})$alkyl chain terminally substituted with $OR_a$ or $NR_dR_e$; wherein $R_a$ is aryl; and each $R_b$ and $R_c$ is independently H, $(C_1-C_6)$alkyl, or aryl; wherein any aryl is optionally substituted with one or more carboxy or $S(O)_2NR_dR_e$, wherein each $R_d$ and $R_e$ is independently H or $(C_1-C_6)$alkyl.

Another specific value for $R_1$ is the formula,

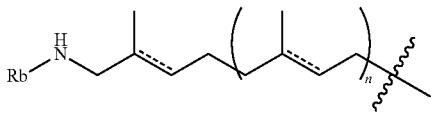

wherein:
n is 0, 1, 2, or 3;
each bond designated by ----- is independently either present or is absent; and
$R_b$ is phenyl or naphthyl and is optionally substituted with one or more carboxy or $S(O)_2NR_dR_e$, wherein each $R_d$ and $R_e$ is independently H or $(C_1-C_6)$alkyl.

A specific value for $R_2$ is a saturated or unsaturated $(C_5-C_{20})$alkyl chain.

Another specific value for $R_2$ is an unsaturated $(C_5-C_{20})$alkyl chain.

Another specific value for $R_2$ is a saturated or unsaturated $(C_5-C_{20})$alkyl chain that comprises one or more aryl rings in the chain.

Another specific value for $R_2$ is a saturated or unsaturated $(C_5-C_{20})$alkyl chain that is substituted with one or more halo, trifluoromethyl, $OR_a$ or $NR_bR_c$.

Another specific value for $R_2$ is the formula,

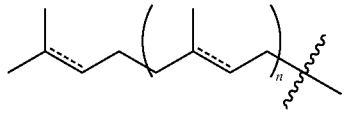

wherein:
n is 0, 1, 2, or 3; and each bond designated by ----- is independently either present or is absent.

Another specific value for $R_2$ is the formula,

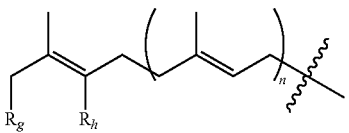

wherein:
n is 0, 1, 2, or 3; and
$R_g$ and $R_h$ together with the atoms to which they are attached form an aryl ring that is optionally substituted with one or more (e.g. 1, 2, 3, or 4) $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl.

Another specific value for $R_2$ is the formula,

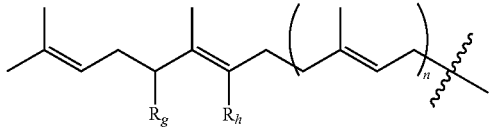

wherein:
n is 0, 1, or 2; and
$R_g$ and $R_h$ together with the atoms to which they are attached form an aryl ring that is optionally substituted with one or more (e.g. 1, 2, 3, or 4) $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl.

Another specific value for $R_2$ is the formula,

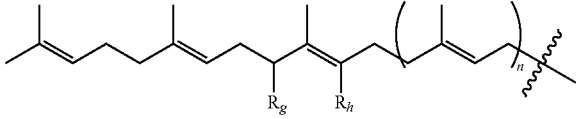

wherein:
n is 0 or 1; and
$R_g$ and $R_h$ together with the atoms to which they are attached form an aryl ring that is optionally substituted with one or more (e.g. 1, 2, 3, or 4) $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl.

Another specific value for $R_2$ is the formula,

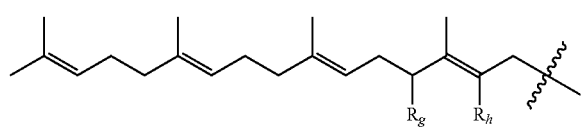

wherein:

$R_g$ and $R_h$ together with the atoms to which they are attached form an aryl ring that is optionally substituted with one or more (e.g. 1, 2, 3, or 4) $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl.

Another specific value for $R_2$ is a saturated or unsaturated $(C_5-C_{20})$alkyl chain terminally substituted with $OR_a$ or $NR_bR_c$; wherein $R_a$ is aryl; and each $R_b$ and $R_c$ is independently H, $(C_1-C_6)$alkyl, or aryl; wherein any aryl is optionally substituted with one or more carboxy or $S(O)_2NR_dR_e$, wherein each $R_d$ and $R_e$ is independently H or $(C_1-C_6)$alkyl.

Another specific value for $R_2$ is of the formula,

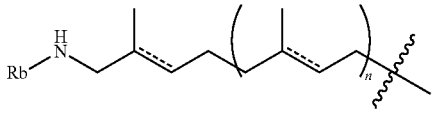

wherein:

n is 0, 1, 2, or 3;

each bond designated by ----- is independently either present or is absent; and $R_b$ is phenyl or naphthyl and is optionally substituted with one or more carboxy or $S(O)_2NR_dR_e$, wherein each $R_d$ and $R_e$ is independently H or $(C_1-C_6)$alkyl.

A specific value for each of $R_3$, $R_4$, $R_5$, and $R_6$ is OH.

Another specific value for each $R_3$, $R_4$, $R_5$, and $R_6$ is $(C_1-C_6)$alkoxy;

A specific compound is a prodrug of a compound wherein each $R_3$, $R_4$, $R_5$, and $R_6$ is OH.

Another specific compound is a prodrug wherein one or more of $R_3$, $R_4$, $R_5$, and $R_6$ is a group that is cleaved in vivo to provide a corresponding compound wherein said one or more of $R_3$, $R_4$, $R_5$, and $R_6$ is OH.

Another specific value for $R_3$, $R_4$, $R_5$, and/or $R_6$ is a pivaloyloxymethyloxy, s-acyl-2-thioethyloxy, or an amino acid.

In one embodiment of the invention the compound of formula I is digeranyl bisphosphonate, or a pharmaceutically acceptable salt or prodrug thereof.

In one embodiment of the invention the compound of formula I is: ((6E,11E)-2,6,12,16-tetramethylheptadeca-2,6,11,15-tetraene-9,9-diyl)diphosphonic acid, or a pharmaceutically acceptable salt or prodrug thereof.

In one embodiment of the invention the compound of formula I is:

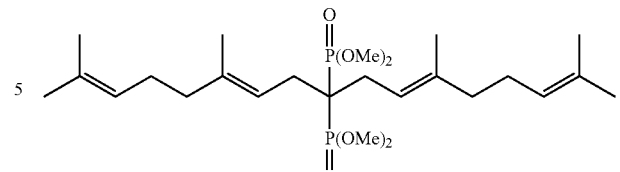

tetramethyl (E)-1,1-bis(4,8-dimethyl-nona-3,7-dienyl)-1,1-bisphosphonate,

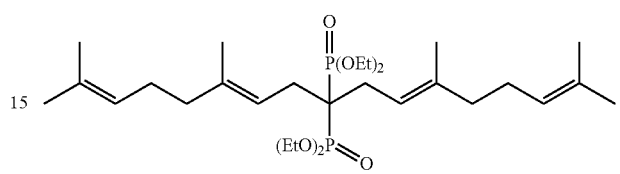

6 tetraethyl 4,8-dimethyl-3,7-nonadienyl-1,1-bisphosphonate (6),

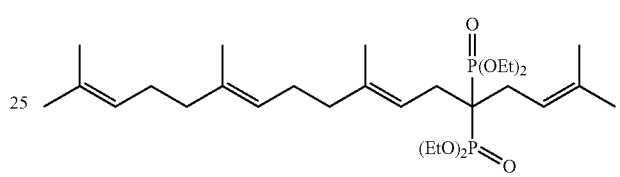

11 tetraethyl (2E,6E)-1-(3-methyl-but-2-enyl)-3,7,11-trimethyl-dodeca-2,6,10-trienyl-1,1-bisphosphonate (11),

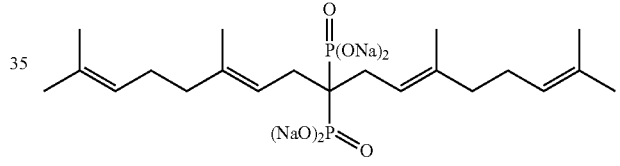

12

1-(3,7-dimethyl-octa-2,6-dienyl)-4,8-dimethyl-nona-3,7-dienyl-1,1-bisphosphonic acid, tetrasodium salt (12),

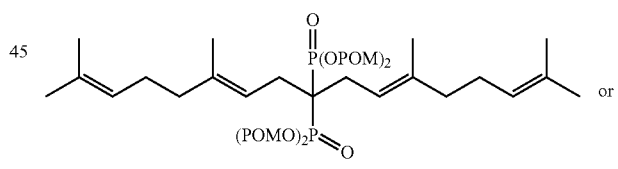

13 tetrapivaloyloxymethyl (E)-1,1-bis(4,8-dimethyl-nona-3,7-dienyl)-1,1-bisphosphonate (13),

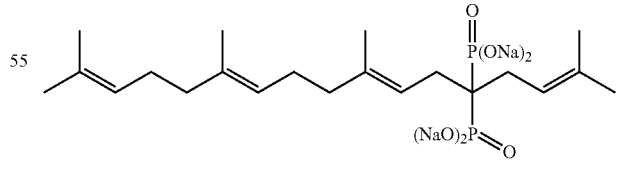

14

(2E,6E)-1-(3-methyl-but-2-enyl)-3,7,11-trimethyl-dodeca-2,6,10-triene-1,1-bisphosphonate (14), or a pharmaceutically acceptable salt or prodrug thereof.

Also provided is a compound of formula IIa or formula IIIa for use in the methods of the invention:

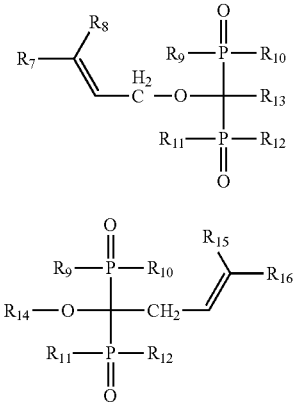

wherein:

$R_7$ is H or a saturated or unsaturated $(C_1-C_{20})$alkyl chain that optionally comprises one or more aryl or heteroaryl rings in the chain wherein $(C_5-C_{20})$alkyl is optionally substituted with one or more halo cyano, nitro, carboxy, trifluoromethyl, trifluoromethoxy, aryl, heteroaryl, $NR_mR_n$, or $S(O)_2NR_pR_q$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_{a1}R_{b1}$, or $S(O)_2NR_{c1}R_{d1}$;

$R_8$ is H or a saturated or unsaturated $(C_1-C_{20})$alkyl chain that optionally comprises one or more aryl or heteroaryl rings in the chain wherein $(C_5-C_{20})$alkyl is optionally substituted with one or more halo cyano, nitro, carboxy, trifluoromethyl, trifluoromethoxy, aryl, heteroaryl, $NR_mR_n$, or $S(O)_2NR_pR_q$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_{a1}R_{b1}$, or $S(O)_2NR_{c1}R_{d1}$;

each $R_9$, $R_{10}$, $R_{11}$, and $R_{12}$ is independently OH or $(C_1-C_6)$ alkoxy;

$R_{13}$ is a saturated or unsaturated $(C_1-C_{20})$alkyl chain that optionally comprises one or more aryl or heteroaryl rings in the chain wherein $(C_5-C_{20})$alkyl is optionally substituted with one or more halo cyano, nitro, carboxy, trifluoromethyl, trifluoromethoxy, aryl, heteroaryl, $NR_mR_n$, or $S(O)_2NR_pR_q$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_{a1}R_{b1}$, or $S(O)_2NR_{c1}R_{d1}$;

$R_{14}$ is a saturated or unsaturated $(C_1-C_{20})$alkyl chain that optionally comprises one or more aryl or heteroaryl rings in the chain wherein $(C_5-C_{20})$alkyl is optionally substituted with one or more halo cyano, nitro, carboxy, trifluoromethyl, trifluoromethoxy, aryl, heteroaryl, $NR_mR_n$, or $S(O)_2NR_pR_q$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_{a1}R_{b1}$, or $S(O)_2NR_{c1}R_{d1}$;

$R_{15}$ is H or a saturated or unsaturated $(C_1-C_{20})$alkyl chain that optionally comprises one or more aryl or heteroaryl rings in the chain wherein $(C_5-C_{20})$alkyl is optionally substituted with one or more halo cyano, nitro, carboxy, trifluoromethyl, trifluoromethoxy, aryl, heteroaryl, $NR_mR_n$, or $S(O)_2NR_pR_q$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_{a1}R_{b1}$, or $S(O)_2NR_{c1}R_{d1}$;

$R_{16}$ is H or a saturated or unsaturated $(C_1-C_{20})$alkyl chain that optionally comprises one or more aryl or heteroaryl rings in the chain wherein $(C_5-C_{20})$alkyl is optionally substituted with one or more halo cyano, nitro, carboxy, trifluoromethyl, trifluoromethoxy, aryl, heteroaryl, $NR_mR_n$, or $S(O)_2NR_pR_q$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_{a1}R_{b1}$, or $S(O)_2NR_{c1}R_{d1}$;

each $R_{a1}$ and $R_{b1}$ is independently H, $(C_1-C_6)$alkyl, or aryl; or $R_{a1}$ and $R_{b1}$ together with the nitrogen to which they are attached form a pyrrolidino, piperidino, morpholino, or thiomorpholino ring;

each $R_{c1}$ and $R_{d1}$ is independently H, $(C_1-C_6)$alkyl, or aryl; or $R_{c1}$ and $R_{d1}$ together with the nitrogen to which they are attached form a pyrrolidino, piperidino, morpholino, or thiomorpholino ring;

each $R_m$ and $R_n$ is independently H, $(C_1-C_6)$alkyl, or aryl; or $R_m$ and $R_n$ together with the nitrogen to which they are attached form a pyrrolidino, piperidino, morpholino, or thiomorpholino ring;

each $R_p$ and $R_q$ is independently H, $(C_1-C_6)$alkyl, or aryl; or $R_p$ and $R_q$ together with the nitrogen to which they are attached form a pyrrolidino, piperidino, morpholino, or thiomorpholino ring; and wherein any aryl of $R_{a1}$, $R_{b1}$; $R_{c1}$; $R_{d1}$; $R_m$, $R_n$, $R_p$ or $R_q$ is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$ alkoxycarbonyl, halo, cyano, nitro, carboxy, trifluoromethyl, trifluoromethoxy, $NR_sR_t$, or $S(O)_2NR_sR_t$ wherein each $R_s$ and $R_t$ is independently H or $(C_1-C_6)$alkyl;

or a salt thereof.

A specific compound is a compound of formula II, or a pharmaceutically acceptable salt or prodrug thereof.

A specific compound is a compound of formula IIa, or a pharmaceutically acceptable salt or prodrug thereof.

A specific value for X is —$(CH_2)_m$— or —$(CH_2)_m CH(CH_3)$— and m is an integer from 1 to 2.

Another specific value for X is —$(CH_2)_m$ or —$(CH_2)_m CH(CH_3)$— and m is 1.

Another specific value for X is —$(CH_2)_m$— or —$(CH_2)_m CH(CH_3)$— and m is 2.

Another specific value for X is —$(CH_2)_m$— or —$(CH_2)_m CH(CH_3)(CH_2)_m$— and m is an integer from 1 to 2.

Another specific value for X is —$(CH_2)$— or —$(CH_2)_2 CH(CH_3)(CH_2)_2$— and m is an integer from 1 to 2.

Another specific value for X is —$(CH_2)$— or

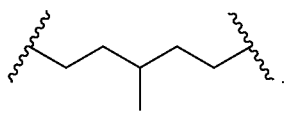 [SMILES: *CCC(C)CC*]

.

A specific value for $R_7$ is an unsaturated $(C_5-C_{20})$alkyl chain.

Another specific value for $R_7$ is an unsaturated $(C_5-C_{15})$ alkyl chain.

Another specific value for $R_7$ is
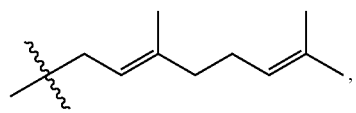
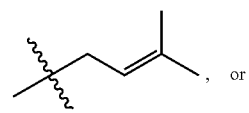, or
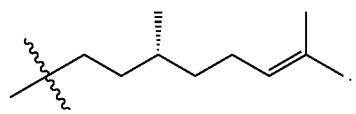
Another specific value for $R_7$ is a saturated or unsaturated $(C_1-C_{20})$alkyl chain that comprises one or more aryl rings in the chain.
Another specific value for $R_7$ is
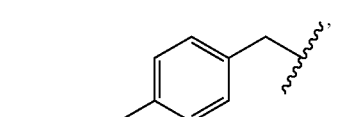
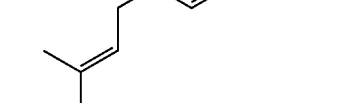
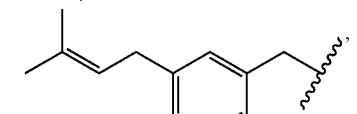
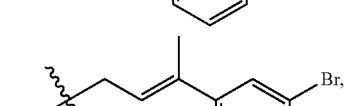
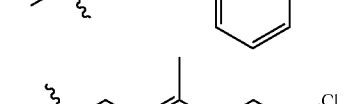
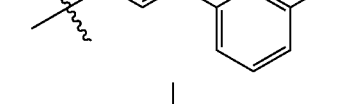
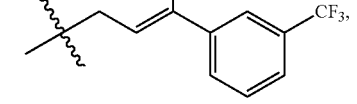
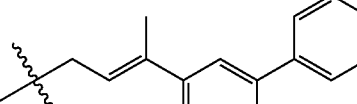
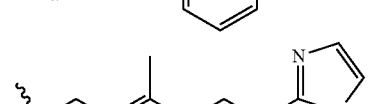
-continued
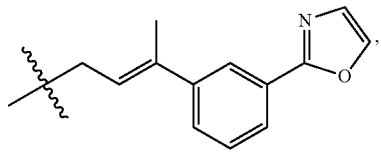
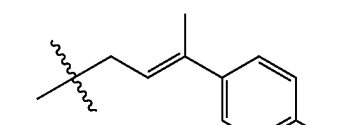
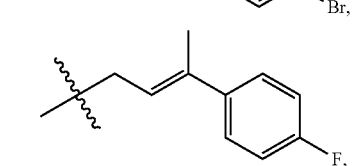
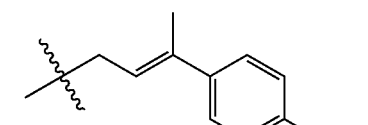
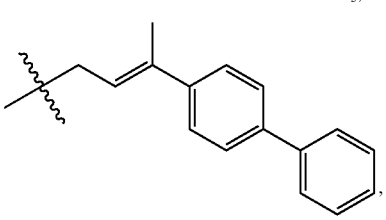
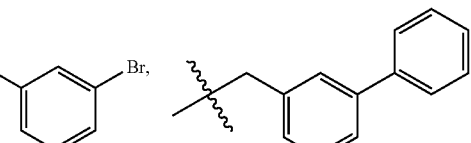
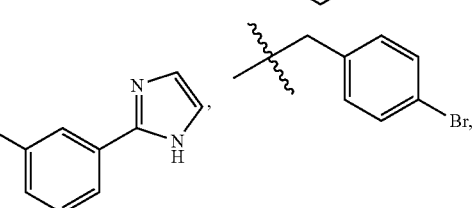
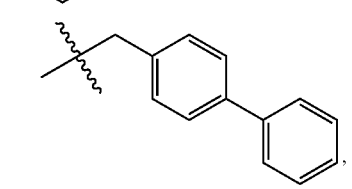
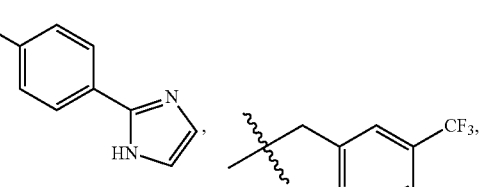
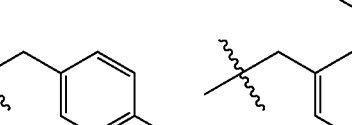
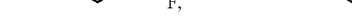

-continued

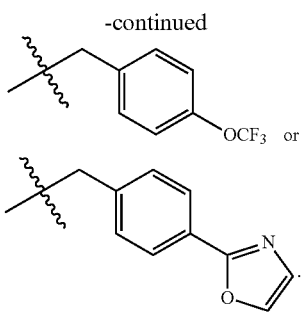

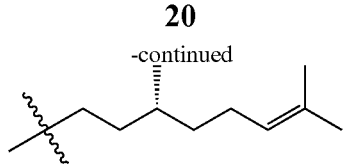

Another specific value for $R_{13}$ is a saturated or unsaturated $(C_1-C_{20})$alkyl chain that comprises one or more aryl or heteroaryl rings in the chain.

Another specific value for $R_{13}$ is

Another specific value for $R_7$ is a unsaturated $(C_5-C_{20})$ alkyl chain that comprises a heteroaryl ring in the chain.

Another specific value for $R_7$ is a unsaturated $(C_5-C_{20})$ alkyl chain that comprises a heteroaryl ring in the chain wherein the heteroaryl ring is indolyl.

Another specific value for $R_7$ is

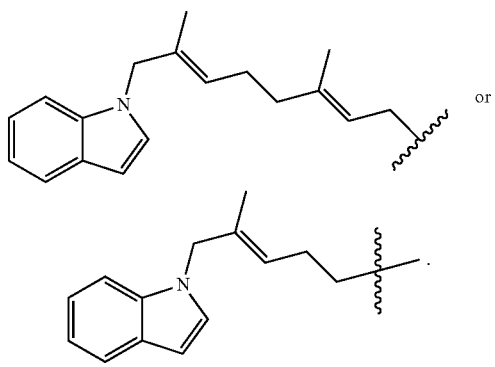

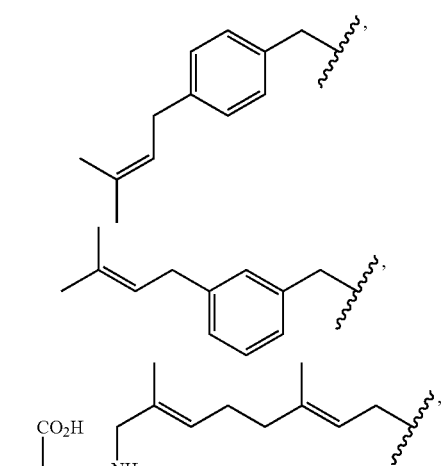

Another specific value for $R_7$ is a saturated or unsaturated $(C_1-C_{15})$alkyl chain.

Another specific value for $R_7$ is a saturated or unsaturated $(C_1-C_{10})$alkyl chain.

Another specific value for $R_7$ is methyl or

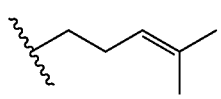

A specific value for $R_8$ is H or methyl.

Another specific value for $R_8$ is methyl.

A specific value for $R_{13}$ is a saturated or unsaturated $(C_1-C_{20})$alkyl chain.

Another specific value for $R_{13}$ is

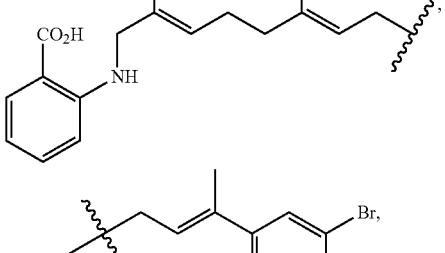

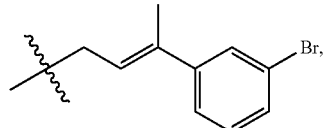

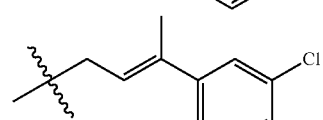

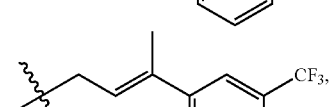

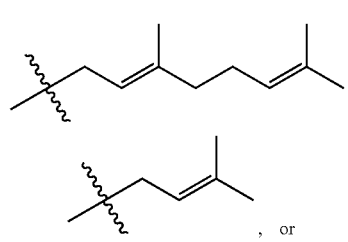

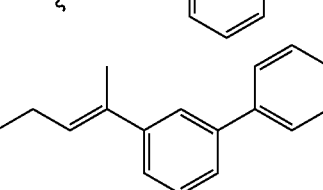

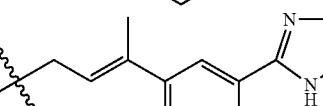

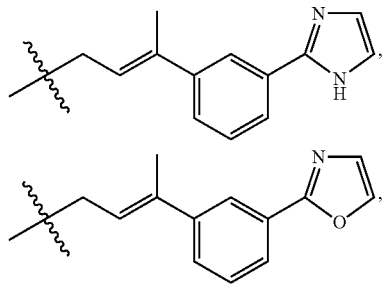

-continued

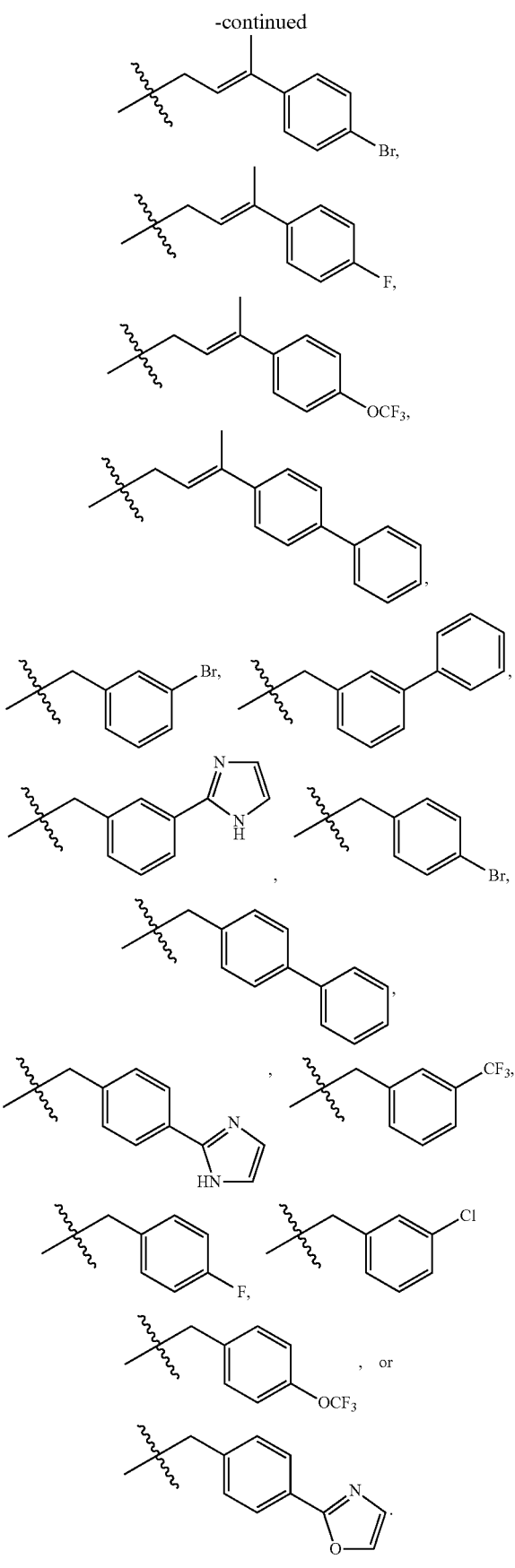

Another specific value for $R_{13}$ is a saturated $(C_1-C_3)$alkyl chain that comprises one or more aryl or heteroaryl rings in the chain, wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_{a1}R_{b1}$, aryl, heteroaryl, or $S(O)_2NR_{c1}R_{d1}$.

Another specific value for $R_{13}$ is a saturated or unsaturated $(C_1-C_5)$alkyl chain that comprises one or more aryl or heteroaryl rings in the chain, wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_{a1}R_{b1}$, aryl, heteroaryl, or $S(O)_2NR_{c1}R_{d1}$.

Another specific value for $R_{13}$ is a saturated or unsaturated $(C_1-C_{15})$alkyl chain that optionally comprises one or more aryl or heteroaryl rings in the chain wherein $(C_1-C_{15})$alkyl is optionally substituted with one or more halo, cyano, nitro, carboxy, trifluoromethyl, trifluoromethoxy, aryl, heteroaryl, —$NR_mR_n$, or —$S(O)_2NR_pR_q$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, —$NR_{a1}R_{b1}$, aryl, heteroaryl, or —$S(O)_2NR_{c1}R_{d1}$.

Another specific value for $R_{13}$ is

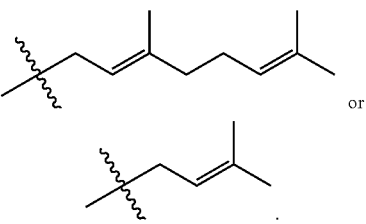

or

Another specific value for $R_{13}$ is

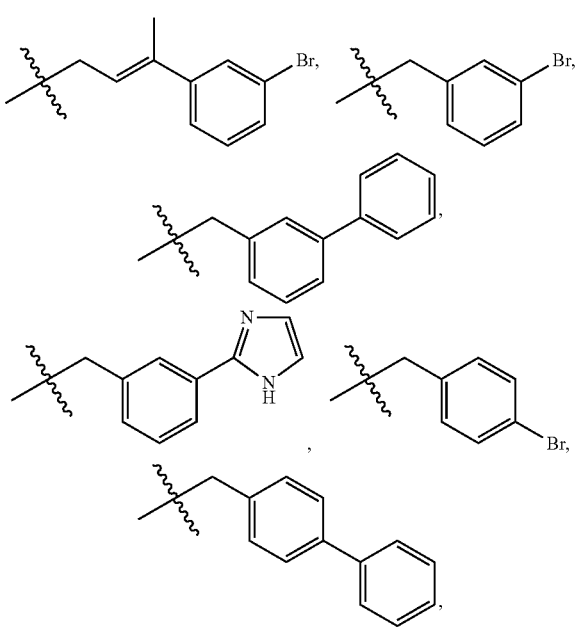

23

-continued

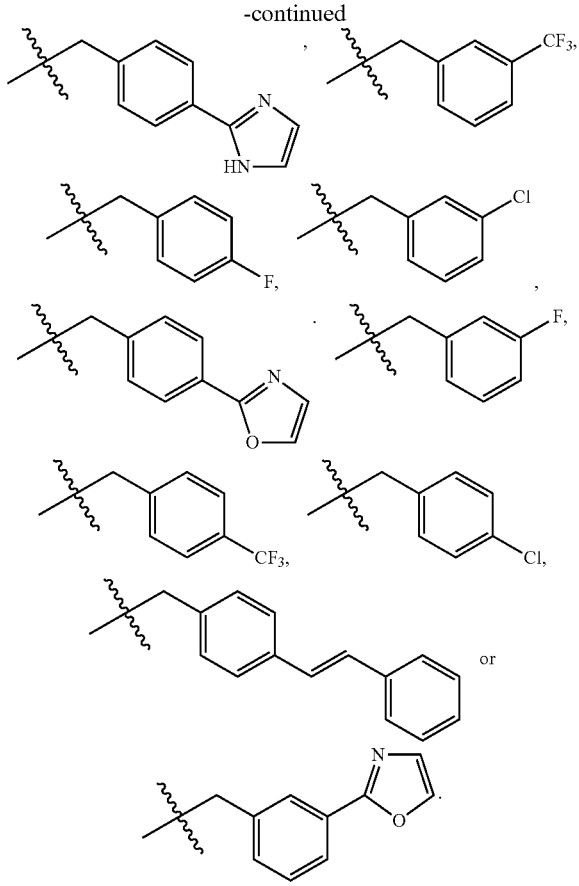

A specific compound of the invention is a compound of formula III, or a pharmaceutically acceptable salt or prodrug thereof.

A specific compound of the invention is a compound of formula IIIa, or a pharmaceutically acceptable salt or prodrug thereof.

A specific value for Y is —(CH$_2$)$_n$— or —(CH$_2$)$_n$CH(CH$_3$)— and n is an integer from 1 to 2.

Another specific value for Y is —(CH$_2$)$_n$— or —(CH$_2$)$_n$CH(CH$_3$)— and n is 1.

Another specific value for Y is —(CH$_2$)$_n$— or —(CH$_2$)$_n$CH(CH$_3$)— and n is 2.

Another specific value for Y is —(CH$_2$)—.

A specific value for R$_{14}$ is a saturated or unsaturated (C$_1$-C$_{20}$)alkyl chain that is optionally substituted with one or more halo, cyano, nitro, carboxy, trifluoromethyl, trifluoromethoxy, aryl, heteroaryl, NR$_m$R$_n$, or S(O)$_2$NR$_p$R$_q$.

Another specific value for R$_{14}$ is an unsaturated (C$_2$-C$_{20}$) alkyl chain that is optionally substituted with one or more halo, cyano, nitro, carboxy, trifluoromethyl, trifluoromethoxy, aryl, heteroaryl, NR$_m$R$_n$, or S(O)$_2$NR$_p$R$_q$ and wherein any aryl or heteroaryl is optionally substituted with one or more (C$_1$-C$_6$)alkyl, (C$_1$-C$_6$)alkoxy, (C$_1$-C$_6$)alkanoyl, (C$_1$-C$_6$)alkanoyloxy, (C$_1$-C$_6$)alkoxycarbonyl, halo, cyano, nitro, carboxy, trifluoromethyl, trifluoromethoxy, NR$_{a1}$R$_{b1}$, or S(O)$_2$NR$_{c1}$R$_{d1}$.

Another specific value for R$_{14}$ is an unsaturated (C$_2$-C$_{20}$) alkyl chain.

24

Another specific value for R$_{14}$ is

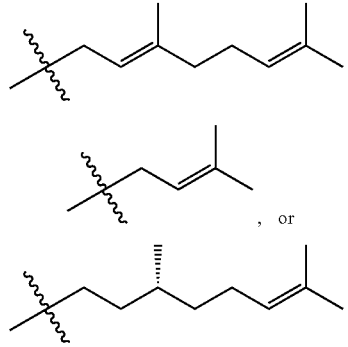

Another specific value for R$_{14}$ is a saturated (C$_1$-C$_{20}$)alkyl chain that comprises one or more aryl or heteroaryl rings in the chain wherein (C$_1$-C$_{20}$)alkyl is optionally substituted with one or more halo, cyano, nitro, carboxy, trifluoromethyl, trifluoromethoxy, aryl, heteroaryl, NR$_m$R$_n$, or S(O)$_2$NR$_p$R$_q$ and wherein any aryl or heteroaryl is optionally substituted with one or more (C$_1$-C$_6$)alkyl, (C$_1$-C$_6$)alkoxy, (C$_1$-C$_6$)alkanoyl, (C$_1$-C$_6$)alkanoyloxy, (C$_1$-C$_6$)alkoxycarbonyl, halo, cyano, nitro, carboxy, trifluoromethyl, trifluoromethoxy, NR$_{a1}$R$_{b1}$, or S(O)$_2$NR$_{c1}$R$_{d1}$.

Another specific value for R$_{14}$ is

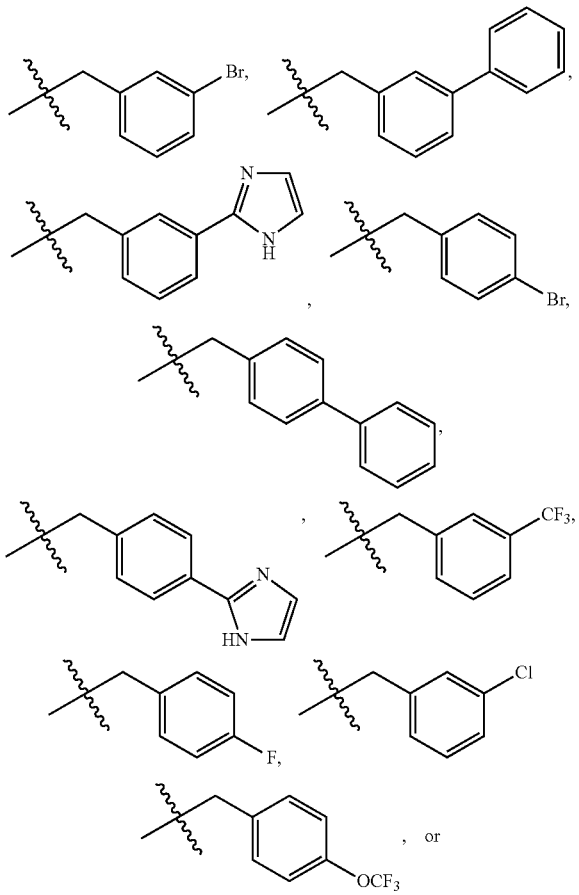

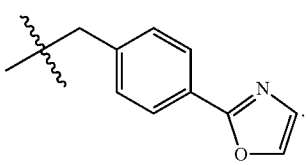

Another specific value for $R_{14}$ is a saturated $(C_1\text{-}C_{20})$alkyl chain.

Another specific value for $R_{14}$ is an unsaturated $(C_1\text{-}C_{20})$ alkyl chain that comprises one or more aryl or heteroaryl rings in the chain wherein $(C_1\text{-}C_{20})$alkyl is optionally substituted with one or more halo, cyano, nitro, carboxy, trifluoromethyl, trifluoromethoxy, aryl, heteroaryl, $NR_mR_n$, or $S(O)_2NR_pR_{c1}$ and wherein any aryl or heteroaryl is optionally substituted with one or more $(C_1\text{-}C_6)$alkyl, $(C_1\text{-}C_6)$alkoxy, $(C_1\text{-}C_6)$alkanoyl, $(C_1\text{-}C_6)$alkanoyloxy, $(C_1\text{-}C_6)$alkoxycarbonyl, halo, cyano, nitro, carboxy, trifluoromethyl, trifluoromethoxy, $NR_{a1}R_{b1}$, or $S(O)_2NR_{c1}R_{d1}$.

Another specific value for $R_{14}$ is

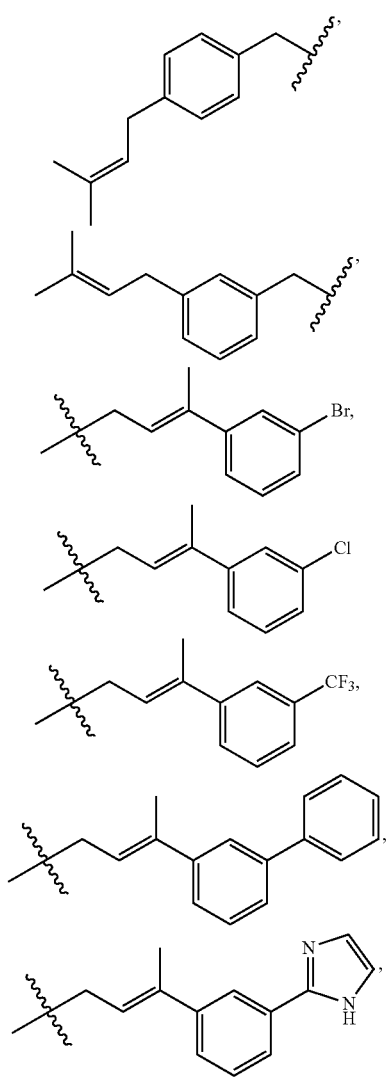

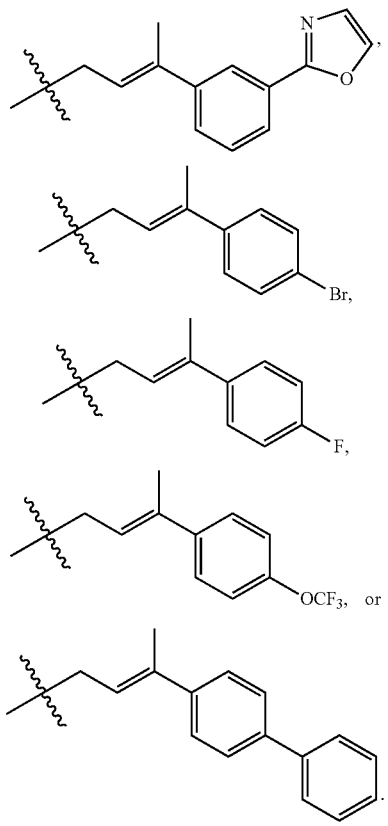

Another specific value for $R_{14}$ is a saturated $(C_1\text{-}C_{20})$alkyl chain that optionally comprises one or more aryl or heteroaryl rings in the chain wherein $(C_1\text{-}C_{20})$alkyl is optionally substituted with one or more halo, cyano, nitro, carboxy, trifluoromethyl, trifluoromethoxy, aryl, heteroaryl, $NR_mR_n$, or $S(O)_2NR_pR_q$ and wherein any aryl or heteroaryl is optionally substituted with one or more $(C_1\text{-}C_6)$alkyl, $(C_1\text{-}C_6)$alkoxy, $(C_1\text{-}C_6)$alkanoyl, $(C_1\text{-}C_6)$alkanoyloxy, $(C_1\text{-}C_6)$alkoxycarbonyl, halo, cyano, nitro, carboxy, trifluoromethyl, trifluoromethoxy, $NR_{a1}R_{b1}$, aryl, heteroaryl, or $S(O)_2NR_{c1}R_{d1}$.

Another specific value for $R_{14}$ is

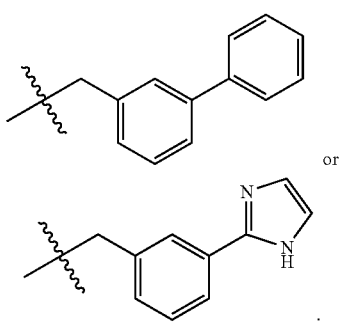

A specific value for $R_{15}$ is an unsaturated $(C_5\text{-}C_{20})$alkyl chain.

Another specific value for $R_{15}$ is a saturated or unsaturated $(C_5\text{-}C_{20})$alkyl chain that comprises one or more aryl rings in the chain.

Another specific value for $R_{15}$ is
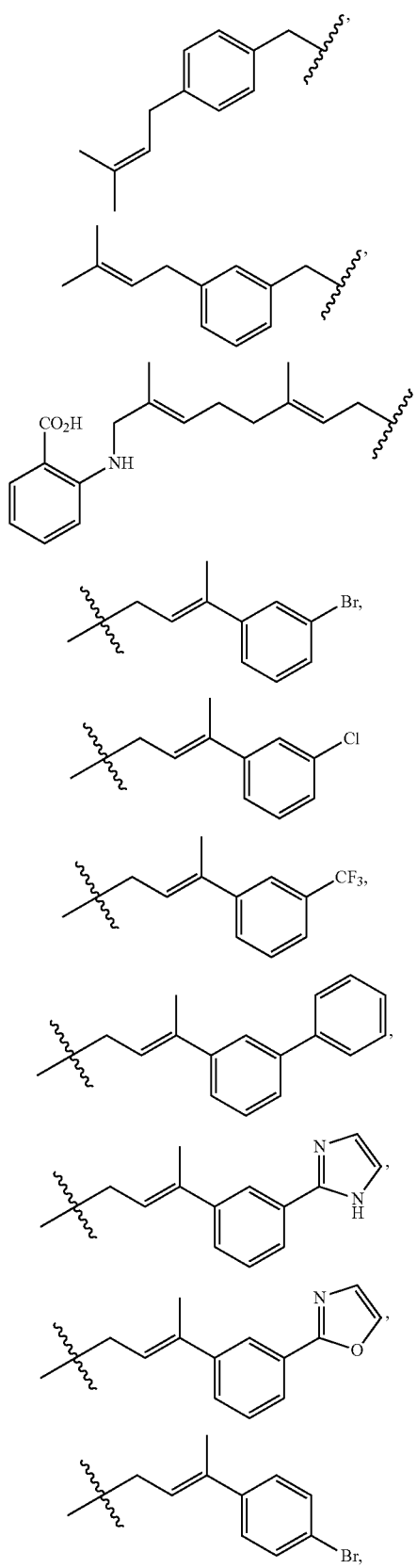
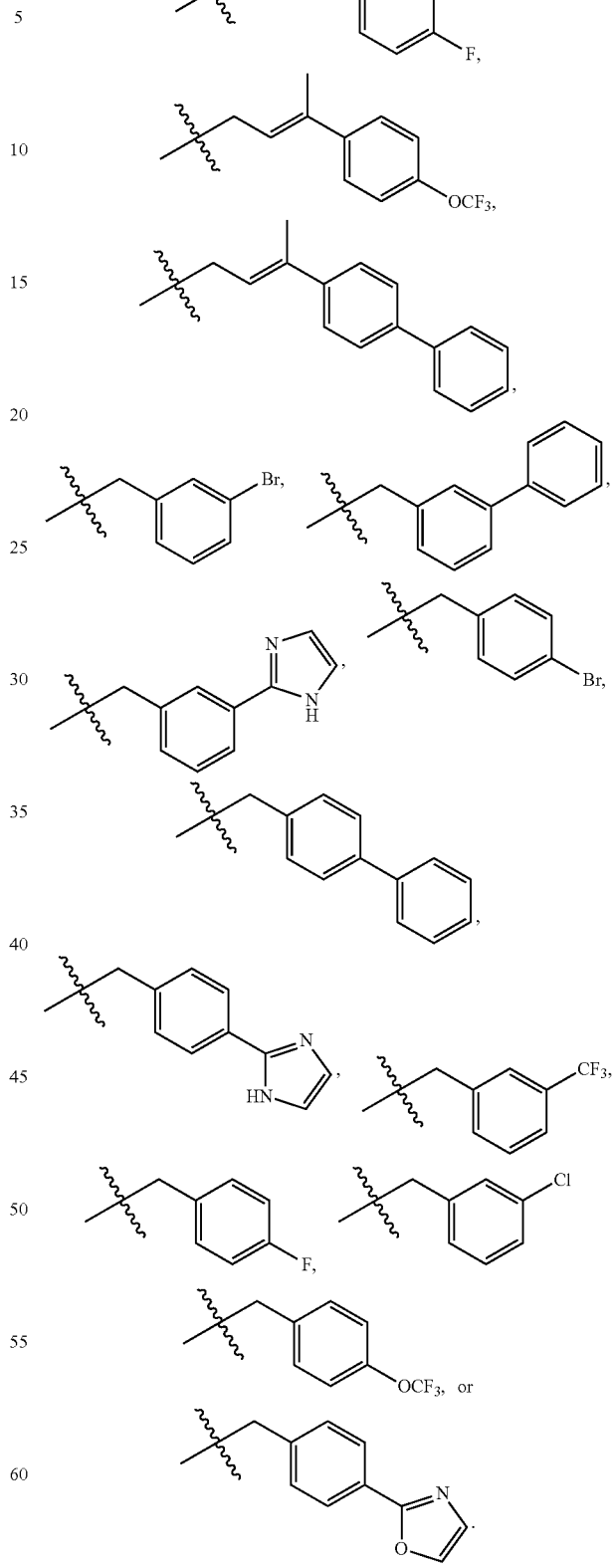
Another specific value for $R_{15}$ is an unsaturated ($C_5$-$C_{20}$) alkyl chain that comprises a heteroaryl ring in the chain.

Another specific value for $R_{15}$ is an unsaturated ($C_5$-$C_{20}$) alkyl chain that comprises a heteroaryl ring in the chain wherein the heteroaryl ring is indolyl.

Another specific value for $R_{15}$ is

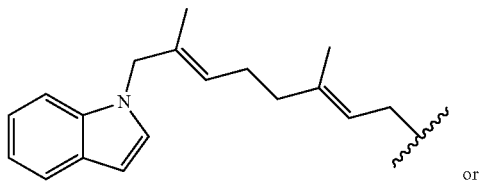

or

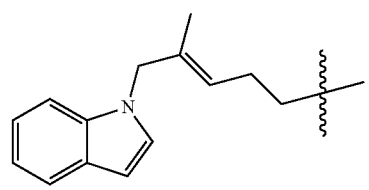

Another specific value for $R_{15}$ is an unsaturated ($C_5$-$C_{20}$) alkyl chain.

Another specific value for $R_{15}$ is:

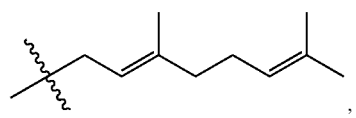

,

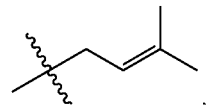

, or

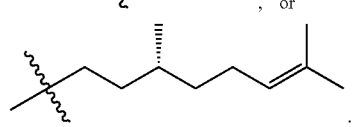

.

Another specific value for $R_{15}$ is methyl.

A specific value for $R_{16}$ is H or methyl.

Another specific value for $R_{16}$ is methyl.

Another specific value for $R_{16}$ is an unsaturated ($C_5$-$C_{20}$) alkyl chain.

Another specific value for $R_{16}$ is:

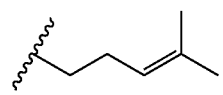

.

A specific compound is a compound wherein $R_9$, $R_{10}$, $R_{11}$ and $R_{12}$ are each OH.

A specific compound is a compound wherein $R_9$, $R_{10}$, $R_{11}$ and $R_{12}$ are each $(NaO)_2O$.

A specific compound is a compound wherein $R_9$, $R_{10}$, $R_{11}$ and $R_{12}$ are each alkoxy.

A specific compound is a compound wherein $R_9$, $R_{10}$, $R_{11}$ and $R_{12}$ are each ethoxy A specific compound is:

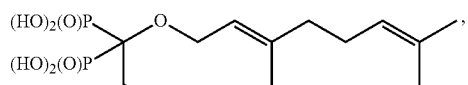

,

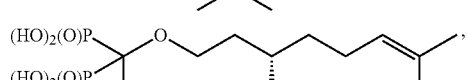

,

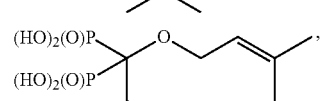

,

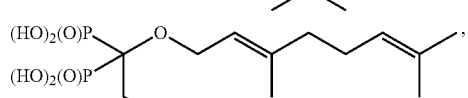

,

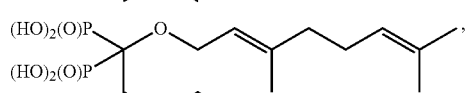

,

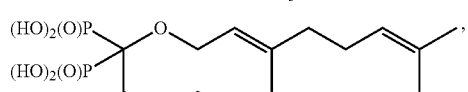

,

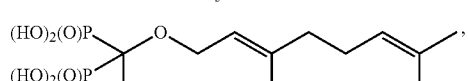

,

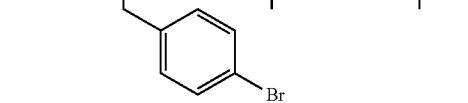

,

31
-continued
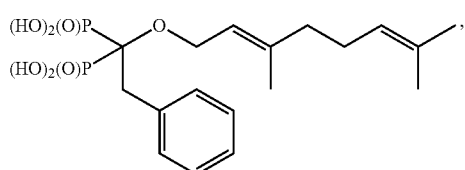
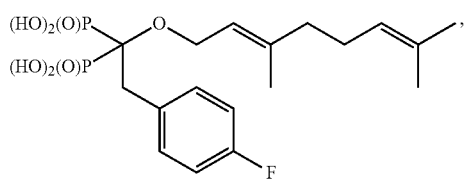
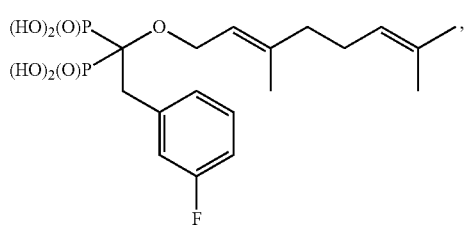
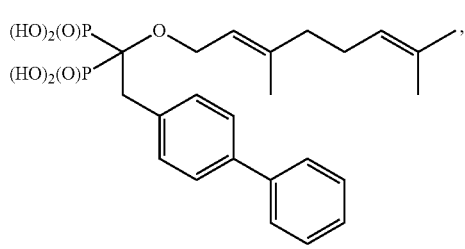
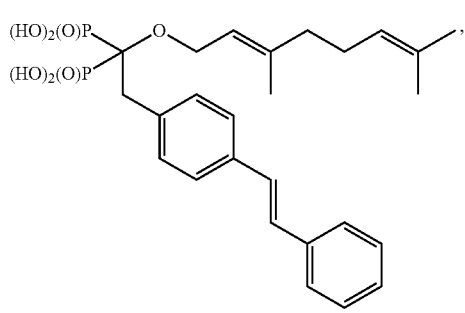
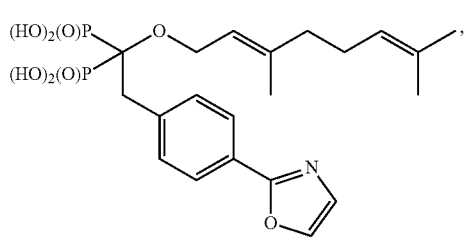
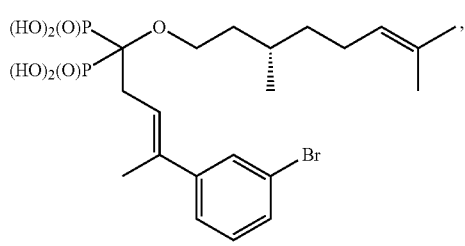
32
-continued
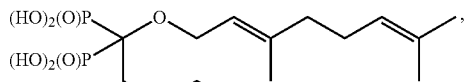
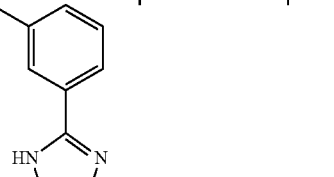
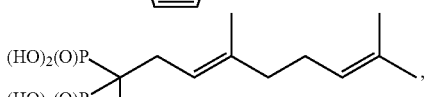
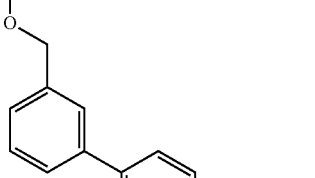
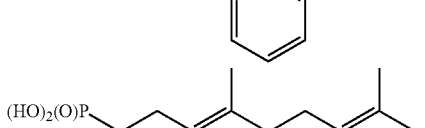
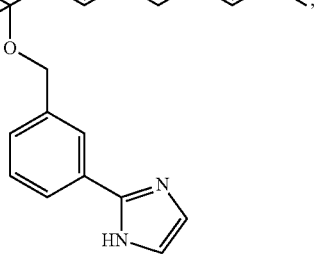
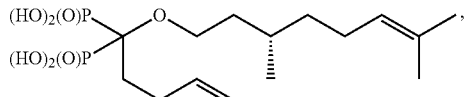
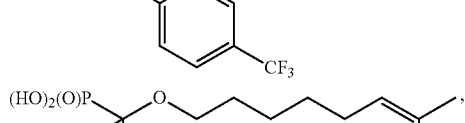
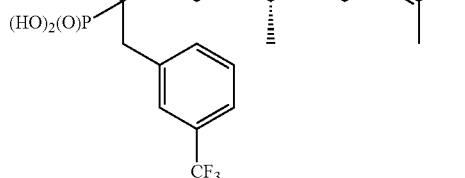
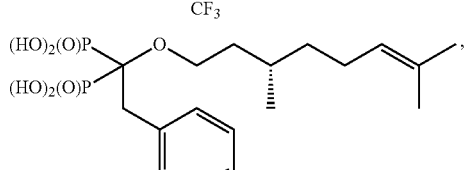
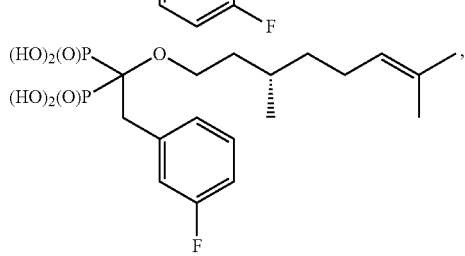

33
-continued
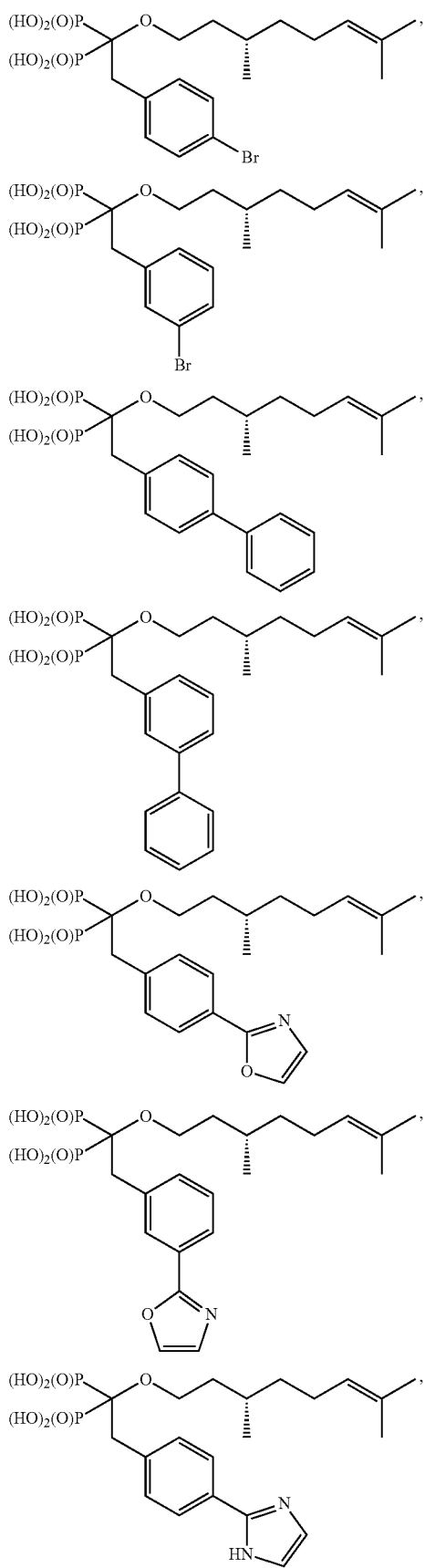
34
-continued
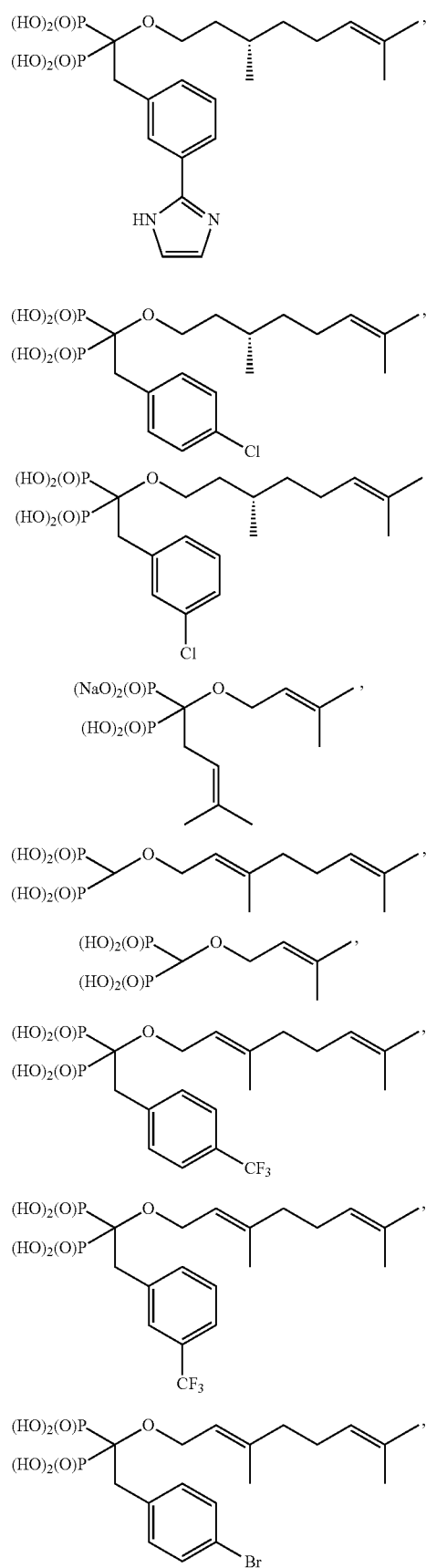

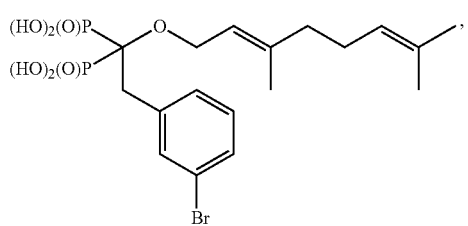
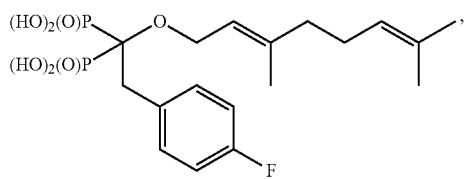
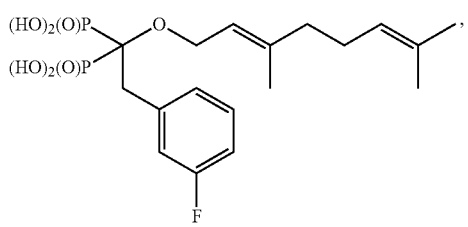
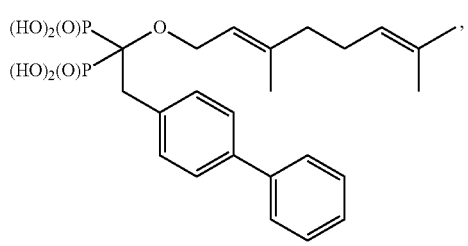
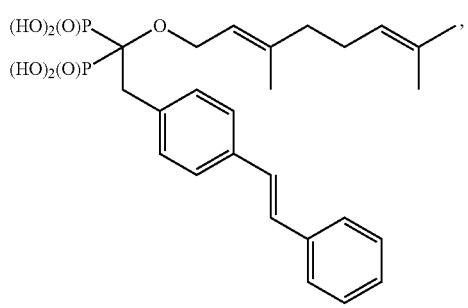
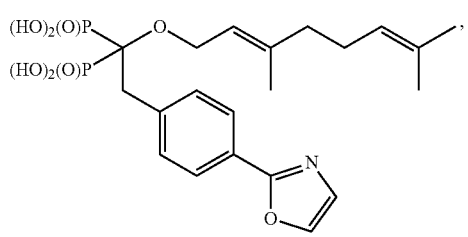
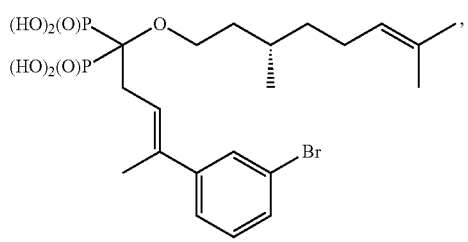
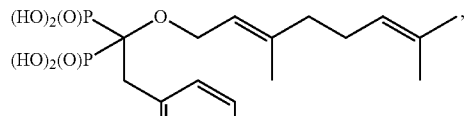
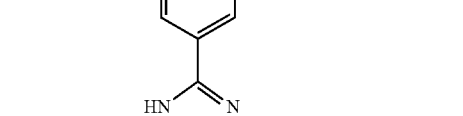
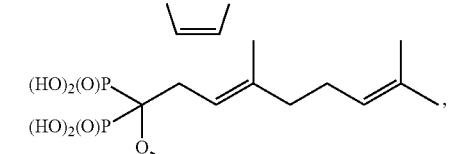
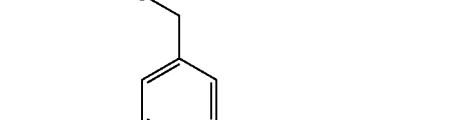
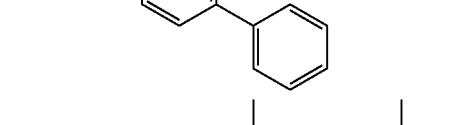
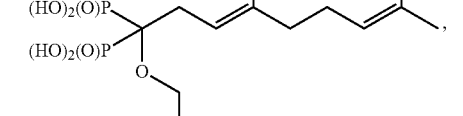
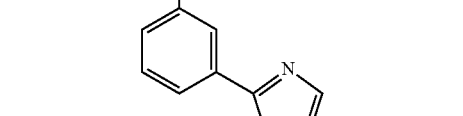
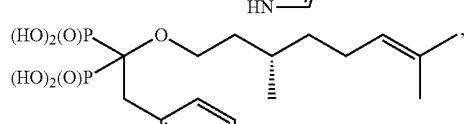
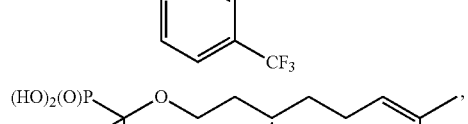
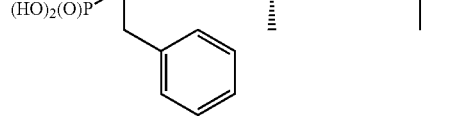
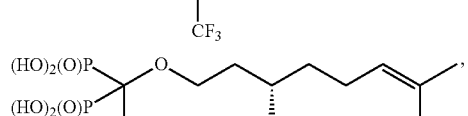
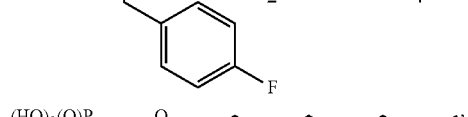
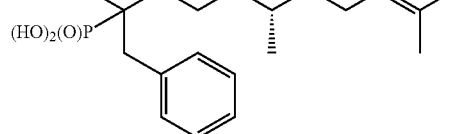

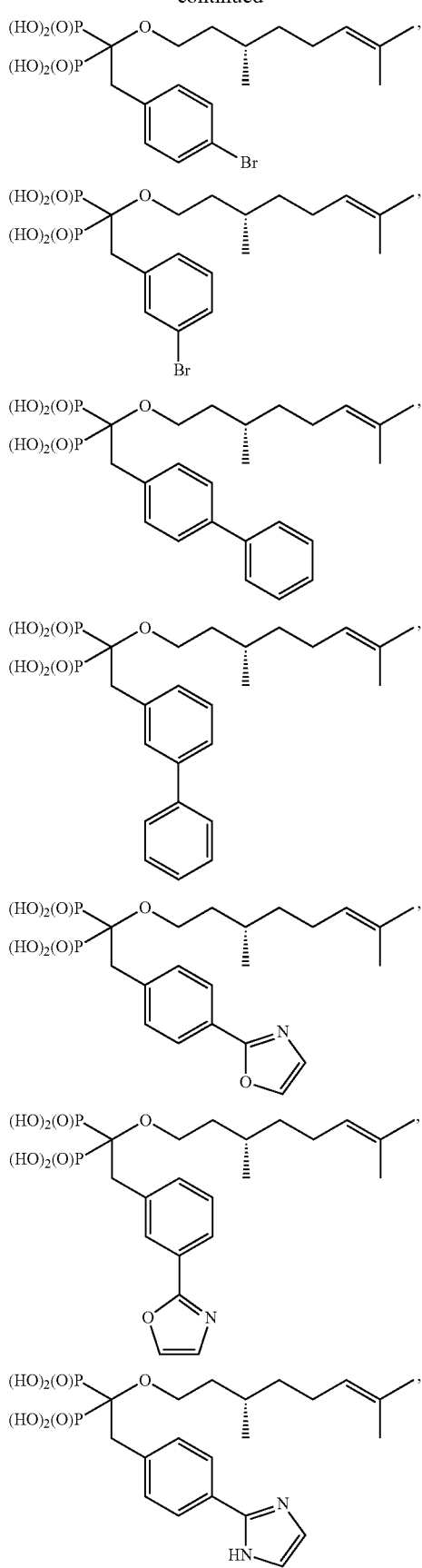
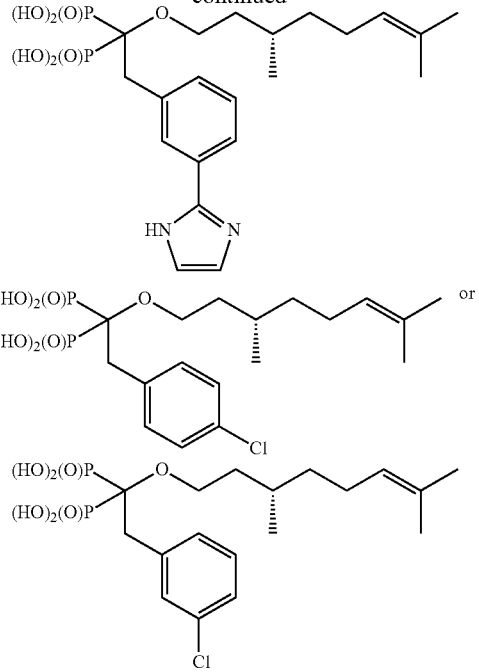
or a pharmaceutically acceptable salt or prodrug thereof.
A specific compound is:
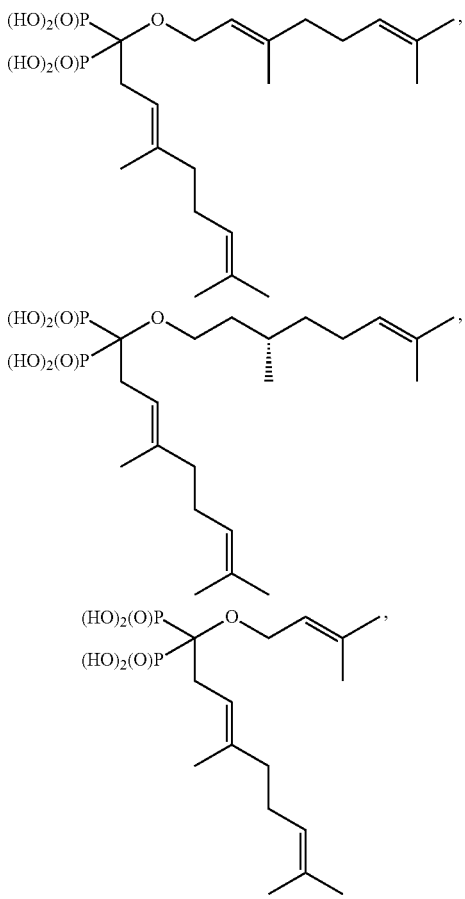

-continued

-continued
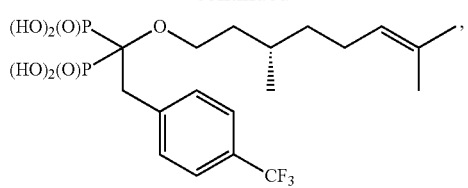
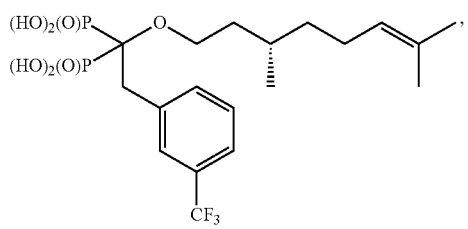
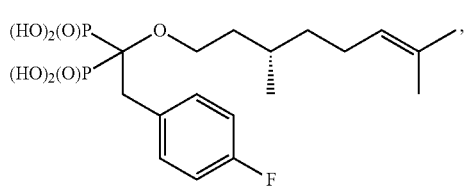
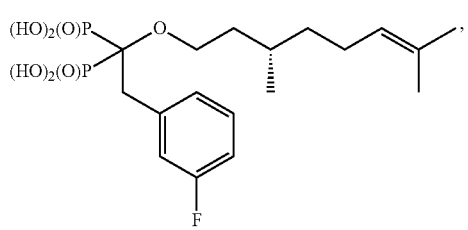
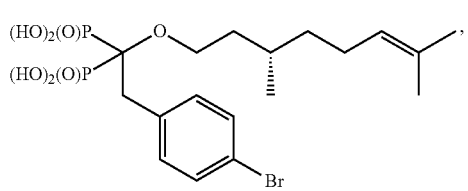
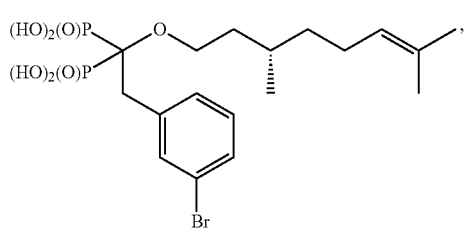
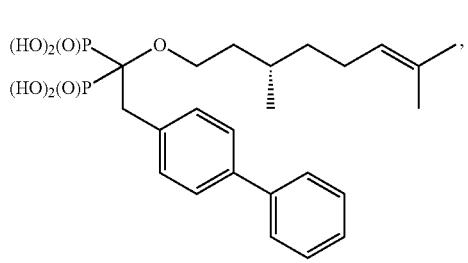
-continued
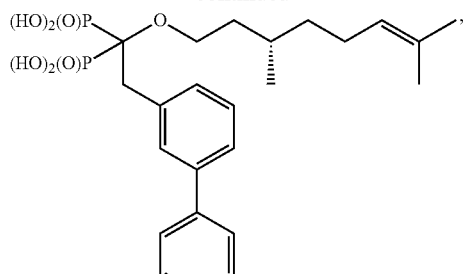
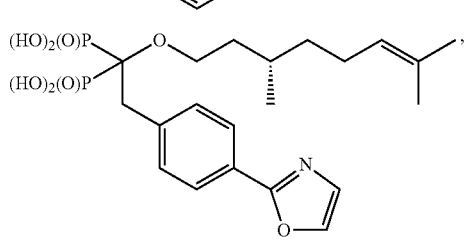
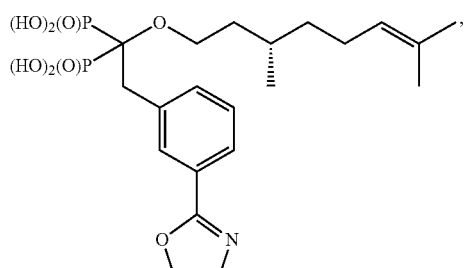
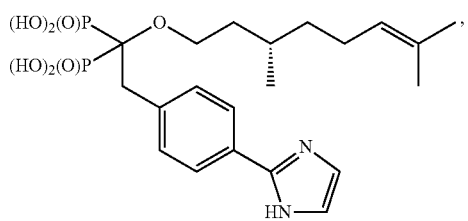
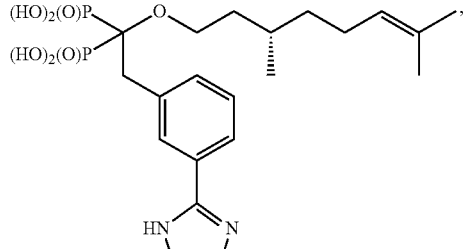
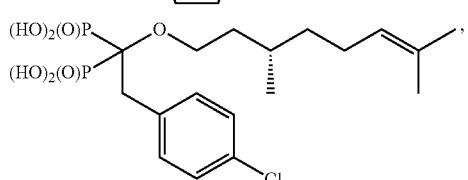
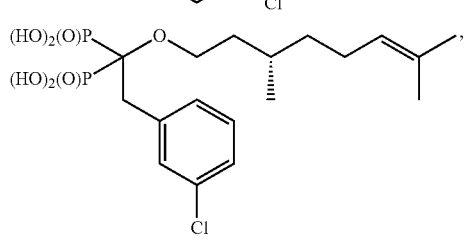

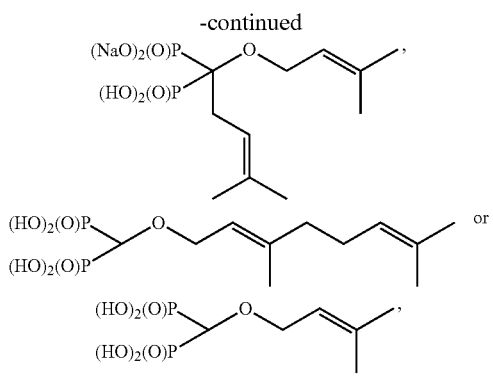

or a pharmaceutically acceptable salt or prodrug thereof.

The invention also provides the following embodiments labeled E1-E13.

E1: One embodiment provides a group of compounds of formula II wherein:
X is —$(CH_2)_m$— or —$(CH_2)_m CH(CH_3)$—;
m is an integer from 1 to 2;
$R_7$ is a saturated or unsaturated ($C_1$-$C_{20}$)alkyl chain that optionally comprises one or more aryl or heteroaryl rings in the chain wherein ($C_1$-$C_{20}$)alkyl is optionally substituted with one to three halo, cyano, nitro, carboxy, trifluoromethyl, trifluoromethoxy, $NH_2$, or $S(O)_2NH_2$, and wherein any aryl or heteroaryl is optionally substituted with one or more ($C_1$-$C_6$)alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, halo, cyano, nitro, carboxy, trifluoromethyl, trifluoromethoxy, $NH_2$, or $S(O)_2NH_2$;
$R_8$ is H or methyl;
each $R_9$, $R_{10}$, $R_{11}$, and $R_{12}$ is independently OH, or ($C_1$-$C_6$)alkoxy;
$R_{13}$ is a saturated or unsaturated ($C_1$-$C_{20}$)alkyl chain that optionally comprises one or more aryl or heteroaryl rings in the chain wherein ($C_5$-$C_{20}$)alkyl is optionally substituted with one or more halo, cyano, nitro, carboxy, trifluoromethyl, trifluoromethoxy, $NH_2$, or $S(O)_2NH_2$ and wherein any aryl or heteroaryl is optionally substituted with one or more ($C_1$-$C_6$)alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, halo, cyano, nitro, carboxy, trifluoromethyl, trifluoromethoxy, $NH_2$, or $S(O)_2NH_2$;
or a salt thereof.

E2. One embodiment provides a group of compounds of formula II wherein:
X is —$(CH_2)_m$— or —$(CH_2)_m CH(CH_3)$—;
m is an integer from 1 to 2;
$R_7$ is a saturated or unsaturated ($C_1$-$C_{20}$)alkyl chain optionally substituted with one to three halo, cyano, nitro, carboxy, trifluoromethyl, trifluoromethoxy, $NH_2$, or $S(O)_2NH_2$;
$R_8$ is H or methyl;
each $R_9$, $R_{10}$, $R_{11}$, and $R_{12}$ is independently OH, or ($C_1$-$C_6$)alkoxy;
$R_{13}$ is a saturated or unsaturated ($C_1$-$C_{20}$)alkyl chain that optionally comprises one or more aryl or heteroaryl rings in the chain wherein ($C_5$-$C_{20}$)alkyl is optionally substituted with one or more halo, cyano, nitro, carboxy, trifluoromethyl, trifluoromethoxy, $NH_2$, or $S(O)_2NH_2$ and wherein any aryl or heteroaryl is optionally substituted with one or more ($C_1$-$C_6$)alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, halo, cyano, nitro, carboxy, trifluoromethyl, trifluoromethoxy, $NH_2$, or $S(O)_2NH_2$;
or a salt thereof.

E3: One embodiment provides a group of compounds of formula II wherein:
X is —$(CH_2)_m$— or —$(CH_2)_m CH(CH_3)$—
m is an integer from 1 to 2;
$R_7$ is a saturated or unsaturated ($C_1$-$C_{20}$)alkyl chain;
$R_8$ is H or methyl;
each $R_9$, $R_{10}$, $R_{11}$, and $R_{12}$ is independently OH, or ($C_1$-$C_6$)alkoxy;
$R_{13}$ is a saturated or unsaturated ($C_1$-$C_{20}$)alkyl chain;
or a salt thereof.

E4: One embodiment provides a group of compounds of formula II wherein:
X is —$(CH_2)_m$— or —$(CH_2)_m CH(CH_3)$—
m is an integer from 1 to 2;
$R_7$ is saturated or unsaturated ($C_5$-$C_{20}$)alkyl chain;
$R_8$ is H or methyl;
each $R_9$, $R_{10}$, $R_{11}$, and $R_{12}$ is independently OH, or ($C_1$-$C_6$)alkoxy;
$R_{13}$ is a saturated or unsaturated ($C_1$-$C_{20}$)alkyl chain;
or a salt thereof.

E5: One embodiment provides a group of compounds of formula II wherein:
X is —$(CH_2)_m$— or —$(CH_2)_m CH(CH_3)$—
m is an integer from 1 to 2;
$R_7$ is a saturated or unsaturated ($C_5$-$C_{15}$)alkyl chain;
$R_8$ is H or methyl;
each $R_9$, $R_{10}$, $R_{11}$, and $R_{12}$ is independently OH, or ($C_1$-$C_6$)alkoxy;
$R_{13}$ is a saturated or unsaturated ($C_1$-$C_{20}$)alkyl chain;
or a salt thereof.

E6: One embodiment provides a group of compounds of formula II wherein:
X is —$(CH_2)_m$— or —$(CH_2)_m CH(CH_3)$—
m is an integer from 1 to 2;
$R_7$ is a saturated or unsaturated ($C_5$-$C_{10}$)alkyl chain;
$R_8$ is H or methyl;
each $R_9$, $R_{10}$, $R_{11}$, and $R_{12}$ is independently OH, or ($C_1$-$C_6$)alkoxy;
$R_{13}$ is a saturated or unsaturated ($C_1$-$C_{20}$)alkyl chain;
or a salt thereof.

E7: One embodiment provides a group of compounds of formula II wherein:
X is —$(CH_2)_m$— or —$(CH_2)_m CH(CH_3)$—;
m is an integer from 1 to 2;
$R_7$ is a saturated or unsaturated ($C_1$-$C_{20}$)alkyl chain;
$R_8$ is methyl;
each $R_9$, $R_{10}$, $R_{11}$, and $R_{12}$ is independently OH, or ($C_1$-$C_6$)alkoxy;
$R_{13}$ is a saturated or unsaturated ($C_1$-$C_{20}$)alkyl chain that comprises one or more aryl or heteroaryl rings in the chain wherein any aryl or heteroaryl is optionally substituted with one or two ($C_1$-$C_6$)alkyl, halo, trifluoromethyl, or trifluoromethoxy;
or a salt thereof.

E8: One embodiment provides a group of compounds of formula II wherein:
X is —$(CH_2)_m$— or —$(CH_2)_m CH(CH_3)$—;
m is an integer from 1 to 2;
$R_7$ is a saturated or unsaturated ($C_1$-$C_{20}$)alkyl chain comprising one or more aryl or heteroaryl rings in the chain wherein
$R_8$ is H or methyl;
each $R_9$, $R_{10}$, $R_{11}$, and $R_{12}$ is independently OH, or ($C_1$-$C_6$)alkoxy;
$R_{13}$ is a saturated or unsaturated ($C_1$-$C_{20}$)alkyl chain that optionally comprises one or more aryl or heteroaryl rings in the chain wherein ($C_5$-$C_{20}$)alkyl is optionally substituted with one or more halo, cyano, nitro, carboxy, trifluoromethyl, trifluoromethoxy, $NH_2$, or $S(O)_2NH_2$ and wherein any aryl or heteroaryl is optionally substituted with one or more ($C_1$-$C_6$) alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, halo, cyano, nitro, carboxy, trifluoromethyl, trifluoromethoxy, $NH_2$, or $S(O)_2NH_2$;
or a salt thereof.

E9: One embodiment provides a group of compounds of formula II wherein:
X is —$(CH_2)_m$— or —$(CH_2)_mCH(CH_3)$—;
m is an integer from 1 to 2;
$R_7$ is a saturated or unsaturated ($C_1$-$C_{20}$)alkyl chain comprising one or more aryl or heteroaryl rings in the chain wherein any aryl or heteroaryl is optionally substituted with one or more ($C_1$-$C_6$)alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, halo, cyano, nitro, carboxy, trifluoromethyl, trifluoromethoxy, $NH_2$, or $S(O)_2NH_2$;
$R_8$ is H or methyl;
each $R_9$, $R_{10}$, $R_{11}$, and $R_{12}$ is independently OH, or ($C_1$-$C_6$)alkoxy;
$R_{13}$ is a saturated or unsaturated ($C_1$-$C_{20}$)alkyl chain;
or a salt thereof.

E10: One embodiment provides a group of compounds of formula III wherein:
Y is —$(CH_2)_n$— or —$(CH_2)_nCH(CH_3)$—;
n is an integer from 1 to 2;
each $R_9$, $R_{10}$, $R_{11}$, and $R_{12}$ is independently OH, or ($C_1$-$C_6$)alkoxy;
$R_{14}$ is a saturated or unsaturated ($C_1$-$C_{20}$)alkyl chain that optionally comprises one or more aryl or heteroaryl rings in the chain wherein ($C_5$-$C_{20}$)alkyl is optionally substituted with one or more halo, cyano, nitro, carboxy, trifluoromethyl, trifluoromethoxy, $NH_2$, or $S(O)_2NH_2$ and wherein any aryl or heteroaryl is optionally substituted with one or more ($C_1$-$C_6$) alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, halo, cyano, nitro, carboxy, trifluoromethyl, trifluoromethoxy, $NH_2$, or $S(O)_2NH_2$;
$R_{15}$ is a saturated or unsaturated ($C_1$-$C_{20}$)alkyl chain that optionally comprises one or more aryl or heteroaryl rings in the chain wherein ($C_1$-$C_{20}$)alkyl is optionally substituted with one or more halo, cyano, nitro, carboxy, trifluoromethyl, trifluoromethoxy, $NH_2$, or $S(O)_2NH_2$ and wherein any aryl or heteroaryl is optionally substituted with one or more ($C_1$-$C_6$) alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, halo, cyano, nitro, carboxy, trifluoromethyl, trifluoromethoxy, $NH_2$, or $S(O)_2NH_2$;
$R_{16}$ is H or methyl;
or a salt thereof.

E11: One embodiment provides a group of compounds of formula III wherein:
Y is —$(CH_2)_n$— or —$(CH_2)_nCH(CH_3)$—;
n is an integer from 1 to 2;
each $R_9$, $R_{10}$, $R_{11}$, and $R_{12}$ is independently OH, or ($C_1$-$C_6$)alkoxy;
$R_{14}$ is a saturated or unsaturated ($C_1$-$C_{20}$)alkyl chain that optionally comprises one or more aryl or heteroaryl rings in the chain wherein ($C_5$-$C_{20}$)alkyl is optionally substituted with one or more halo, cyano, nitro, carboxy, trifluoromethyl, trifluoromethoxy, $NH_2$, or $S(O)_2NH_2$ and wherein any aryl or heteroaryl is optionally substituted with one or more ($C_1$-$C_6$) alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, halo, cyano, nitro, carboxy, trifluoromethyl, trifluoromethoxy, $NH_2$, or $S(O)_2NH_2$;
$R_{15}$ is H or a saturated or unsaturated ($C_1$-$C_{20}$)alkyl chain optionally substituted with one or more halo, cyano, nitro, carboxy, trifluoromethyl, trifluoromethoxy, $NH_2$, or $S(O)_2NH_2$;
$R_{16}$ is H or methyl;
or a salt thereof.

E12: One embodiment provides a group of compounds of formula III wherein:
Y is —$(CH_2)_n$— or —$(CH_2)_nCH(CH_3)$—;
n is an integer from 1 to 2;
each $R_9$, $R_{10}$, $R_{11}$, and $R_{12}$ is independently OH, or ($C_1$-$C_6$)alkoxy;
$R_{14}$ is a saturated or unsaturated ($C_1$-$C_{20}$)alkyl chain that optionally comprises one or more aryl or heteroaryl rings in the chain wherein ($C_5$-$C_{20}$)alkyl is optionally substituted with one or more halo, cyano, nitro, carboxy, trifluoromethyl, trifluoromethoxy, $NH_2$, or $S(O)_2NH_2$ and wherein any aryl or heteroaryl is optionally substituted with one or more ($C_1$-$C_6$) alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, halo, cyano, nitro, carboxy, trifluoromethyl, trifluoromethoxy, $NH_2$, or $S(O)_2NH_2$;
$R_{15}$ is H or a saturated or unsaturated ($C_1$-$C_{20}$)alkyl chain optionally substituted with one or more halo, cyano, nitro, carboxy, trifluoromethyl, trifluoromethoxy, $NH_2$, or $S(O)_2NH_2$;
$R_{16}$ is H or methyl;
or a salt thereof.

E13: Any of the embodiments E1-E12, wherein any aryl is phenyl and any heteroaryl comprises 5-6 ring atoms of which between 1 and 4 are heteroatoms chosen from N, O, and S, either of which may be optionally substituted with one or two ($C_1$-$C_6$)alkyl, ($C_1$-$C_6$)alkoxy, halo, trifluoromethyl, or trifluoromethoxy.

The invention also provides compounds of formula II wherein $R_7$ is a saturated or unsaturated ($C_5$-$C_{20}$)alkyl chain that comprises one or more heteroaryl rings and optionally comprises one or more aryl rings in the chain wherein ($C_5$-$C_{20}$)alkyl is optionally substituted with one or more halo, cyano, nitro, carboxy, trifluoromethyl, trifluoromethoxy, $NR_mR_n$, or $S(O)_2NR_pR_q$ and wherein any aryl or heteroaryl is optionally substituted with one or more ($C_1$-$C_6$)alkyl, ($C_1$-$C_6$)alkoxy, ($C_1$-$C_6$)alkanoyl, ($C_1$-$C_6$)alkanoyloxy, ($C_1$-$C_6$) alkoxycarbonyl, halo, cyano, nitro, carboxy, trifluoromethyl, trifluoromethoxy, $NR_{a1}R_{b1}$, or $S(O)_2NR_{c1}R_{d1}$.

The invention also provides compounds of formula I wherein $R_7$ is —($C_5$-$C_{20}$)alkyl-$Z^1$ wherein ($C_5$-$C_{20}$)alkyl is saturated or unsaturated and is optionally substituted with one or more halo, cyano, nitro, carboxy, trifluoromethyl, trifluoromethoxy, $NR_mR_n$, or $S(O)_2NR_pR_q$; and wherein $Z^1$ is heteroaryl optionally substituted with one or more (e.g. 1, 2, 3 or 4) ($C_1$-$C_6$)alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, halo, cyano, nitro, carboxy, trifluoromethyl, trifluoromethoxy, $NR_{a1}R_{b1}$, or $S(O)_2NR_{c1}R_{d1}$.

A specific value for $Z^1$ is furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

Another specific value for $Z^1$ is furyl, imidazolyl, triazolyl, triazinyl, oxazoyl, isoxazoyl, thiazolyl, isothiazoyl, pyrazolyl, pyrrolyl, pyrazinyl, tetrazolyl, thienyl, pyrimidinyl (or its N-oxide), indolyl, isoquinolyl (or its N-oxide) or quinolyl (or its N-oxide).

Another specific value for $Z^1$ is furyl, triazolyl, triazinyl, oxazoyl, isoxazoyl, thiazolyl, isothiazoyl, pyrazolyl, pyrrolyl, pyrazinyl, tetrazolyl, thienyl, pyrimidinyl (or its N-oxide), indolyl, isoquinolyl (or its N-oxide) or quinolyl (or its N-oxide).

Another specific value for $Z^1$ is indolyl.

In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredients which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat.

No. 4,608,392), Geria (U.S. Pat. No. 4,992,478), Smith et al. (U.S. Pat. No. 4,559,157) and Wortzman (U.S. Pat. No. 4,820,508).

The compound of formula I can also be administered by inhalation. Formulations suitable for intrapulmonary or nasal administration typically have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared using conventional methods. The compound of Formula I can be formulated for aerosol delivery using a nebulizer, pressurized metered dose inhaler (pMDI), or dry powder inhaler (DPI). Non-limiting examples of nebulizers include atomizing, jet, ultrasonic, pressurized, vibrating porous plate, or equivalent nebulizers including those nebulizers utilizing adaptive aerosol delivery technology.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compounds of formula I, formula II and formula III can be prepared using standard synthetic techniques, including those described in U.S. Pat. No. 7,268,124 and International Application WO2014/008407 both of which are hereby incorporated by reference in their entirety.

The ability of a compound of the invention to modulate peroxide production can be determined using pharmacological models which are well known to the art, for example see Osborn-Heaford, H. L., et al., *J. Biol. Chem.* 2012, 287, 3301-3312.

The ability of a compound of the invention to modulate the importation of Rac1 into the mitochondria of pulmonary macrophages can be determined using pharmacological models which are well known to the art, for example see Osborn-Heaford, H. L., et al., *J. Biol. Chem.* 2012, 287, 3301-3312.

The ability of a compound of the invention to treat fibrosis can be determined using pharmacological models, such as total lung hydroxyproline levels, which are well known to the art, for example see Osborn-Heaford, H. L., et al., *J. Biol. Chem.* 2012, 287, 3301-3312; Horan, G. S., et al., *American Journal of Respiratory and Critical Care Medicine* 2008, 177, 56-65; and Sisson, T. H., et al., *Human Gene Therapy* 1999, 10, 2315-2323.

The invention will now be illustrated by the following non-limiting Examples.

Example 1

Rac1 is localized in the mitochondria of alveolar macrophages from patients with pulmonary fibrosis, and mitochondrial import requires the C-terminal cysteine of Rac1 (cys-189), which can be post-translationally modified by geranylgeranylation. Asbestos-exposed mice harboring a conditional deletion of Rac1 in macrophages demonstrated decreased oxidative stress and were significantly protected from developing pulmonary fibrosis. The geranylgeranyl pyrophosphate (GGPP) synthase inhibitor, digeranyl bisphosphonate (DGBP) was utilized to determine if inhibition of Rac1 geranylgeranylation reduced mitochondrial $H_2O_2$.

Figure 1:
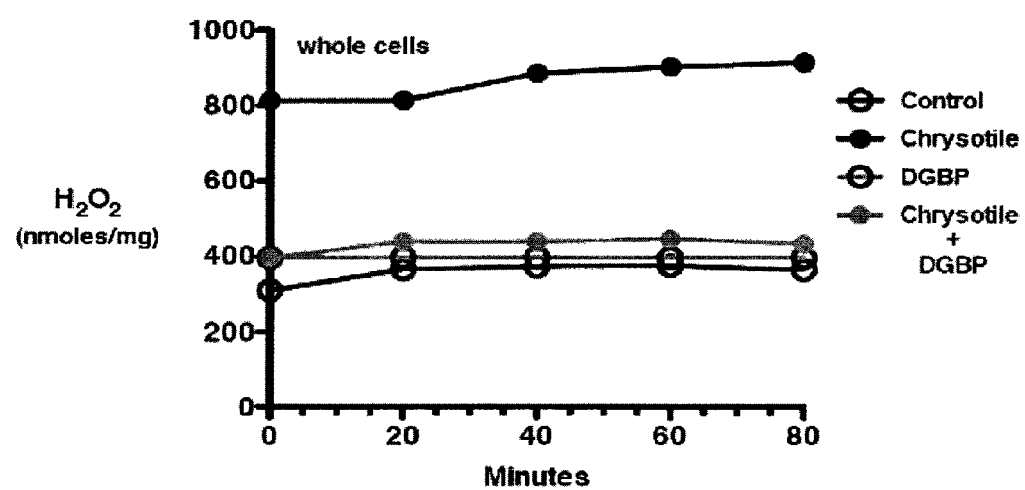
FIG. 1. Macrophages were cultured in the presence or absence of DGBP (10 mM) and then exposed to chrysotile asbestos (10 μg/cm$^2$). $H_2O_2$ generation was determined by pHPA assay. n=3; *p<0.05.
Figure 2:
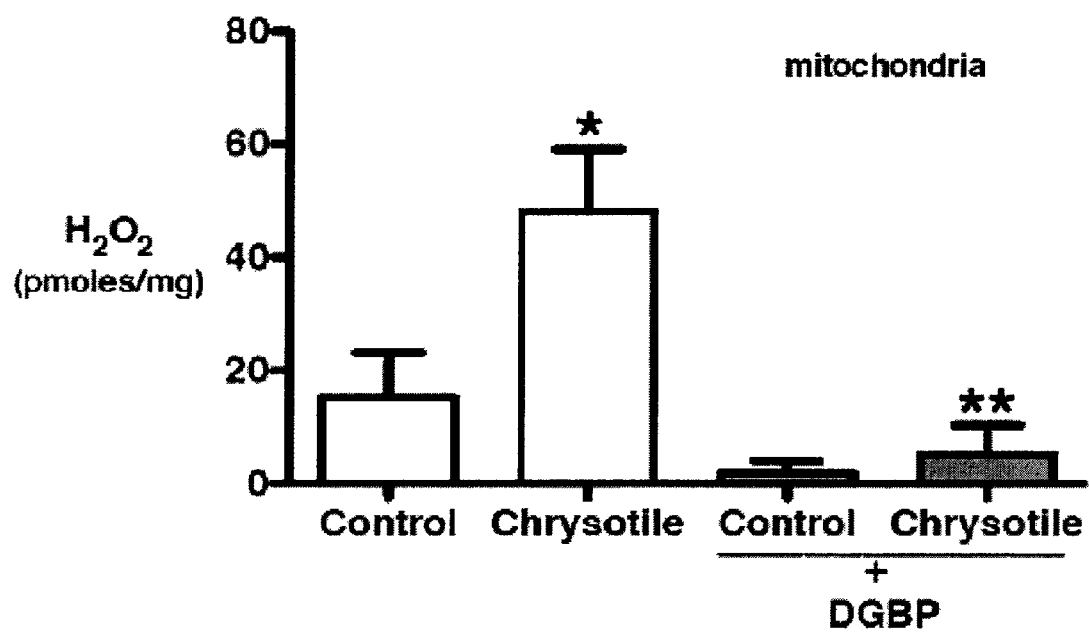
FIG. 2. Macrophages were cultured in the presence or absence of DGBP (10 mM) and then exposed to chrysotile asbestos (10 μg/cm$^2$). Mitochondria were isolated, and $H_2O_2$ generation was determined by pHPA assay. n=3; *p<0.05 vs. all other groups, and **p<0.05 vs. chrysotile+vehicle.

Macrophages exposed to chrysotile asbestos had a significant increase in $H_2O_2$ generation, and macrophages treated with DGBP had a significant reduction in $H_2O_2$ to control levels (FIG. 1). Because prior data suggested that the mitochondria are critical for the elevation in $H_2O_2$ levels in macrophages, the effect of DGBP on mitochondrial $H_2O_2$ generation was determined. DGBP abrogated asbestos-induced mitochondrial $H_2O_2$ generation below control levels (FIG. 2).

Figure 3:
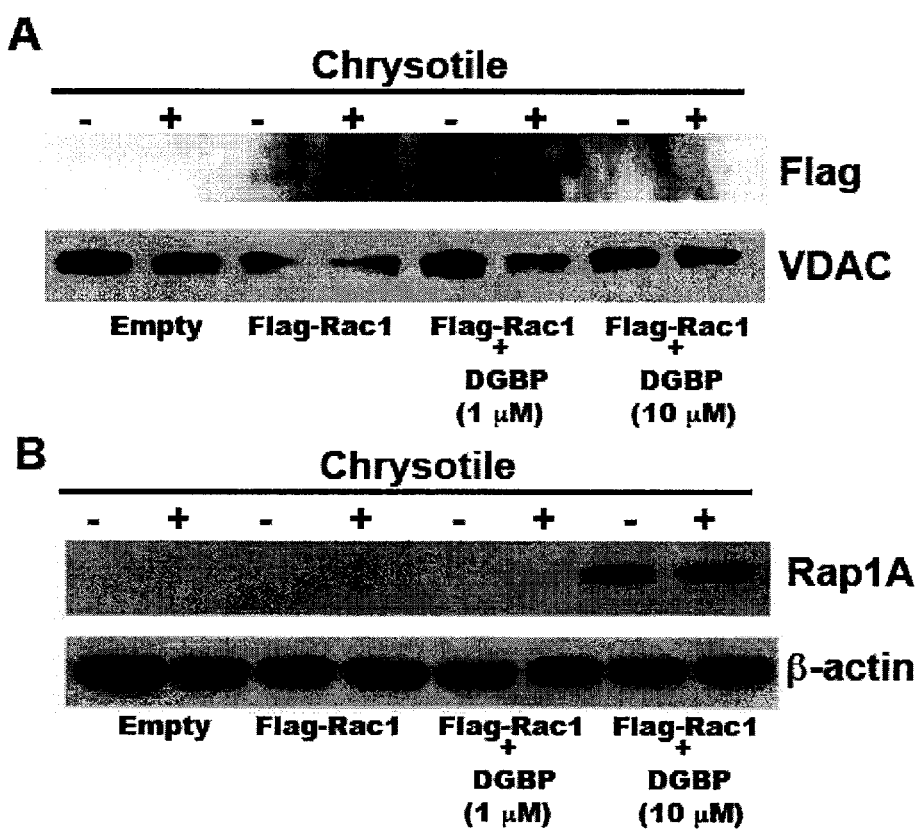
FIG. 3. Macrophages were transfected with either an empty or a Flag-Rac1. The cells were then cultured in the presence or absence of DGBP at the concentrations shown. Cells were exposed to chrysotile asbestos (10 μg/cm$^2$) for 1 h the following day. (A) Mitochondria were isolated and immunoblot analysis was performed for Flag-Rac1. (B) Whole cell lysates were isolated, and immunoblot analysis for Rap1A was performed.

In order to link the effect of DGBP to Rac1, macrophages were exposed to chrysotile asbestos in the presence or absence of DGBP and mitochondrial Rac1 import was determined DGBP inhibited mitochondrial Rac1 import in a dose-dependent manner (FIG. 3A), and this was secondary to inhibition of geranylgeranylation (FIG. 3B).

Figure 4:
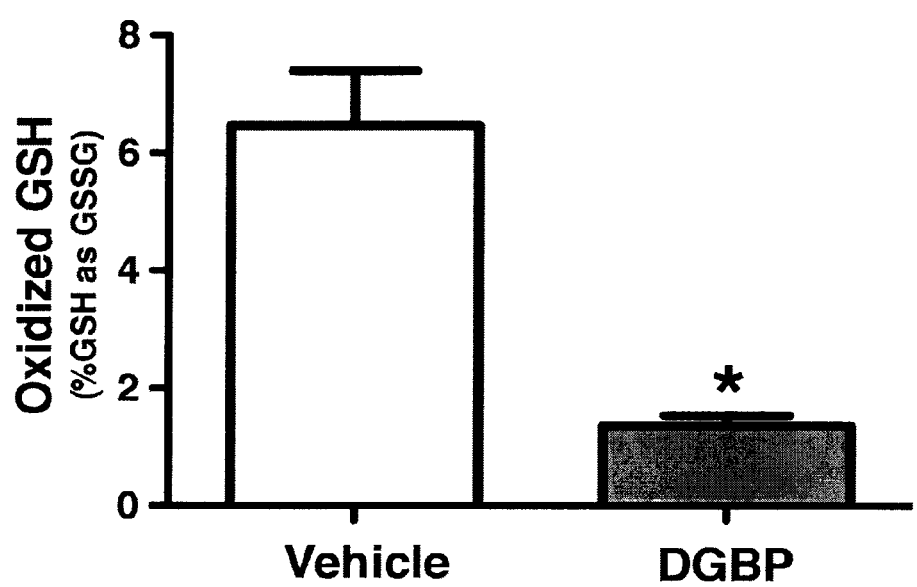
FIG. 4. DGBP inhibits pulmonary oxidative stress. WT mice were exposed to chrysotile asbestos (100 μg i.t.). Water or DGBP was administered via osmotic subcutaneous pump. Mice were euthanized after 21 days, and lungs were removed for glutathione assay. n=6 per condition. *p<0.05.

To determine the biological relevance of DGBP on oxidative stress in vivo, WT mice were exposed to asbestos (100 μg i.t.). The mice were treated with vehicle or DGBP via administration utilizing a subcutaneous osmotic pump. After 21 days, the mice were euthanized, and lung oxidative stress was determined by GSH assay. Mice that received DGBP had a significant reduction in lung oxidative stress compared to mice that received the vehicle (FIG. 4).

Figure 5:
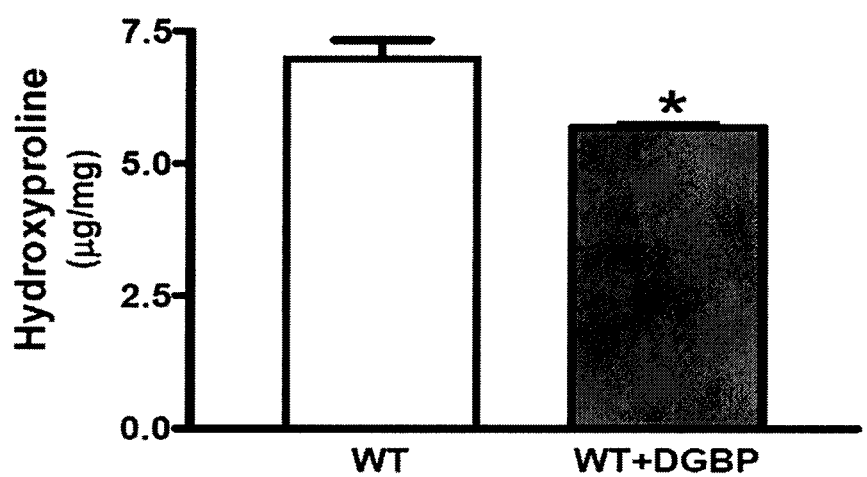
FIG. 5. DGBP attenuates asbestos-induced pulmonary fibrosis. WT mice were exposed to chrysotile asbestos (100 μg i.t.). Water or DGBP was administered via osmotic subcutaneous pump. Mice were euthanized after 21 days, and fibrosis was determined by hydroxyproline assay. n=3 per condition. *p<0.05.
Figure 6:
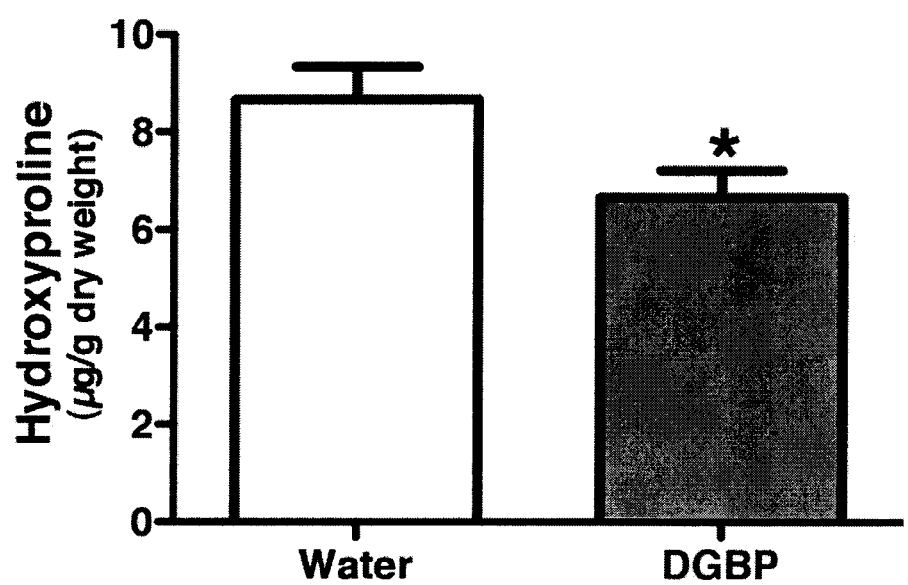
FIG. 6. DGBP attenuates bleomycin-induced pulmonary fibrosis. WT mice were exposed to bleomycin 2.0 U/kg i.t. Water or DGBP was administered via osmotic subcutaneous pump. Mice were euthanized after 21 days, and fibrosis was determined by hydroxyproline assay. n=3 per condition. *p<0.05.

Because mitochondrial-mediated pulmonary oxidative stress is linked to pulmonary fibrosis, the effect of DGBP on the development of pulmonary fibrosis was investigated. Asbestos- and bleomycin-exposed WT mice that received DGBP have significantly less pulmonary fibrosis compared to mice that receive the vehicle (FIGS. 5 and 6). The results demonstrate that mitochondrial import of Rac1 requires geranylgeranylation and modulates mitochondrial $H_2O_2$ production in alveolar macrophages during pulmonary fibrosis. Inhibition of Rac1 geranylgeranylation with DGBP provides a potential therapeutic modality to halt development and/or progression of pulmonary fibrosis.

Example 2

In vivo evaluation of digeranyl bisphosphonate (DGBP) on Rac1 mitochondrial import, lung oxidative stress, and progression of the fibrotic response.

Methods

Materials.

Bleomycin was obtained from the University of Iowa Hospital and Clinics hospital stores. Chrysotile was provided the College of Public Health. University of Iowa, Iowa City, Iowa. p-Hydroxylphenyl acetic acid (pHPA), horseradish peroxidase (HRP), α-ketoglutarate and NADPH were purchased from Sigma Chemical Company (St. Louis, Mo.).

Human Subjects.

The Human Subjects Review Board of the University of Iowa Carver College of Medicine approved the protocol of obtaining alveolar macrophages from normal volunteers and patients with asbestosis. Normal volunteers had to meet the following criteria: (1) age between 18 and 55 years; (2) no history of cardiopulmonary disease or other chronic disease; (3) no prescription or nonprescription medication except oral contraceptives; (4) no recent or current evidence of infection; and (5) lifetime nonsmoker. Alveolar macrophages were also obtained from patients with asbestosis. Patients with IPF had to meet the following criteria: (1) FVC and DLCO at least 50% predicted; (2) current nonsmoker; (3) no recent or current evidence of infection; and (4) evidence of restrictive physiology on pulmonary function tests and interstitial fibrosis on chest computed tomography. Fiberoptic bronchoscopy with bronchoalveolar lavage was performed after subjects received intramuscular atropine (0.6 mg) and local anesthesia. Three sub-segments of the lung were lavaged with five 20-ml aliquots of normal saline, and the first aliquot in each was discarded. The percentage of alveolar macrophages was determined by Wright-Giemsa stain and varied from 90 to 98%.

Mice.

Wild-type C57Bl/6 mice were from Jackson Laboratories (Bar Habor, Me.). The University of Iowa Institutional Animal Care and Use Committee approved all protocols. After equilibration, osmotic pumps (Alzet, Cupertino, Calif.) containing either vehicle (water) or DGBP (0.2 mg/kg/day) were implanted subcutaneously, as describe previously (Erickson, J. R., et al., *A dynamic pathway for calcium-independent activation of CaMKII by methionine oxidation*. Cell, 2008. 133(3): p. 462-74). Bleomycin (2.0 U/kg) or chrysotile (100 µg/cm$^2$) was administered intratracheally. Mice were euthanized and fibrosis determined as previously described (Osborn-Heaford, H. L., et al., *Mitochondrial Rac1 GTPase Import and Electron Transfer from Cytochrome c Are Required for Pulmonary Fibrosis*. The Journal of biological chemistry, 2012. 287(5): p. 3301-12, He, C., et al., *Accelerated Development of Pulmonary Fibrosis via Cu,Zn-superoxide Dismutase-induced Alternative Activation of Macrophages*. J Biol Chem, 2013. 288(28): p. 20745-57).

Cell Culture.

THP-1, MLE-12, and HLF-1 cell lines were obtained from American Type Culture Collection (Manassas, Va.). Cells were maintained in RPMI-1640, Hites, or F-12K media supplemented with fetal bovine serum and penicillin/streptomycin. All experiments were performed with media supplemented with 0.5% serum.

Synthesis of Digeranyl Bisphosphonate (DGBP).

DGBP was synthesized as previously described (Shull, L. W., Wiemer, A. J., Hohl, R. J., and Wiemer, D. F., *Synthesis and biological activity of isoprenoid bisphosphonates*. Bioorg Med Chem, 2006. 14(12): p. 4130-4136, Shull, L. W. a. W., D. F., *Copper-mediated displacements of allylic THP ethers on a bisphosphonate template*. J Org Chem, 2005. 690(10): p. 2521-2530).

Determination of $H_2O_2$ Generation.

Extracellular $H_2O_2$ production was determined fluorometrically, as previously described (He, C., et al., *Mitochondrial Cu,Zn-Superoxide Dismutase Mediates Pulmonary Fibrosis by Augmenting $H_2O_2$ Generation*. J Biol Chem, 2011. 286(17): p. 15597-607). Briefly, cells were incubated in phenol-red free Hanks' balanced salt solution supplemented with 6.5 mM glucose, 1 mM HEPES, 6 mM sodium bicarbonate, 1.6 mM pHPA, and 0.95 µg/ml HRP. Fluorescence of the pHPA-dimer was measured using a spectrofluorometer at excitation of 320 nm and emission of 400 nm. Mitochondrial $H_2O_2$ was measured by resuspending mitochondria in phenol-red free Hanks' balanced salt solution supplemented with 6.5 mM glucose, 1 mM HEPES, 6 mM sodium bicarbonate, 1.6 mM pHPA, 0.95 µg/ml HRP and 5 mM α-ketoglutarate.

Isolation of Mitochondria.

Mitochondria were isolated as previously described (He, C., et al., *Mitochondrial Cu,Zn-Superoxide Dismutase Mediates Pulmonary Fibrosis by Augmenting H2O2 Generation*. J Biol Chem, 2011. 286(17): p. 15597-607).

Hydroxyproline Assay.

Lung tissue was dried to stable weight and acid hydrolyzed with 6N HCl for 24 h at 120° C. Hydroxyproline concentration normalized, to dry weight of the lung, was determined as described previously (Osborn-Heaford, H. L., et al., *Mitochondrial Rac1 GTPase Import and Electron Transfer from Cytochrome c Are Required for Pulmonary Fibrosis*. The Journal of biological chemistry, 2012. 287(5): p. 3301-12).

Thiol Determination.

Reduced and oxidized glutathione in the lung were determined as described previously (He, C., et al., *Mitochondrial Cu,Zn-Superoxide Dismutase Mediates Pulmonary Fibrosis by Augmenting H2O2 Generation*. J Biol Chem, 2011. 286 (17): p. 15597-607).

Immunoblot Analysis.

Whole cells lysates and sub-cellular fractions were separated by SDS-PAGE and transferred to PVDF membranes. Immunoblot analyses on the membranes were performed with the designated antibodies followed by the appropriate secondary antibody cross-linked to HRP.

ELISA.

Active TGF-β in BAL fluid was measured by ELISA (R&D, Minneapolis, Minn.), according to manufacturer's instructions.

Statistical Analysis.

Statistical comparisons were performed using an unpaired, two-tailed t test or one-way ANOVA followed by Tukey's post-test to compare columns. Values in figures are expressed as means with standard errors and p<0.05 was considered to be significant.

Results

Alveolar Macrophages from IPF Patients Show Increased Mitochondrial Oxidative Stress and Rac1 Activation.

Figure 7:
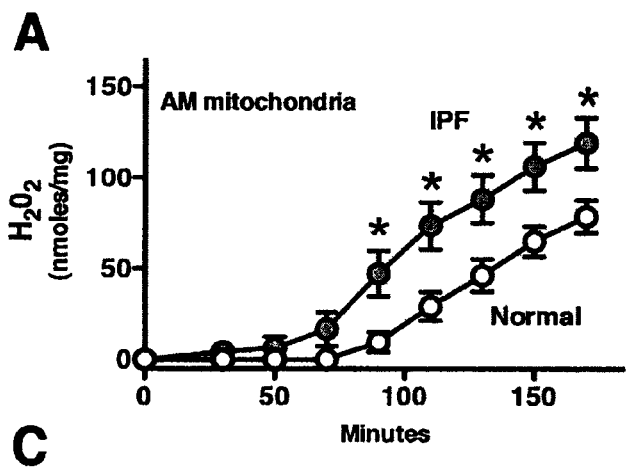
FIG. 7. Alveolar macrophages from IPF patients have increased oxidative stress and Rac1 activity. (A) Normal subjects (n=5) and IPF patients (n=7). $H_2O_2$ activity was measured by pHPA assay. *p<0.05 normal vs. IPF mitochondria. (B) Normal subjects (n=3) and IPF patients (n=4). Mitochondria were isolated and immunoblot analysis for Rac1 was performed. Densitometry of mitochondrial Rac1 immunoblots normalized to VDAC. Normal vs. IPF is not significant. (C) Normal subjects (n=5) and IPF patients (n=7). Whole cell lysates were isolated immunoblot for Rac1 was performed.
Figure 7:
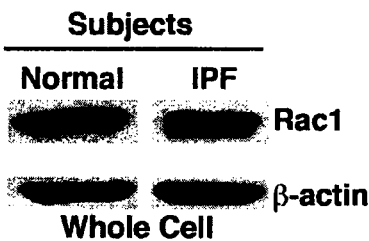
Figure 7:
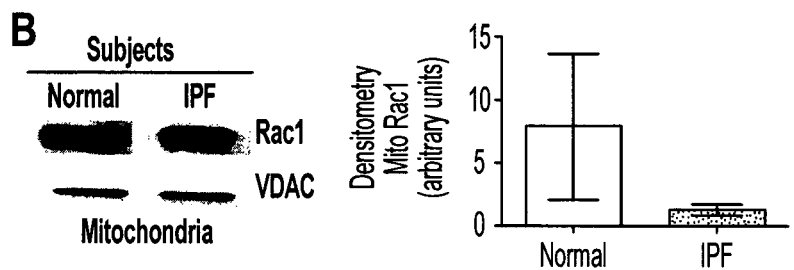
Figure 7:
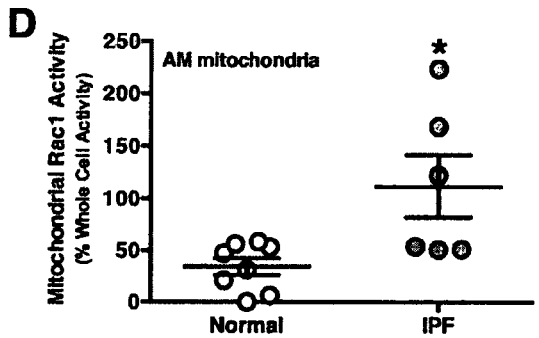

Studies demonstrate that the lungs of patients with IPF have an oxidant/antioxidant imbalance (Kliment, C. R. and T. D. Oury, *Oxidative stress, extracellular matrix targets, and idiopathic pulmonary fibrosis*. Free radical biology & medicine, 2010. 49(5): p. 707-17, Psathakis, K., et al., *Exhaled markers of oxidative stress in idiopathic pulmonary fibrosis*. Eur J Clin Invest, 2006. 36(5): p. 362-7, Rahman, I., et al., *Systemic and pulmonary oxidative stress in idiopathic pulmonary fibrosis*. Free radical biology & medicine, 1999. 27(1-2): p. 60-8). Because mitochondria-derived ROS production in macrophages contributes to pulmonary fibrosis (He, C., et al., *Mitochondrial Cu,Zn-Superoxide Dismutase Mediates Pulmonary Fibrosis by Augmenting H2O2 Generation*. J Biol Chem, 2011. 286(17): p. 15597-607, Murthy, S., et al., *Modulation of reactive oxygen species by Rac1 or catalase prevents asbestos-induced pulmonary fibrosis*. Am J Physiol Lung Cell Mol Physiol, 2009. 297(5): p. L846-55, Osborn-Heaford, H. L., et al., *Mitochondrial Rac1 GTPase Import and Electron Transfer from Cytochrome c Are Required for Pulmonary Fibrosis*. The Journal of biological chemistry, 2012. 287(5): p. 3301-12, Murthy, S., et al., *Rac1-mediated Mitochondrial H2O2 Generation Regulates MMP-9 Gene Expression in Macrophages via Inhibition of SP-1 and AP-1*. J Biol Chem, 2010. 285(32): p. 25062-73, He, C., et al., *Accelerated Development of Pulmonary Fibrosis via Cu,Zn-superoxide Dismutase-induced Alternative Activation of Macrophages*. J Biol Chem, 2013. 288(28): p. 20745-5, Jain, M., et al., *Mitochondrial reactive oxygen species regulate transforming growth factor-beta signaling*. J Biol Chem, 2013. 288(2): p. 770-7), mitochondrial $H_2O_2$ production in alveolar macrophages from IPF patients was evaluated. Isolated mitochondria from IPF patients showed significantly greater $H_2O_2$ levels compared to normal subjects (FIG. 7A). Because Rac1 has a direct effect on mitochondrial $H_2O_2$ levels by its localization to the mitochondrial intermembrane space (Osborn-Heaford, H. L., et al., *Mitochondrial Rac1 GTPase Import and Electron Transfer from Cytochrome c Are Required for Pulmonary Fibrosis*. The Journal of biological chemistry, 2012. 287(5): p. 3301-12), it was determined if there was a difference in localization of Rac1 in the mitochondria Immunoblot analysis demonstrated no significant difference in Rac1 in the mitochondria of normal subjects and IPF patients (FIG. 7B). Densitometry of immunoblot analyses showed no significant difference in mitochondrial Rac1 content. Whole cell Rac1 expression was also similar in normal subjects and IPF patients (FIG. 7C). Because mitochondrial Rac1 content does not necessarily correlate with Rac1 activity and Rac1, at least in part, mediates mitochondrial $H_2O_2$ generation (Osborn-Heaford, H. L., et al., *Mitochondrial Rac1 GTPase Import and Electron Transfer from Cytochrome c Are Required for Pulmonary Fibrosis*. The Journal of biological chemistry, 2012. 287(5): p. 3301-12, Murthy, S., et al., *Rac1-mediated Mitochondrial H2O2 Generation Regulates MMP-9 Gene Expression in Macrophages via Inhibition of SP-1 and AP-1*. J Biol Chem, 2010. 285(32): p. 25062-73), Rac1 activity in alveolar macrophage mitochondria from patients and normal subjects was measured. Rac1 activity in IPF mitochondria was significantly higher compared to normal subjects (FIG. 7D). These results suggest that Rac1-mediated alveolar macrophage oxidative stress is linked to pulmonary fibrosis (Heaford, H. L., et al, Murthy, S., et al.).

Impairment of Geranylgeranylation of Rac1 by DGBP Attenuates Rac1 Mitochondrial Import and Mitochondrial $H_2O_2$ Generation.

The C-terminal cysteines of Rho GTPases, including Rac1, are known to undergo geranylgeranylation, a post-transcriptional modification that is required for activation, interaction with other proteins, and mitochondrial import (Osborn-Heaford, H. L., et al., Mitochondrial Rac1 GTPase Import and Electron Transfer from Cytochrome c Are Required for Pulmonary Fibrosis. The Journal of biological chemistry, 2012. 287(5): p. 3301-12, Zeng, P. Y., et al., Role for RhoB and PRK in the suppression of epithelial cell transformation by farnesyltransferase inhibitors. Oncogene, 2003. 22(8): p. 1124-34). Geranylgeranylation is catalyzed by geranylgeranyltransferase (GGT), which transfers the geranylgeranyl moiety to the GTPase (FIG. 8A). Because previous data demonstrates that the absence of Rac1 in macrophage mitochondria attenuates fibrosis development, we synthesized a potent inhibitor of GGPP synthase, digeranyl bisphosphonate (DGBP) (FIG. 8B). DGBP was synthesized as previously described (Shull, L. W., Wiemer, A. J., Hohl, R. J., and Wiemer, D. F., Synthesis and biological activity of isoprenoid bisphosphonates. Bioorg Med Chem, 2006. 14(12): p. 4130-4136, Shull, L. W. a. W., D. F., Copper-mediated displacements of allylic THP ethers on a bisphosphonate template. J Organ Chem, 2005. 690(10): p. 2521-2530) and contains two polar groups that mimics pyrophosphate and binds to the active site of GGPP synthase, the enzyme that catalyzes the conversion of farnesyl diphosphate to GGPP (FIG. 8C).

To determine if DGBP inhibits Rac1 import into mitochondria, we exposed macrophages to vehicle (water) or DGBP in cells transfected with an empty control or a wild-type Rac1 expression vector (pRK-Flag-Rac1). Chrysotile induced localization of Rac1 to the mitochondria in cells expressing Flag-Rac1 and in cells incubated with 1 mM of DGBP (FIG. 8D). In contrast, Rac1 was absent from the mitochondria in the presence or absence of chrysotile exposure in cells incubated with 10 mM DGBP. To confirm that DGBP reduced Rac1 import secondary to inhibiting geranylgeranylation, an immunoblot analysis for Rap 1A, which only recognizes non-geranylgeranylated proteins and is indicative of reduced GGPP levels was performed (Weivoda, M. M. and R. J. Hohl, *The effects of direct inhibition of geranylgeranyl pyrophosphate synthase on osteoblast differentiation*. J Cell Biochem, 2011. 112(6): p. 1506-13, Wasko, B. M., A. Dudakovic, and R. J. Hohl, *Bisphosphonates induce autophagy by depleting geranylgeranyl diphosphate*. J Pharmacol Exp Ther, 2011. 337(2): p. 540-6). It was found that 10 mM of DGBP impaired Rap1A geranylgeranylation (FIG. 8E). To examine whether DGBP altered $H_2O_2$ levels, cells were treated similarly as above described with DGBP (10 mM). Chrysotile significantly increased $H_2O_2$ levels, whereas DGBP decreased $H_2O_2$ to control levels in both the presence and absence of chrysotile (FIG. 8F). In aggregate, the results demonstrate that inhibition of geranylgeranylation by altering GGPP synthase activity is an effective way to abrogate Rac1 mitochondrial import and oxidative stress in macrophages.

Bleomycin-Induced Oxidative Stress is Attenuated by DGBP.

To determine the effect of DGBP in vivo, bleomycin-exposed mice were utilized to investigate if DGBP modulated oxidative stress and fibrosis. It was first evaluated if bleomycin exposure increased mitochondrial oxidative stress in macrophages. WT mice were exposed to saline or bleomycin at a dose of 1.3 or 2.0 U/kg. After 21 days, bronchoalveolar lavage (BAL) was performed to obtain alveolar macrophages, and mitochondria were isolated. $H_2O_2$ levels were significantly elevated in alveolar macrophages obtained from mice exposed to bleomycin compared to saline. Further, bleomycin at 2.0 U/kg induced dramatically more mitochondrial $H_2O_2$ compared to the lower dose (FIG. 9A).

Because bleomycin increased mitochondrial oxidative stress in alveolar macrophages in vivo, it was next evaluated if bleomycin modulates Rac1 mitochondrial import. Osmotic pumps containing either vehicle (water) or DGBP were implanted subcutaneously in WT mice. DGBP was delivered at a dose of 0.2 mg/kg/day. Mice were exposed to saline or bleomycin the following day, and BAL was performed 21 days later to obtain alveolar macrophages. Mitochondria were isolated to investigate Rac1 localization. Bleomycin increased Rac1 mitochondrial localization compared to saline-exposed controls, whereas mice treated with DGBP showed significant reduction in immunoreactive Rac1 in mitochondria (FIG. 9B). To determine if DGBP impaired geranylgeranylation in vivo, an immunoblot analysis showed that non-geranylgeranylated Rap 1A was increased in BAL cells obtained from mice treated with DGBP indicating that it was effective. These data indicate that bleomycin induces Rac1 import into mitochondria, and this process is mediated by geranylgeranylation.

Because bleomycin increases mitochondrial Rac1 import and $H_2O_2$ levels in alveolar macrophages, it was investigated if mitochondrial $H_2O_2$ alters whole lung oxidative stress in the setting of pulmonary fibrosis. WT mice were exposed as above described in the presence of vehicle or DGBP. After 21 days, lungs were excised and homogenized to determine the percentage of total GSH in the disulfide, or oxidized, form. The lungs of mice that received the vehicle had a significantly higher oxidized GSH (% GSSG) than the lungs of mice that received DGBP (FIG. 9C). In aggregate, these data demonstrate that alveolar macrophages from bleomycin-exposed mice have increased mitochondrial $H_2O_2$ that mediates the increase in oxidative stress in the lung parenchyma. Furthermore, these data indicate that mitochondrial Rac1 is, in part, accountable for the oxidative stress as it is attenuated by impairment of Rac1 geranylgeranylation.

Pulmonary Fibrosis is Significantly Abrogated by DGBP.

Based on prior data linking mitochondrial oxidative stress to the development of pulmonary fibrosis (He, C., et al., *Mitochondrial Cu,Zn-Superoxide Dismutase Mediates Pulmonary Fibrosis by Augmenting H2O2 Generation*. J Biol Chem, 2011. 286(17): p. 15597-607, Osborn-Heaford, H. L., et al., *Mitochondrial Rac1 GTPase Import and Electron Transfer from Cytochrome c Are Required for Pulmonary Fibrosis*. The Journal of biological chemistry, 2012. 287(5): p. 3301-12, Murthy, S., et al., *Rac1-mediated Mitochondrial H2O2 Generation Regulates MMP-9 Gene Expression in Macrophages via Inhibition of SP-1 and AP-1*. J Biol Chem, 2010. 285(32): p. 25062-73, He, C., et al., *Accelerated Development of Pulmonary Fibrosis via Cu, Zn-superoxide Dismutase-induced Alternative Activation of Macrophages*. J Biol Chem, 2013. 288(28): p. 20745-57), it was determined if DGBP treatment would limit the fibrotic response to bleomycin-induced lung injury. The pro-fibrotic cytokine, TGF-β, in the active form in BAL fluid was measured. Mice were exposed to bleomycin while receiving vehicle or DGBP at 0.2 mg/kg/day. Mice treated with vehicle showed greater than 5-fold more active TGF-β in BAL fluid than mice that received DGBP (FIG. 9D). These data suggest that the reduction in lung oxidative stress limits the development of a pro-fibrotic environment.

To investigate for fibrosis development, the lungs were removed, fixed, and stained with Masson's trichrome to visualize collagen deposition. Bleomycin treatment resulted in widespread lung architectural destruction and large amounts of collagen deposition in animals that received vehicle (FIG. 9E). In contrast, the lungs of the DGBP-treated mice showed normal lung architecture (FIG. 9F). The histological observations were verified biochemically by a hydroxyproline assay. Mice treated with DGBP showed significantly less hydroxyproline following bleomycin exposure compared to mice given vehicle (FIG. 9G). Taken together, these data demonstrate that impairment of geranylgeranylation attenuates lung oxidative stress and pulmonary fibrosis and suggest a novel therapeutic target to limit the fibrotic response to lung injury.

Inhibition of GGPP Synthase with DGBP Halts Progression of Fibrosis.

To further investigate the therapeutic potential of arresting the development and/or progression of pulmonary fibrosis by impairing geranylgeranylation, mice were exposed to bleomycin and osmotic pumps were installed seven days after bleomycin exposure (FIG. 10A), as lung injury was present 7 days after bleomycin (data not shown). Lungs were excised and processed for Masson's trichrome staining 21 days after bleomycin to determine the extent of fibrosis. Bleomycin exposure in mice that received vehicle resulted in wide spread lung destruction and collagen deposition (FIG. 10B). In contrast, the lungs of mice treated with DGBP seven days after bleomycin showed small patches of collagen deposition, but there was significantly less collagen compared to mice that received vehicle (FIG. 10C). To confirm the histological findings, hydroxyproline content was measured in the lungs and found that mice treated with DGBP had significantly less hydroxyproline compared to the lungs of mice that received vehicle (FIG. 10D). In aggregate, these observations suggest that Rac1-mediated mitochondrial oxidative stress is linked to pulmonary fibrosis. Moreover, impairment of geranylgeranylation of Rac1, which is necessary for its mitochondrial import and oxidative stress, suggests that the isoprenylation pathway is a novel target for pulmonary fibrosis following lung injury.

Geranylgeranylation of Rac1 is Required for Chrysotile-Induced Pulmonary Fibrosis.

Figures 11A, 11B, 11C, 11D:
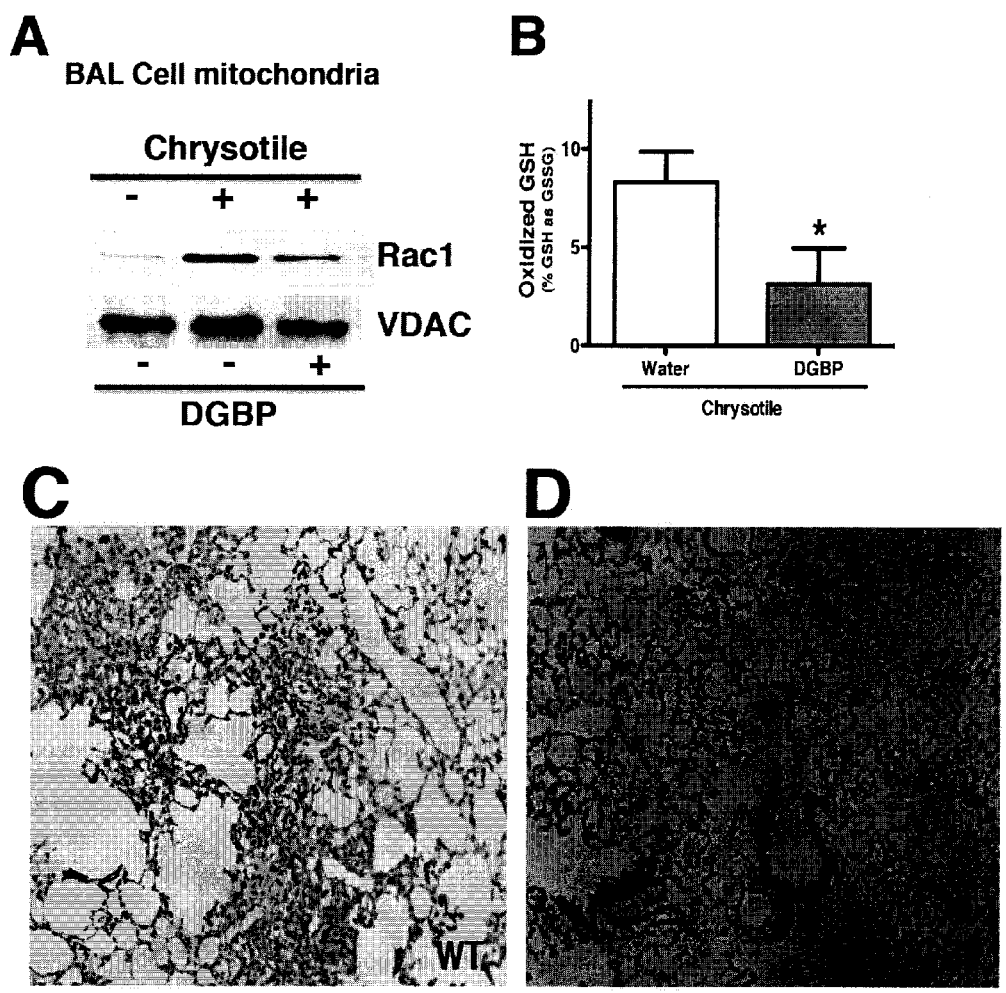

To determine if geranylgeranylation of Rac1 is associated with other forms of pulmonary fibrosis, the role of DGBP in modulating chrysotile-induced pulmonary fibrosis was tested. WT mice with subcutaneous osmotic pumps delivering vehicle or DGBP were exposed to chrysotile as previously described (He, C., et al., *Mitochondrial Cu,Zn-Superoxide Dismutase Mediates Pulmonary Fibrosis by Augmenting H2O2 Generation*. J Biol Chem, 2011. 286(17): p. 15597-607, Osborn-Heaford, H. L., et al., *Mitochondrial Rac1 GTPase Import and Electron Transfer from Cytochrome c Are Required for Pulmonary Fibrosis*. The Journal of biological chemistry, 2012. 287(5): p. 3301-12, Murthy, S., et al., *Rac1-mediated Mitochondrial H2O2 Generation Regulates MMP-9 Gene Expression in Macrophages via Inhibition of SP-1 and AP-1*. J Biol Chem, 2010. 285(32): p. 25062-73). It was first determined if DGBP altered mitochondrial Rac1 localization in BAL cells. Alveolar macrophages were obtained by BAL 21 days after chrysotile exposure. Mitochondria isolated from mice exposed to chrysotile had greater Rac1 content in mitochondria than mice treated with saline, whereas mitochondrial Rac1 content was similar to control levels in the mice treated with DGBP (FIG. 11A). Lung oxidative stress was also evaluated. Mice that received vehicle showed 2.5-fold more oxidized GSH (% GSSG) in the lung than mice treated with DGBP (FIG. 11B).

DGBP Protected Mice from Developing Pulmonary Fibrosis after Chrysotile Exposure.

Figures 11E, 11F, 11G, 11H:
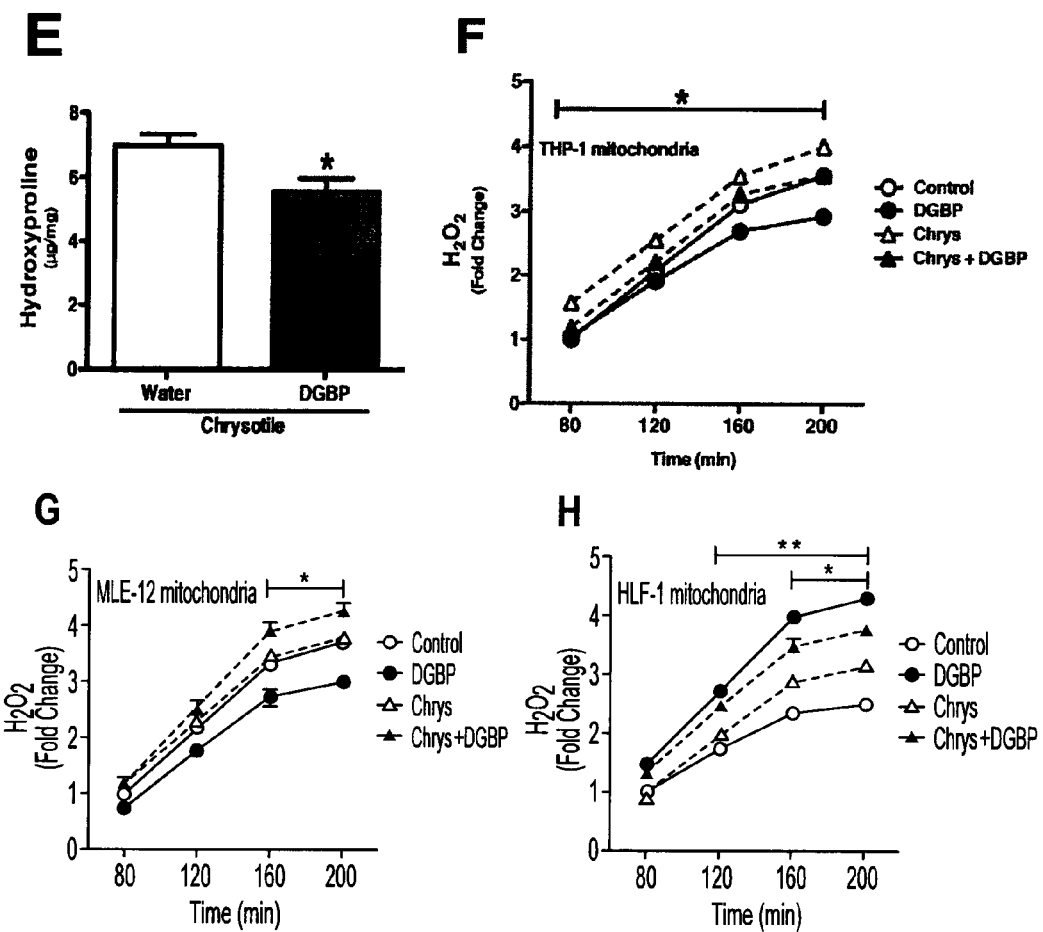

To further evaluate the effect of DGBP in protecting mice from pulmonary fibrosis, osmotic pumps containing vehicle or DGBP were implanted in WT mice, and the mice were exposed to chrysotile. The mice were euthanized after 21 days, and lungs were removed and processed for Masson's trichrome staining. Mice that received vehicle had significant architectural changes in their lung parenchyma and large amounts of collagen deposition (FIG. 11C). The lungs of the mice that received DGBP were essentially normal (FIG. 11D). The histological findings were confirmed by hydroxyproline assay (FIG. 11E). In aggregate, these observations suggest that mitochondrial Rac1 is critical for not only regulating oxidative stress but also the fibrotic response to lung injury. Moreover, the use of DGBP to limit the development of the fibrotic phenotype after lung injury is therapeutically novel.

DGBP is Specific for Altering Oxidative Stress in Alveolar Macrophages.

Because the systemic delivery of DGBP can affect multiple cell types and numerous cells, such as alveolar macrophages, alveolar epithelial cells and fibroblasts, are important in pulmonary fibrosis, it was investigated if DGBP modulated mitochondrial oxidative stress in other cell types. THP-1, MLE-12, and HLF-1 cells were cultured in the presence or absence of DGBP overnight and then exposed to chrysotile for 1 h. Mitochondria were isolated to measure $H_2O_2$ generation. Chrysotile increased $H_2O_2$ in THP-1 mitochondria in a time-dependent manner, whereas DGBP reduced chrysotile-induced $H_2O_2$ significantly at all time points (FIG. 11F). In contrast, chrysotile did not alter mitochondrial $H_2O_2$ in MLE-12 cells, but DGBP increased $H_2O_2$ generation in cells exposed to chrysotile (FIG. 11G). Similar to the THP-1 cells, chrysotile increased mitochondrial $H_2O_2$ levels in HLF-1 cells, whereas DGBP increased $H_2O_2$ in the presence or absence of chrysotile (FIG. 11H). Because DGBP reduced lung oxidative stress in mice, these data indicate that impairment of geranylgeranylation in macrophages, rather than alveolar epithelial cells or fibroblasts, is the primary effect of DGBP treatment. Moreover, these data suggest that macrophage-derived mitochondrial ROS plays a critical role in mediating the lung oxidative stress and the development of pulmonary fibrosis.

Discussion

Pulmonary fibrosis is a devastating lung disease that is increasing in incidence. In particular, IPF has a grim prognosis, and supportive care is the primary means of treatment as no current therapeutic modalities are available to halt its progression. The studies described herein had the purpose to abrogate the development and progression of pulmonary fibrosis by focusing on the modulation of mitochondrial oxidative stress in alveolar macrophages, which is critical to the fibrotic response to lung injury. By disrupting the isoprenoid pathway as a therapeutic target, it was found that inhibiting geranylgeranylation attenuated Rac1-mediated oxidative stress and the progression of pulmonary fibrosis.

The isoprenoid pathway is a target for drug therapy in multiple conditions. Statins are the most widely prescribed drug in the United States and are used to inhibit 3-hydroxy-3-methylglutaryl (HMG)-CoA reductase, which is the rate-limiting enzyme that converts HMG-CoA to mevalonate. Statins are clearly important in the management of hypercholesterolemia as well as the prevention of stroke. The isoprenoid pathway is also disrupted for the treatment of osteoporosis. The bisphosphonates adsorb to bone mineral and reduce bone resorption by inhibition of farnesyl diphosphate synthase, which synthesizes farnesyl diphosphate through successive condensations of isopentyl pyrophosphate with dimethylallyl pyrophosphate and geranyl pyrophosphate. The treatment of infectious diseases, including S. aureus sepsis, with statins is known to prevent host cell invasion, and isoprenoid products are necessary for formation of the cell wall peptidoglycan. Agents that disrupt the isoprenoid pathway have been used for cancer therapeutically. Farnesyl transferase (FTase), which catalyzes the farnesylation of the Ras proteins, and geranylgeranyltranferase I (GGTase I), which catalyzes the final step in the lipid post-translational modification of Rho GTPases, have been studied because Ras and Rho GTPases have been shown to be essential for cell growth and proliferation. It is believed that the isoprenoid pathway has not been targeted as a treatment strategy for pulmonary fibrosis. In fact, statins are associated with an increase in interstitial lung abnormalities in smokers. The studies described herein demonstrate that the inhibition of GGPP synthase, the enzyme that catalyzes the conversion of farnesyl diphosphate to GGPP, abrogates bleomycin- and chrysotile-induced pulmonary fibrosis by blocking Rac1 isoprenylation in alveolar macrophages.

DGBP inhibits GGPP synthase by mimicking pyrophosphate with its two polar groups that bind to the active site of GGPP synthase. The hydrophobic chains bind to the interior of the enzyme at the site where GGPP would be released. GGTase deficiency was shown to induce pro-inflammatory gene expression in macrophages, and most of the Rac1 was localized to the plasma membrane suggesting that inactivation of GGTases, and, thus geranylgeranylation, results in activation of Rho GTPases. These results indicate that the reduction of GGPP limits the geranylgeranylation of Rac1 by GGT. DGBP has the potential to limit the isoprenylation of other Ras and Rho GTPases, but at the concentrations and doses used in the studies this is not associated with apparent toxicity in vitro or in vivo. In aggregate, these studies demonstrate that the isoprenoid pathway is a novel target to impair geranylgeranylation to attenuate development and/or progression of pulmonary fibrosis.

Prior studies have demonstrated the importance of Rac1 activation in the development of pulmonary fibrosis following exposure to chrysotile; however, this study reveals that mitochondrial Rac1 activity is increased in the alveolar macrophages obtained from IPF patients. The C-terminal cysteine of Rac1 ($Cys^{189}$) must be geranylgeranylated for activation and import into the mitochondria. It has been discovered that chrysotile decreases Rac1 activity in the cell membrane and cytosol, whereas it increased activity in the mitochondria in macrophages (data not shown). Although it was found that mitochondrial Rac1 content was similar in IPF patients and normal subjects, the mitochondrial activity of Rac1 was dramatically different suggesting that Rac1 is preferentially activated in the mitochondria, Oxidative stress has recently been linked to TGF-β activation and Smad signaling in multiple organ systems. This link is important because a reduction in oxidative stress results in limited TGF-β activation and attenuation in matrix remodeling. In addition, mitochondrial oxidative stress is directly associated with TGF-β-mediated Smad signaling, which results in fibrotic remodeling. The results described herein indicate that DGBP treatment in vivo significantly limits the level of active TGF-β in BAL fluid and decreases oxidation of GSH, which indicates less oxidative stress in the lung parenchyma. The observations from the studies support the link between mitochondrial oxidative stress and TGF-β levels, but it further provides a novel therapeutic agent that abrogates the fibrotic phenotype.

The lungs of IPF patients are considered to have an oxidant/antioxidant imbalance. It was found that IPF alveolar macrophages have increased mitochondrial $H_2O_2$ levels, and that altering Rac1 mitochondrial import in vivo with DGBP decreased lung oxidative stress. The primary source of ROS in macrophages is the mitochondria in inflammatory and fibrotic states, and mitochondrial Rac1 import, at least in part, regulates mitochondrial $H_2O_2$ levels in these conditions by promoting electron transfer from cytochrome c to Rac1. Inhibition of mitochondrial ROS or a conditional deletion of Rac1 in macrophages significantly attenuates development of pulmonary fibrosis and highlights the importance of macrophages in aberrant lung repair following injury. The studies described herein demonstrate that DGBP reduced $H_2O_2$ levels in macrophages, whereas DGBP increased $H_2O_2$ levels in alveolar epithelial and fibroblast cells. Multiple studies have shown that the alveolar epithelium and fibroblasts have a critical role in inducing the development of pulmonary fibrosis; however, the findings herein demonstrate that alveolar macrophage-derived oxidative stress is linked to the development of a fibrotic phenotype, and inhibition of GGPP synthase in the isoprenoid pathway can attenuate progression of the fibrosis. Taken together, these results uncover a mechanism that mediates pulmonary fibrosis and provides a novel therapy that abrogates progression of the fibrotic phenotype by targeting the isoprenoid pathway.

All publications, patents, and patent documents cited herein are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method to treat pulmonary fibrosis in an animal in need thereof comprising administering to the animal an effective amount of a compound of formula I, formula II or formula III:

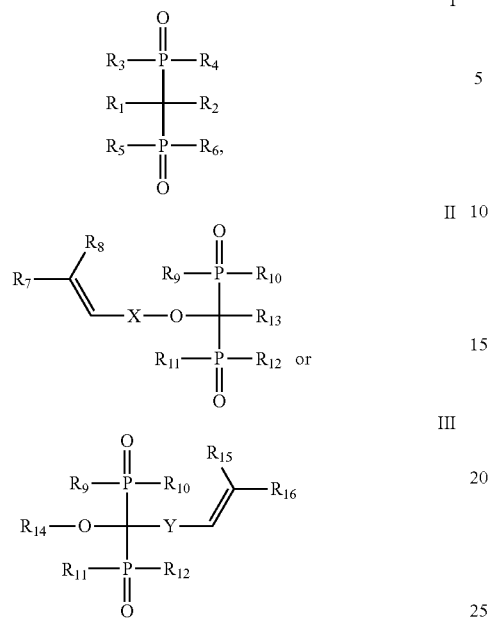

wherein:
- $R_1$ is a saturated or unsaturated ($C_5$-$C_{20}$)alkyl chain that optionally comprises one or more aryl rings in the chain and that is optionally substituted with one or more halo, trifluoromethyl, —$OR_a$, —P(=O)($OR_a$)$_2$, or —$NR_bR_c$;
- $R_2$ is a saturated or unsaturated ($C_5$-$C_{20}$)alkyl chain that optionally comprises one or more aryl rings in the chain and that is optionally substituted with one or more halo, trifluoromethyl, —$OR_a$, —P(=O)($OR_a$)$_2$, or —$NR_bR_c$;
- each $R_3$, $R_4$, $R_5$, and $R_6$ is independently OH or ($C_1$-$C_6$)alkoxy;
- each $R_a$ is independently H, ($C_1$-$C_6$)alkyl, or aryl; and each $R_b$ and $R_c$ is independently H, ($C_1$-$C_6$)alkyl, or aryl; or $R_b$ and $R_c$ together with the nitrogen to which they are attached form a pyrrolidino, piperidino, morpholino, or thiomorpholino ring;
- wherein any aryl of $R_1$, $R_2$, $R_a$, $R_b$ or $R_c$ is optionally substituted with one or more ($C_1$-$C_6$)alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, halo, cyano, nitro, carboxy, trifluoromethyl, trifluoromethoxy, $NR_dR_e$, or S(O)$_2NR_dR_e$, wherein each $R_d$ and $R_e$ is independently H or ($C_1$-$C_6$)alkyl;
- X is ($C_1$-$C_6$)alkyl;
- Y is ($C_1$-$C_6$)alkyl;
- $R_7$ is a saturated or unsaturated ($C_1$-$C_{20}$)alkyl chain that optionally comprises one or more aryl or heteroaryl rings in the chain wherein ($C_1$-$C_{20}$)alkyl is optionally substituted with one or more halo, cyano, nitro, carboxy, trifluoromethyl, trifluoromethoxy, aryl, heteroaryl, $NR_mR_n$ or S(O)$_2NR_pR_q$ and wherein any aryl or heteroaryl is optionally substituted with one or more ($C_1$-$C_6$)alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, halo, cyano, nitro, carboxy, trifluoromethyl, trifluoromethoxy, $NR_{a1}R_{b1}$, or S(O)$_2NR_{c1}R_{d1}$;
- $R_8$ is H or a saturated or unsaturated ($C_1$-$C_{20}$)alkyl chain that optionally comprises one or more aryl or heteroaryl rings in the chain wherein ($C_1$-$C_{20}$)alkyl is optionally substituted with one or more halo, cyano, nitro, carboxy, trifluoromethyl, trifluoromethoxy, aryl, heteroaryl, $NR_mR_n$, or S(O)$_2NR_pR_q$ and wherein any aryl or heteroaryl is optionally substituted with one or more ($C_1$-$C_6$)alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, halo, cyano, nitro, carboxy, trifluoromethyl, trifluoromethoxy, $NR_{a1}R_{b1}$, or S(O)$_2NR_{c1}R_{d1}$;
- each $R_9$, $R_{10}$, $R_{11}$, and $R_{12}$ is independently OH or ($C_1$-$C_6$)alkoxy;
- $R_{13}$ is a saturated or unsaturated ($C_1$-$C_{20}$)alkyl chain that optionally comprises one or more aryl or heteroaryl rings in the chain wherein ($C_1$-$C_{20}$)alkyl is optionally substituted with one or more halo, cyano, nitro, carboxy, trifluoromethyl, trifluoromethoxy, aryl, heteroaryl, $NR_mR_n$, or S(O)$_2NR_pR_q$ and wherein any aryl or heteroaryl is optionally substituted with one or more ($C_1$-$C_6$)alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, halo, cyano, nitro, carboxy, trifluoromethyl, trifluoromethoxy, $NR_{a1}R_{b1}$, aryl, heteroaryl, or S(O)$_2NR_{c1}R_{d1}$;
- $R_{14}$ is a saturated or unsaturated ($C_1$-$C_{20}$)alkyl chain that optionally comprises one or more aryl or heteroaryl rings in the chain wherein ($C_1$-$C_{20}$)alkyl is optionally substituted with one or more halo, cyano, nitro, carboxy, trifluoromethyl, trifluoromethoxy, aryl, heteroaryl, $NR_mR_n$, or S(O)$_2NR_pR_q$ and wherein any aryl or heteroaryl is optionally substituted with one or more ($C_1$-$C_6$)alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, halo, cyano, nitro, carboxy, trifluoromethyl, trifluoromethoxy, $NR_{a1}R_{b1}$, aryl, heteroaryl, or S(O)$_2NR_{c1}R_{d1}$;
- $R_{15}$ is a saturated or unsaturated ($C_1$-$C_{20}$)alkyl chain that optionally comprises one or more aryl or heteroaryl rings in the chain wherein ($C_1$-$C_{20}$)alkyl is optionally substituted with one or more halo, cyano, nitro, carboxy, trifluoromethyl, trifluoromethoxy, aryl, heteroaryl, $NR_mR_n$, or S(O)$_2NR_pR_q$ and wherein any aryl or heteroaryl is optionally substituted with one or more ($C_1$-$C_6$)alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, halo, cyano, nitro, carboxy, trifluoromethyl, trifluoromethoxy, $NR_{a1}R_{b1}$, or S(O)$_2NR_{c1}R_{d1}$;
- $R_{16}$ is H or a saturated or unsaturated ($C_1$-$C_{20}$)alkyl chain that optionally comprises one or more aryl or heteroaryl rings in the chain wherein ($C_1$-$C_{20}$)alkyl is optionally substituted with one or more halo, cyano, nitro, carboxy, trifluoromethyl, trifluoromethoxy, aryl, heteroaryl, $NR_mR_n$, or S(O)$_2NR_pR_q$ and wherein any aryl or heteroaryl is optionally substituted with one or more ($C_1$-$C_6$)alkyl, ($C_1$-$C_6$)alkoxy, ($C_1$-$C_6$)alkanoyl, ($C_1$-$C_6$)alkanoyloxy, ($C_1$-$C_6$)alkoxycarbonyl, halo, cyano, nitro, carboxy, trifluoromethyl, trifluoromethoxy, $NR_{a1}R_{b1}$, or S(O)$_2NR_{c1}R_{d1}$;
- each $R_{a1}$ and $R_{b1}$ is independently H, ($C_1$-$C_6$)alkyl, or aryl; or $R_{a1}$ and $R_{b1}$ together with the nitrogen to which they are attached form a pyrrolidino, piperidino, morpholino, or thiomorpholino ring;
- each $R_{c1}$ and $R_{d1}$ is independently H, ($C_1$-$C_6$)alkyl, or aryl; or $R_{c1}$ and $R_{d1}$ together with the nitrogen to which they are attached form a pyrrolidino, piperidino, morpholino, or thiomorpholino ring;
- each $R_p$ and $R_q$ is independently H, ($C_1$-$C_6$)alkyl, or aryl; or $R_p$ and $R_q$ together with the nitrogen to which they are attached form a pyrrolidino, piperidino, morpholino, or thiomorpholino ring;

each $R_p$ and $R_q$ is independently H, $(C_1-C_6)$alkyl, or aryl; or $R_p$ and $R_q$ together with the nitrogen to which they are attached form a pyrrolidino, piperidino, morpholino, or thiomorpholino ring; and wherein any aryl of $R_{a1}$, $R_{b1}$, $R_{c1}$, $R_{d1}$, $R_m$, $R_n$, $R_p$ or $R_q$ is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_sR_t$, or $S(O)_2NR_sR_t$ wherein each $R_s$ and $R_t$ is independently H or $(C_1-C_6)$alkyl;

or a pharmaceutically acceptable salt or prodrug thereof.

2. The method of claim 1, comprising administering to the animal a compound of formula I:

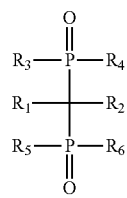

I or a pharmaceutically acceptable salt or prodrug thereof.

3. The method of claim 1, wherein $R_1$ is of the formula,

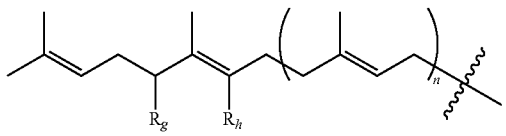

wherein:

n is 0, 1, or 2; and $R_g$ and $R_h$ together with the atoms to which they are attached form an aryl ring that is optionally substituted with one or more (e.g. 1, 2, 3, or 4) $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl.

4. The method of claim 1, wherein $R_1$ is of the formula,

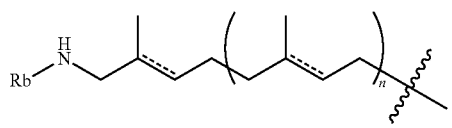

wherein:

n is 0, 1, 2, or 3;

each bond designated by ----- is independently either present or is absent; and $R_b$ is phenyl or naphthyl and is optionally substituted with one or more carboxy or $S(O)_2NR_dR_e$, wherein each $R_d$ and $R_e$ is independently H or $(C_1-C_6)$alkyl.

5. The method of claim 3, wherein $R_2$ is of the formula,

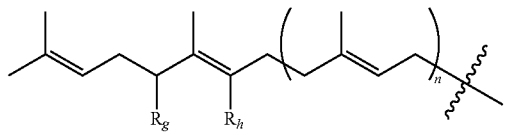

wherein:

n is 0, 1, or 2; and $R_g$ and $R_h$ together with the atoms to which they are attached form an aryl ring that is optionally substituted with one or more (e.g. 1, 2, 3, or 4) $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_dR_e$, or $S(O)_2NR_dR_e$, wherein each $R_d$ and $R_e$ is independently H or $(C_1-C_6)$alkyl.

6. The method of claim 3, wherein $R_2$ is of the formula,

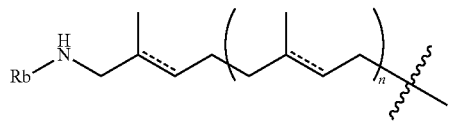

wherein:

n is 0, 1, 2, or 3;

each bond designated by ----- is independently either present or is absent; and $R_b$ is phenyl or naphthyl and is optionally substituted with one or more carboxy or $S(O)_2NR_dR_e$, wherein each $R_d$ and $R_e$ is independently H or $(C_1-C_6)$alkyl.

7. The method of claim 1 wherein the compound is:

tetramethyl (E)-1,1-bis(4,8-dimethyl-nona-3,7-dienyl)-1,1-bisphosphonate, tetraethyl 4,8-dimethyl-3,7-nonadienyl-1,1-bisphosphonate, tetraethyl (2E,6E)-1-(3-methyl-but-2-enyl)-3,7,11-trimethyl-dodeca-2,6,10-trienyl-1,1-bisphosphonate, 1-(3,7-dimethyl-octa-2,6-dienyl)-4,8-dimethyl-nona-3,7-dienyl-1,1-bisphosphonic acid, tetrasodium salt, tetrapivaloyloxymethyl (E)-1,1-bis(4,8-dimethyl-nona-3,7-dienyl)-1,1-bisphosphonate, or (2E,6E)-1-(3-methyl-but-2-enyl)-3,7,11-trimethyl-dodeca-2,6,10-triene-1,1-bisphosphonate, or a pharmaceutically acceptable salt or prodrug thereof.

8. The method of claim 1, comprising administering to the animal a compound of formula II, or a pharmaceutically acceptable salt or prodrug thereof.

9. The method of claim 8, wherein $R_7$ is

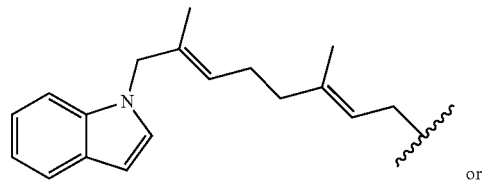

or

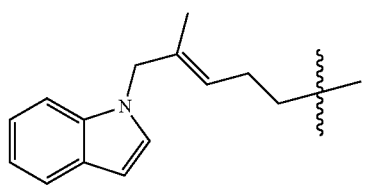
10. The method of claim 1, comprising administering to the animal a compound of formula III, or a pharmaceutically acceptable salt or prodrug thereof.
11. The method of claim 1 wherein the compound is:
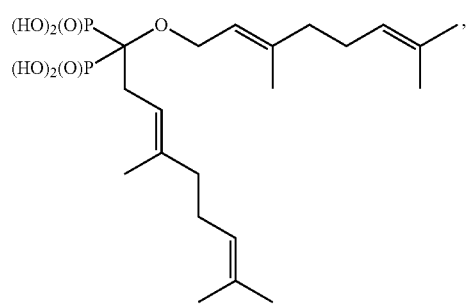
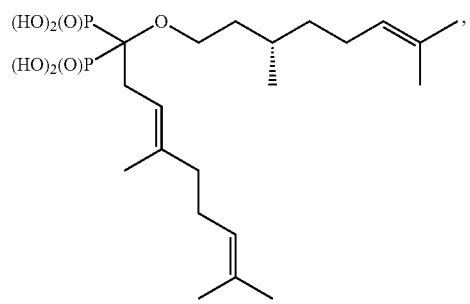
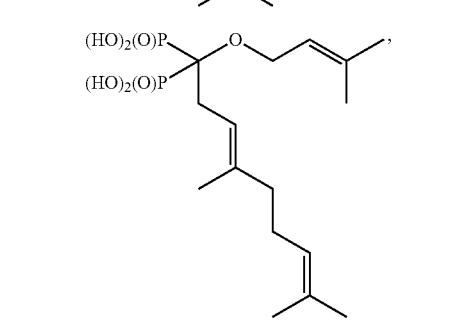
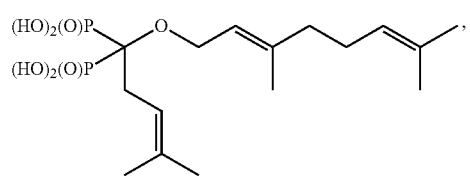
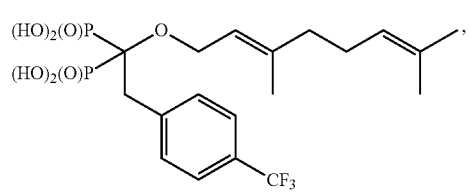
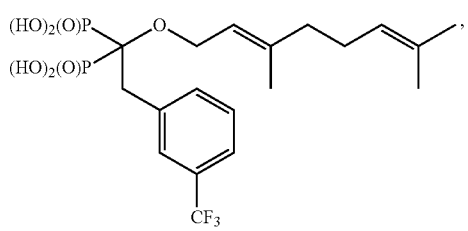
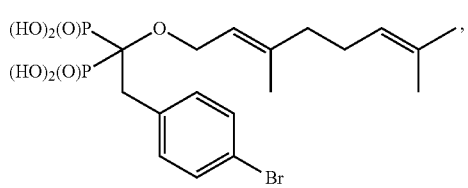
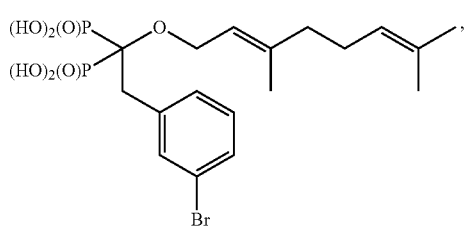
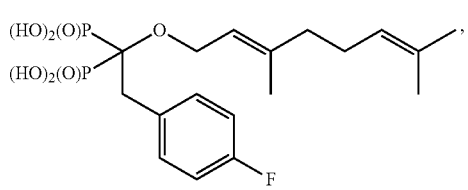
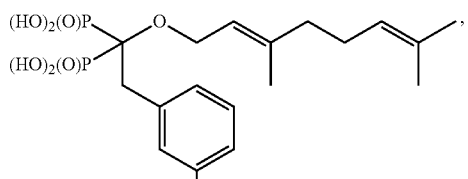
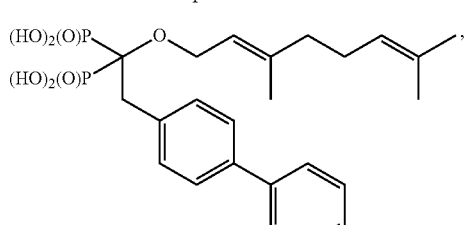
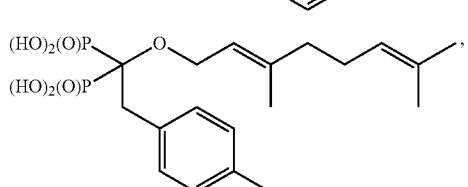

65
-continued
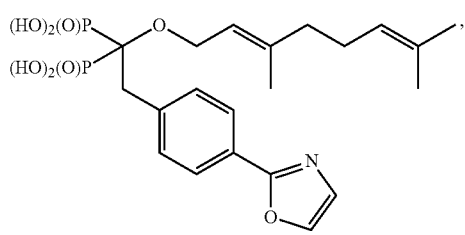
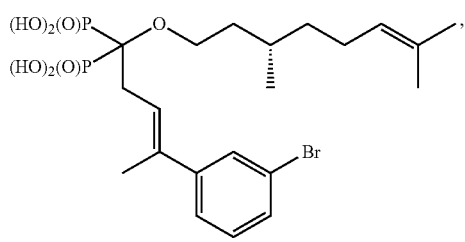
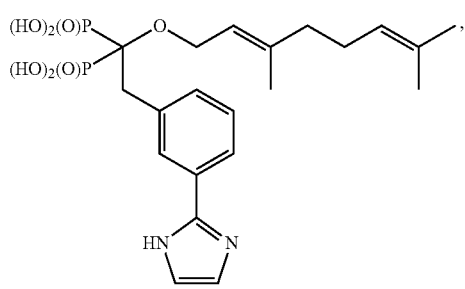
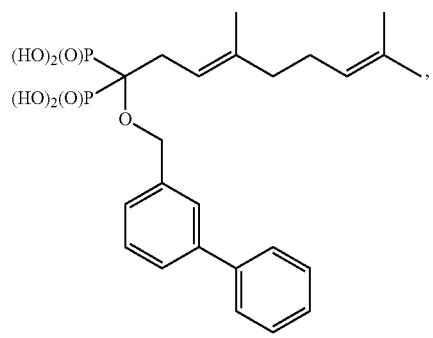
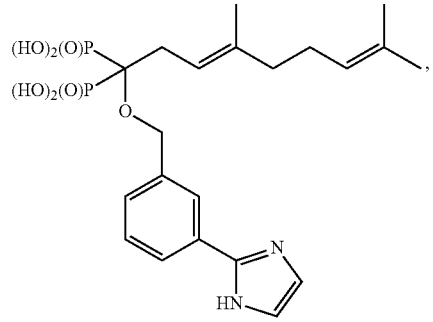
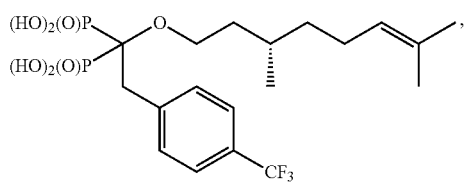
66
-continued
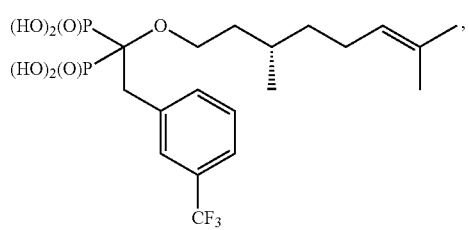
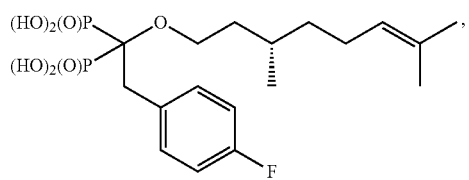
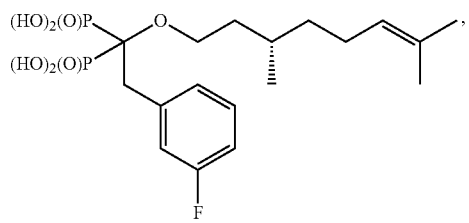
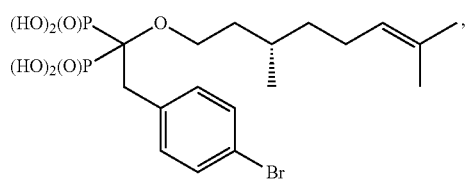
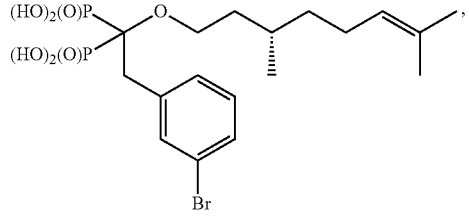
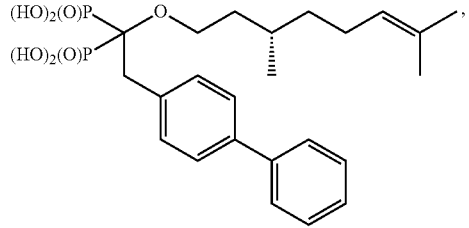
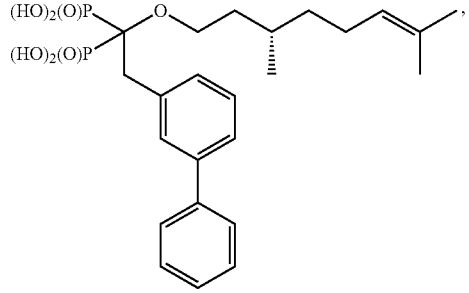

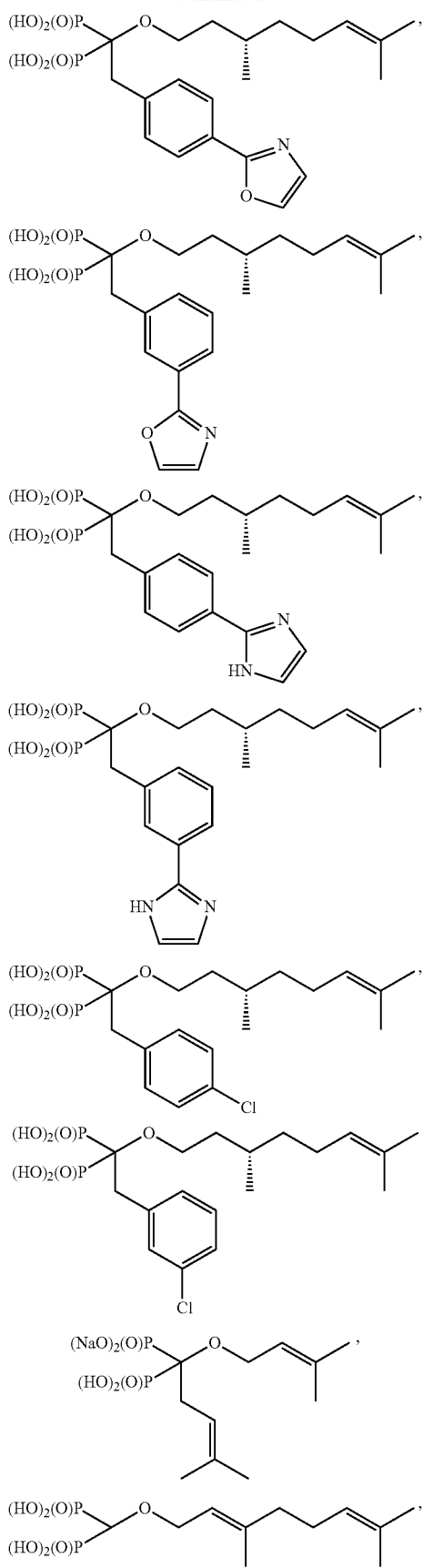
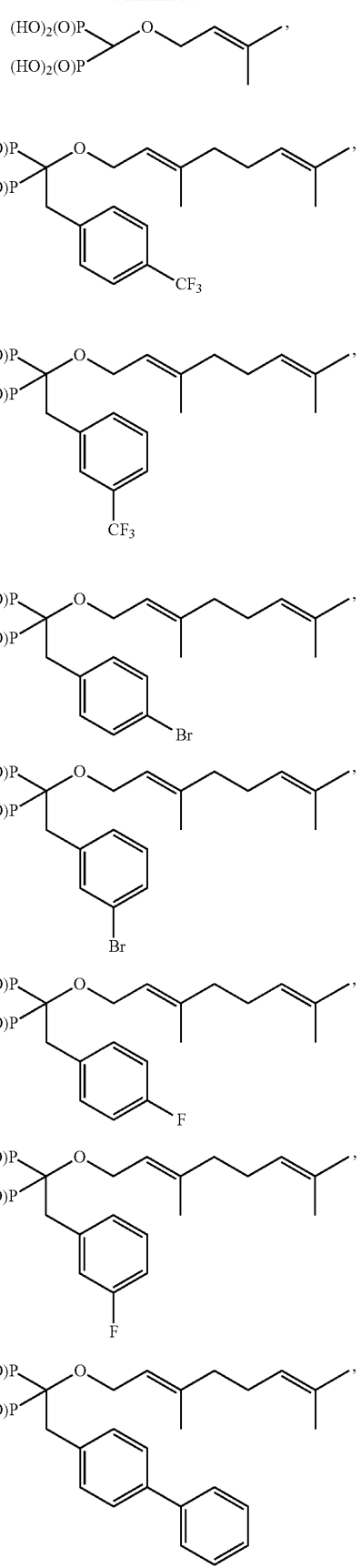

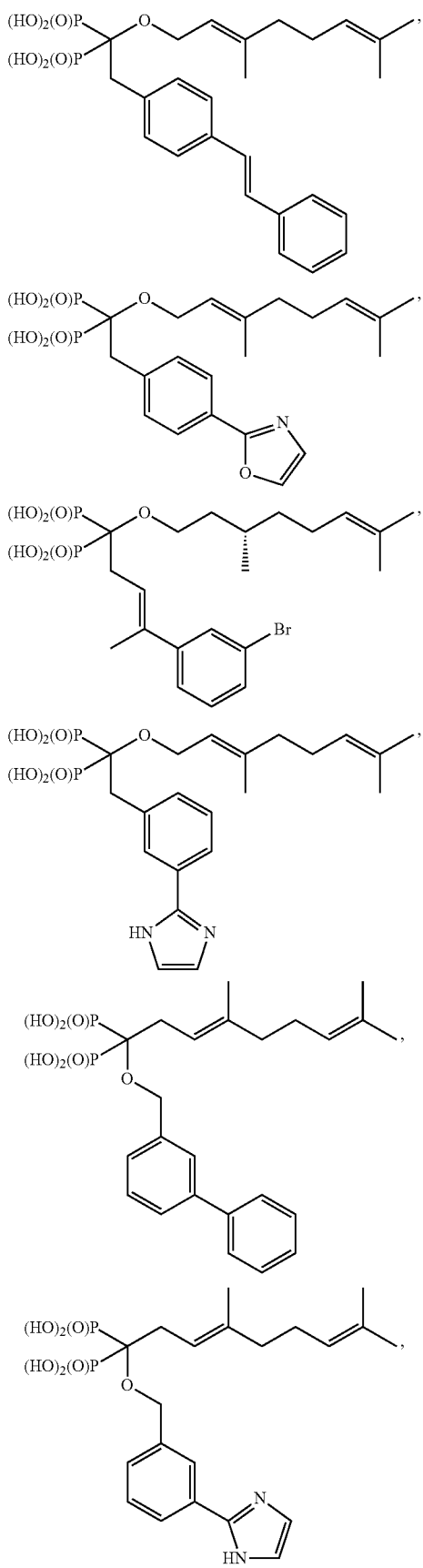
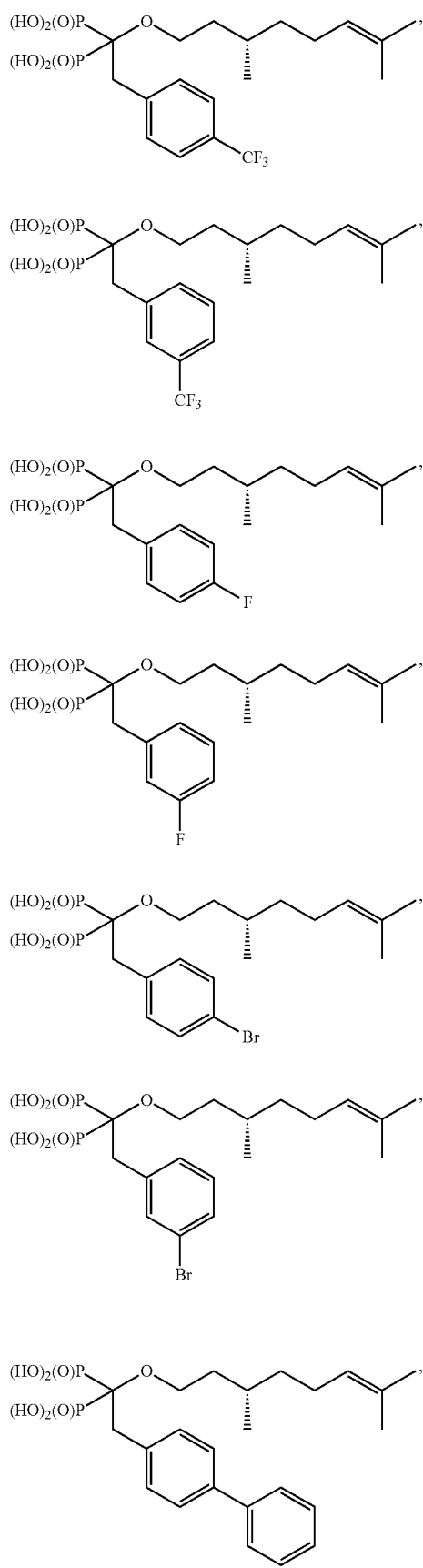

-continued
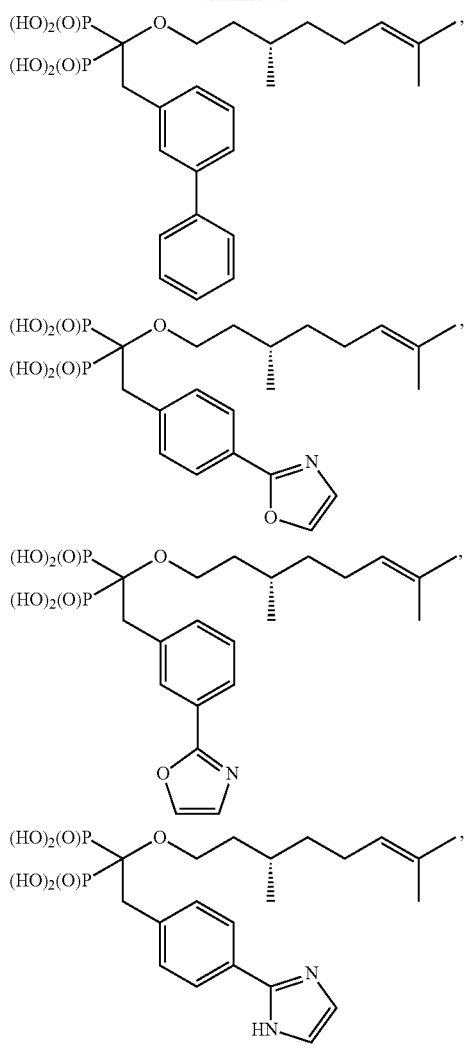
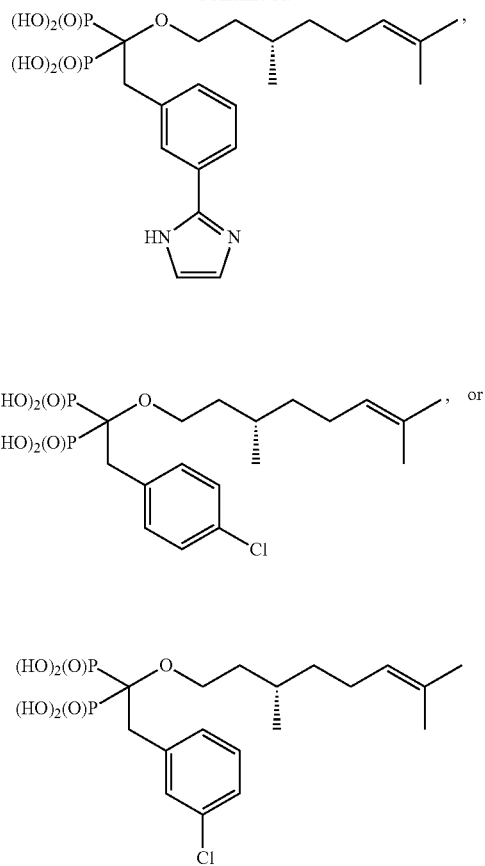
or a pharmaceutically acceptable salt or prodrug thereof.
12. The method of claim 1, wherein the compound of formula I, or the pharmaceutically acceptable salt or prodrug thereof is digeranyl bisphosphonate, or a pharmaceutically acceptable salt or prodrug thereof.
* * * * *